US009655912B2

(12) United States Patent
Mahdavi et al.

(10) Patent No.: US 9,655,912 B2
(45) Date of Patent: May 23, 2017

(54) REDUCTION OF GASTROINTESTINAL TRACT COLONISATION BY CAMPYLOBACTER

(71) Applicant: Akeso Biomedical, Inc., Waltham, MA (US)

(72) Inventors: Jafar Mahdavi, Nottingham (GB); Dlawer Ala'Aldeen, Nottingham (GB)

(73) Assignee: Akeso Biomedical, Inc., Waltham, MA (US)

( * ) Notice: Subject to any disclaimer, the term of this patent is extended or adjusted under 35 U.S.C. 154(b) by 96 days.

(21) Appl. No.: 14/379,473

(22) PCT Filed: Feb. 15, 2013

(86) PCT No.: PCT/GB2013/050367
§ 371 (c)(1),
(2) Date: Aug. 18, 2014

(87) PCT Pub. No.: WO2013/121214
PCT Pub. Date: Aug. 22, 2013

(65) Prior Publication Data
US 2015/0025026 A1 Jan. 22, 2015

(30) Foreign Application Priority Data

Feb. 16, 2012 (GB) .................................. 1202681.1
Nov. 8, 2012 (GB) .................................. 1220158.8

(51) Int. Cl.
| | | |
|---|---|---|
| *A61K 31/16* | (2006.01) | |
| *A61K 31/164* | (2006.01) | |
| *A61K 31/191* | (2006.01) | |
| *A61K 31/195* | (2006.01) | |
| *A61K 31/295* | (2006.01) | |
| *A61K 31/7008* | (2006.01) | |
| *A61K 31/335* | (2006.01) | |
| *A61K 31/555* | (2006.01) | |
| *A61K 31/132* | (2006.01) | |
| *A61K 31/136* | (2006.01) | |
| *A61K 31/661* | (2006.01) | |
| *C12Q 1/18* | (2006.01) | |
| *A23K 20/111* | (2016.01) | |
| *A23K 50/75* | (2016.01) | |

(52) U.S. Cl.
CPC ........ *A61K 31/7008* (2013.01); *A23K 20/111* (2016.05); *A23K 50/75* (2016.05); *A61K 31/132* (2013.01); *A61K 31/136* (2013.01); *A61K 31/164* (2013.01); *A61K 31/191* (2013.01); *A61K 31/295* (2013.01); *A61K 31/335* (2013.01); *A61K 31/555* (2013.01); *A61K 31/661* (2013.01); *C12Q 1/18* (2013.01)

(58) Field of Classification Search
CPC .... A61K 31/16; A61K 31/164; A61K 31/191; A61K 31/195; A61K 31/295; A61K 31/7008
See application file for complete search history.

(56) References Cited

U.S. PATENT DOCUMENTS

2004/0265427 A1* 12/2004 Boren .................. A23L 1/1016
426/52
2007/0249553 A1 10/2007 Newell

FOREIGN PATENT DOCUMENTS

| WO | 03040351 | 5/2003 |
| WO | 2005055944 | 6/2005 |
| WO | 2006045017 | 5/2006 |

OTHER PUBLICATIONS

Definition of "prevention" from the Institute for International Medical Education [online], [Retrieved on Mar. 24, 2011]. Retrieved from the Internet <http://www.iime.org/glossary.htm>. Published Feb. 2002, p. 1, 2, 26, 27 and 39.*
Dasti, J.I., Malik Tareen, A., Lugert, R., Zautner, A., Groβ, U. (2010) Campylobacter jejuni: A brief overview on pathogenicity-associated factors and disease-mediating mechanism. International Journal of Medical Microbiology, vol. 300, p. 205-211.*
Cervantes, L.-E., Newburg, D.S., Ruiz-Palacios, G.M. (1996) "α1-2 Fucosylated Chains (H-2, H-1, and Lewis b) are the Main Human Milk Receptor Analogs for Campylobacter" in Campylobacters, Helicobacters, and Related Organisms. Edited by D.G. Newell et al., New York, p. 653-658.*
Refat, M.S., El-Korashy, S.A., Ahmed, A.S. (2008) Preparation, structural characterization and biological evaluation of L-tyrosinate metal ion complexes. Journal of Molecular Structure, vol. 881, p. 28-45.*
Zeng, K. et al "Synthesis and biological evaluation of quinic acid derivatives . . . " Bioorg. Med. Chem. Lett. (2009) vol. 19, pp. 5458-5460.*
Barco, et al, "D-( )-Quinic acid: a chiron store for natural product synthesis", Tetrahedron:Asymmetry, 8(21):3515-45 (1997).
Golden, et al., "Identification of Motility and Autoagglutination Campylobacter jejuni Mutants by Random Transposon Mutagenesis", Infect Immun., 70(4):1761-71 (2002).
Lee, et al., "Chitin Regulation of Immune Responses: An Old Molecule With New Roles", Curr Opin Immunol., 20(6):684-9 (2008).

(Continued)

Primary Examiner — Leigh C Maier
(74) Attorney, Agent, or Firm — Pabst Patent Group LLP

(57) ABSTRACT

Campylobacter are the commonest reported bacterial causes of gastroenteritis in the UK and industrialized worlds. This invention relates to a method of preventing or reducing the colonization of the gastrointestinal tract of an animal with Campylobacter. Accordingly, the present invention provides a method for disinfection of an animal comprising administering to said animal at least one compound that binds to MOMP or FlaA of Campylobacter in an effective amount to reduce the number of Campylobacter present in the gastrointestinal tract of said animal. The present invention also provides a method of preventing or reducing transmission of Campylobacter from one animal to another.

26 Claims, 17 Drawing Sheets

(56) References Cited

OTHER PUBLICATIONS

Ley, et al., "Human gut microbes associated with obesity", Nature, 444 (7122):1022-3 (2006).

Ley, et al., "Obesity alters gut microbial ecology", PNAS, 102(31):11070-5 (2005).

Madhavi, et al., "Helicobacter pylon SabA adhesin in persistent infection and chronic inflammation", Science, 297:573-8 (2002).

Mahdavi, et al., "A novel O-linked glycan modulates Campylobacter jejuni major outer membrane protein-mediated adhesion to human histo-blood group antigens and chicken colonization", Open Biol., 4:130202. doi: 10.1098/rsob.130202 (2014).

Menelauo, et al., "pH-Specific Synthetic Chemistry and Solution Studies in the Binary System of iron(III) with the r-Hydroxycarboxylate Substrate Quinic Acid:Potential Relevance to Iron Chemistry in Plant Fluids", Inorg Chem., 48:1844-56 (2009).

Misawa, et al., "Isolation of Campylobacter species from zoo animals and polymerase chain reaction-based randomamplified polymorphism DNA analysis", Vet Microbiol., 71:59-68 (2000).

Shevchenko, et al., "Mass spectrometric sequencing of proteins silver-stained polyacrylamide gels", Anal Chem., 68(5):850-8 (1996).

Turnbaugh, et al., "An obesity-associated gut microbiome with increased capacity for energy harvest", Nature, 444 (7122):1027-31 (2006).

Menelaou, et al., "Synthesis and characterization of two new isostructural ion (III)-quinates from aqueous solutions", J Agrolimentary Processes Tech., XII:281-4 (2006).

\* cited by examiner

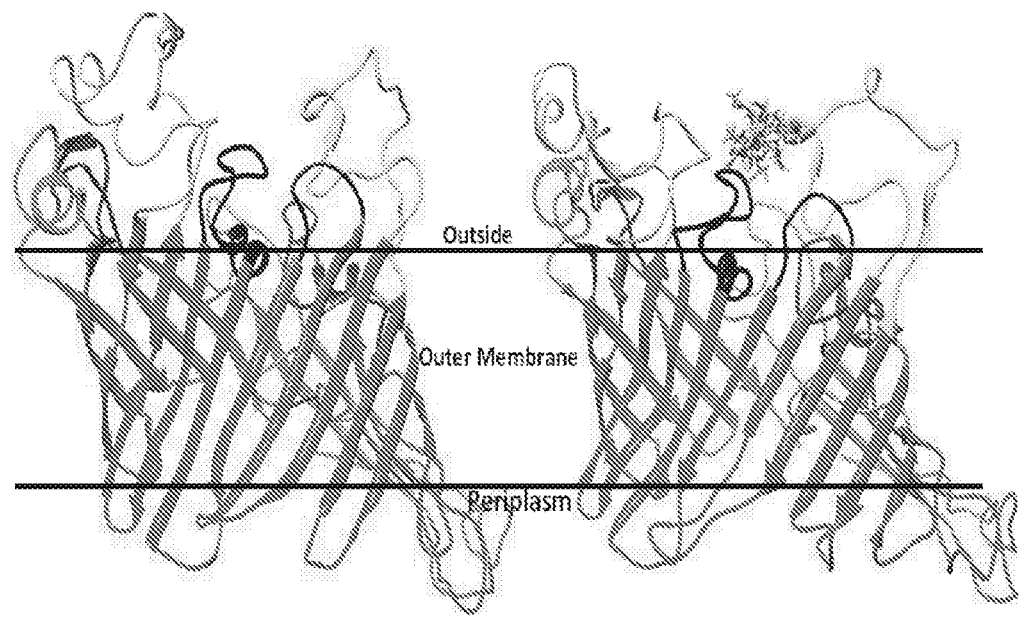
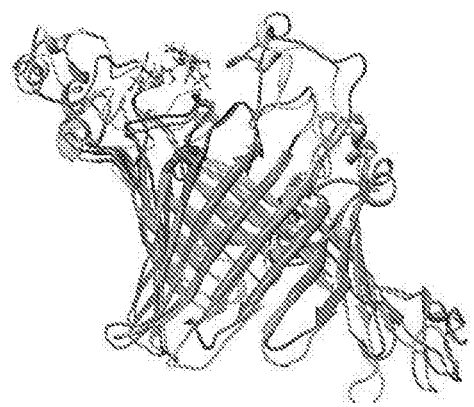
Fig. 4

| | | | |
|---|---|---|---|
| a | 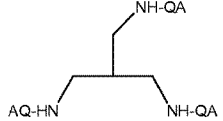 | N-[3-quinylamino-2-(quinylamino-methyl)-propyl]-quinamide | GATRIQ |
| b | 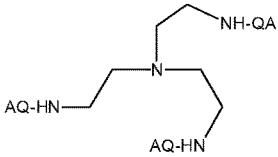 | N-{2-[Bis-(2-quinylamino-ethyl)-amino]-ethyl}-quinamide | ETTAQ |
| c | 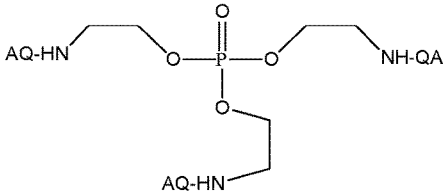 | Phosphoric acid tris-(2-quinylamino-ethyl) ester | PATQ |
| d | 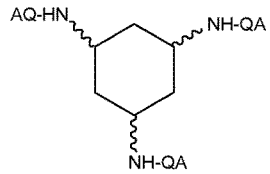 | N-(3,5-Bis-quinylamino-cyclohexyl)-quinamide | CH135TQ |
| e | 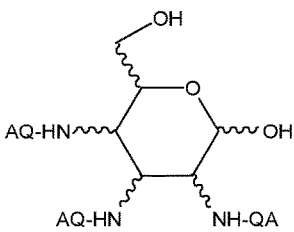 | N-(4,5-Bis-quinylamino-2-hydroxy-6-hydroxymethyl-tetrahydro-pyran-3-yl)-quinamide | PY234TQ |
| f | 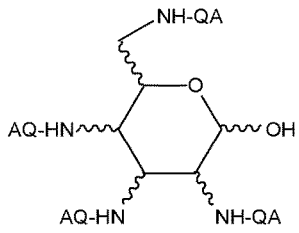 | N-(4,5-Bis-quinylamino-2-hydroxy-6-quinylaminomethyl-tetrahydro-pyran-3-yl)-quinamide | PY2346TETQ |

*Fig. 6*

Quinic acid | Quinate amide (1) | N,N-Bis-(2-aminoethyl)ethane-1,2-diamine (2) | N-(2-Dimethylamino-ethyl)acetamide (3)

REDUCTION OF GASTROINTESTINAL TRACT COLONISATION BY CAMPYLOBACTER

CROSS REFERENCE TO RELATED APPLICATIONS

This application is a 371 International Application No. PCT/GB2013/050367, filed Feb. 15, 2013, which claims the benefit of Great Britain Application GB 1202681.1 filed Feb. 16, 2012, and of Great Britain Application GB 1220158.8, filed Nov. 8, 2012.

REFERENCE TO SEQUENCE LISTING

The Sequence Listing submitted Aug. 21, 2012 as a text file named "AKESO_100_ST25.txt," created on Aug. 18, 2014, and having a size of 170,744 bytes is hereby incorporated by reference.

This invention relates to a method of preventing or reducing the colonisation of the gastrointestinal tract of an animal with *Campylobacter*. In particular, it relates to reduction or prevention of colonisation of the gastrointestinal tract of poultry with *Campylobacter*. It also relates to uses of compounds that bind to adhesins on the surface of *Campylobacter* to prevent the bacteria from adhering to the wall of the gastrointestinal tract of animals and to treat *Campylobacter* infection in humans and animals.

*Campylobacter* are the commonest reported bacterial causes of gastroenteritis in the UK and industrialized world. *Campylobacter jejuni* (*C. jejuni*) is responsible for about 90% of *Campylobacter* infections, the majority of the remainder being caused by *C. coli*. *Campylobacter* form part of the natural gastrointestinal flora of many birds and domestic animals, but chickens are thought to constitute the largest source of human infection. Infected chickens are asymptomatic despite harbouring up to $10^8$ colony forming units (cfu) per gram of intestinal content. Meat, in particular chicken meat, is often contaminated with intestinal contents including *Campylobacter* during slaughter. In humans, *Campylobacter* species cause diseases that vary in severity from mild watery diarrhea to bloody dysentery. In a small subgroup of patients, the acute phase disease is followed by serious sequelae, including Guillain-Barré syndrome and reactive arthritis.

It is therefore of great interest to provide methods for reducing and preventing the risk of contamination of meat with *Campylobacter* and therefore the risk of human infection with *Campylobacter*. It is also of interest to provide new treatments for human infection with *Campylobacter* (campylobacteriosis).

Accordingly, the present invention provides a method for disinfection of an animal comprising administering to said animal at least one compound that binds to MOMP or FlaA of *Campylobacter* in an effective amount to reduce the number of *Campylobacter* present in the gastrointestinal tract of said animal.

The present invention also provides a method for disinfection of an animal comprising administering to said animal at least one compound that binds to MOMP or FlaA of *Campylobacter* in an effective amount to prevent said *Campylobacter* from forming a biofilm in the gastrointestinal tract of said animal or to reduce the amount of biofilm formed by *Campylobacter* in the intestinal tract of said animal.

The present invention also provides a method for preventing or reducing transmission of *Campylobacter* infection from one animal to another, for example preventing or reducing spread of *Campylobacter* infection within a flock or herd of animals, for example preventing spread of *Campylobacter* infection within a flock of chickens; said method comprising administering to said animals, for example said herd or flock of animals, for example said flock of chickens, at least one compound that binds to MOMP or FlaA of *Campylobacter* in an effective amount to prevent said *Campylobacter* from forming a biofilm in the gastrointestinal tract of said animal or to reduce the amount of biofilm formed by *Campylobacter* in the intestinal tract of said animal.

The methods of the present invention may allow disinfection, prevention of biofilm formation and reduction of transmission of *Campylobacter* between animals by preventing or reducing adherence of *Campylobacter* of the gastrointestinal tract of said animals. This is advantageous because the fewer *Campylobacter* that are in the gastrointestinal tract of an animal at the time of slaughter, the lower the risk of contamination of meat from the animal with *Campylobacter*. The fewer *Campylobacter* that are in the gastrointestinal tract of an animal the lower the chance of the *Campylobacter* forming a biofilm in the gastrointestinal tract of the animal. The fewer *Campylobacter* that are in the gastrointestinal tract of an animal, the lower the chance that the *Campylobacter* will spread from one animal to another, for example within a herd or flock of animals.

Method of the present invention may be used to reduce the amount of colonisation of the gastrointestinal tract of any animal with *Campylobacter*. It is particularly advantageous to provide the compounds to animals that will be slaughtered for human consumption, such as, for example, cattle, sheep, pigs, goats, deer, fish, shellfish and poultry. Poultry includes birds that are used for human consumption such as chickens, geese, turkeys and ducks. It is particularly advantageous to use the compounds of the present invention to reduce or prevent colonisation of the gastrointestinal tract of poultry, in particular chickens, with *Campylobacter* because chickens are a leading source of human infection with *Campylobacter*.

*Campylobacter* are gram negative, spiral rod shaped bacteria with a single flagellum at one or both poles. They belong to the epsilon proteobacteria class and are closely related to *Helicobacter* and *Wolinella*. Although these species are related they have very different culture requirements and different hosts. *Campylobacter* species usually live in the gut of animals, in particular chickens while *Helicobacter* lives in the stomach of humans. Although fastidious in their culture requirements, *Campylobacter* species, particularly *C. jejuni* and *C. coli*, are important human pathogens, causing gastroenteritis of varying severity. Under normal circumstances gastroenteritis is self-limiting, but sequelae associated with campylobacteriosis such as Guillain-Barre syndrome are potentially life threatening. There are many different reservoirs for *Campylobacter* but the most significant is contaminated meat, particularly poultry.

The number of *Campylobacter* in the gastrointestinal tracts of animals may be reduced by the methods of the present invention. In one embodiment the number of colony forming units (cfu) of *Campylobacter* in the gastrointestinal tract of an animal treated with the compounds of the present invention may be reduced by 50%, by 60%, by 70%, by 80%, by 90% or by 100%. In one embodiment *Campylobacter* may be substantially eradicated from the gastrointestinal tract of animals treated by the method of the present invention.

10000 cfu of *Campylobacter* are enough for successful chicken colonization. 1000 cfu of *Campylobacter* are enough to infect a human and cause disease in a human. Therefore, an effective amount of a compound of the present invention is enough of the compound to reduce the number of *Campylobacter* in the gastrointestinal tract of an animal to a number that is unlikely to cause infection in humans. The number of cfu of *Campylobacter* that would be ingested by a human if they ate meat from an infected animal may be related to the number of *Campylobacter* in the gastrointestinal tract of the animal at the time of slaughter but also depends on other factors such as the amount of contamination of the meat with the contents of the gastrointestinal tract of the animal at the time of slaughter.

An effective amount of the compound of the present invention is enough of the compound to prevent colonisation of the gastrointestinal tract of the animal with *Campylobacter*.

In one embodiment the compounds of the present invention may make *Campylobacter* less virulent and less capable of infecting humans even if the total number of *Campylobacter* in the gastrointestinal tract does not decrease. In this embodiment administering a compound of the present invention to an animal may affect the metabolism of *Campylobacter* and make them less adaptive to environment so that they can not colonize the gastrointestinal tract and are less likely to be transmitted the other animals or to humans.

An effective amount of a compound provided to an animal should be enough to provide the required degree of reduction of *Campylobacter* colonisation. This may depend on the type of compound and/or the size of the animal. In one embodiment an effective amount of the compound may be 0.3 to 32 mg/day/kg bodyweight of the animal.

The method of the present invention preferably reduces colonisation of the gastrointestinal tract with *Campylobacter* species, for example *Campylobacter jejuni* or *Campylobacter Coli*.

This is advantageous because *Campylobacter jejuni* is the commonest reported bacterial cause of gastroenteritis in the UK and industrialized world. *Campylobacter jejuni* (*C. jejuni*) is responsible for about 90% of *Campylobacter* infections, the majority of the remainder being caused by *C. coli*. *Campylobacter* form part of the natural gastrointestinal flora of many birds and domestic animals and there is therefore a high risk of contamination of the carcasses of these animals when they are slaughtered.

The compound used in the method of the present invention is preferably a compound that blocks the interaction of MOMP or FlaA on the surface of *Campylobacter* with the cells of gastrointestinal tract. Preferably the compound binds to MOMP or FlaA and competitively or non-competitively inhibits the binding of MOMP or FlaA on the *Campylobacter* with the cells of the gastrointestinal tract. Preferably the compound used in the present invention may bind to MOMP on the surface of *Campylobacter jejuni*. Preferably the compound used in the method of the present invention specifically binds to at least one of amino acid residues $Arg^{352}$, $Lys^{278}$, $Lys^{385}$, $Asn^{258}$, $Leu^{290}$, $Tyr^{294}$, $Phe^{395}$ $Ile^{337}$, $Arg^{381}$, $Asp^{261}$ and $Ser^{397}$ of MOMP. In another embodiment the compound of the present invention reduces the interaction between at least one of amino acid residues $Arg^{352}$, $Lys^{278}$, $Lys^{385}$, $Asn^{258}$, $Leu^{290}$, $Tyr^{294}$, $Phe^{395}$ $Ile^{337}$, $Arg^{381}$, $Asp^{261}$ and $Ser^{397}$ of MOMP and the gastrointestinal tract of an animal.

In one embodiment the compound used in the method of the present invention may be natural human histo-blood group antigen or a synthetic human-histo blood group antigen.

Natural human histo blood group antigens are sugars that occur naturally on red blood cells of humans. They are also expressed on the surface of epithelial cells, such as the cells lining the gastrointestinal tract and can be secreted in body fluids such as saliva and breast milk.

The common human histo blood group antigens (BgAgs) consist of a complex and polymorphic group of carbohydrates expressed on the surface layer of erythrocytes, as well as endothelial and many epithelial cells and secretions. Subtle differences in their structures cause major differences in antigenicity. Their common denominators are the types I and II core glycoconjugates, which are fucosylated in the bone marrow by H-(fucosyl) transferases into H-I and H-II respectively, before being added to the surface of erythrocytes. (11). The fucosylated glycans are the direct substrates for further glycosylation reactions that give rise to the epitopes for the A, B and Lewis blood group antigens. The ABO (or ABH) and Lewis BgAgs have been epidermiologically associated with susceptibility to several infectious agents.

Human blood group antigens (BgAgs) include H-I antigen, H-II antigen Lewis antigen $Le^b$ and $Le^x$ and $Le^y$.

Human histo-blood group antigens, binding to the adherins, for example MOMP or FlaA, on *Campylobacter* prevent or reduce the ability of the *Campylobacter* to adhere to the epithelial cells of the gastrointestinal tract.

A synthetic human histo blood group antigen may be a molecule with the same chemical structure as a natural human histo blood group antigen but it is made outside of the human body, for example it may be made synthetically from suitable reagents or may be made in other organisms, such as bacteria, fungi or eukaryotes and expressed transgenically. In another embodiment a synthetic human histo blood group antigen may be a molecule that binds to the same part of MOMP or FlaA as a natural human histo blood group antigen. A synthetic human histo blood group antigen may be a sugar or a glycoprotein or a glycolypid. The synthetic human histo blood group antigen may be purified using one or more purification steps, for example chromatography steps, before being used in the method of the present invention.

A synthetic human histo-blood group antigen may be used to inhibit the binding or adhesion between MOMP and/or flaA and epithelial cells. It may bind to MOMP and/or FlaA and prevent or reduces MOMP or FlaA adhesion to epithelial cells and reduce or prevent colonisation of the gastrointestinal tract of an animal with *Campylobacter*.

A synthetic human histo-blood group antigen may be a sugar, for example a saccharide having the same structure as a natural human histo-blood group antigen such as for example H-I antigen, H-II antigen, Lewis antigen, $Le^b$ $Le^x$ or $Le^y$.

The compound used in the method of the present invention may be a compound that has a structure that is different from a natural human histo-blood group antigen but that adheres to MOMP and/or FlaA and prevents or reduces MOMP or FlaA adhesion to epithelial cells and reduces or prevents colonisation of the gastrointestinal tract with *Campylobacter*. The compound may be a sugar or an oligosaccharide.

Preferably the compound is a molecule that adheres to MOMP. Suitably the compound is a molecule that can interact with loop 7 of MOMP in the glycosylated or unglycosylated form.

The compound used in the method of the present invention may be ferric quinate. The compound used in the method of the present invention may have one of the following structures:

a)

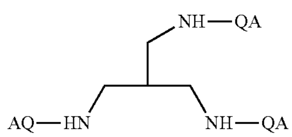

b)

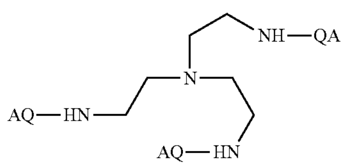

c)

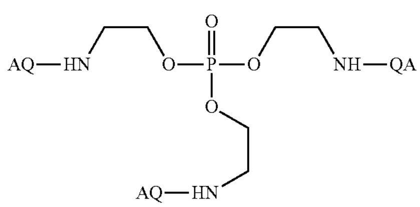

d)

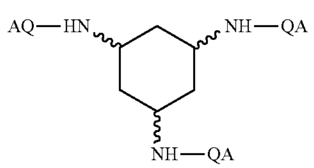

e)

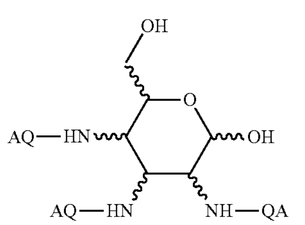

f)

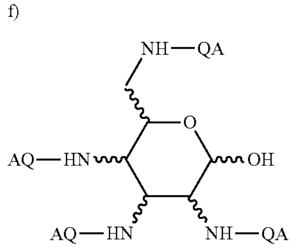

-continued g)

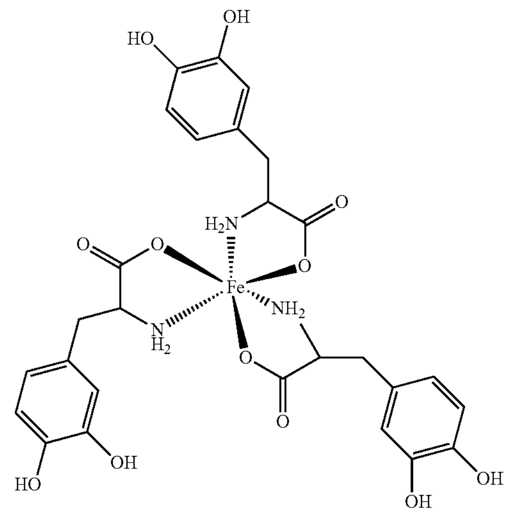

complex of DOPA with Fe III (3,4 dihydroxyphenylalanine)

h)

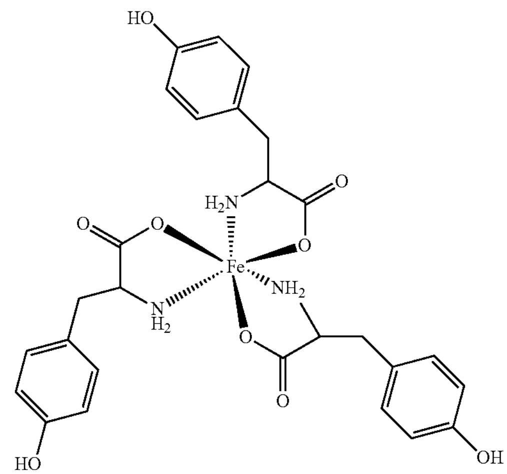

complex of tyrosine with Fe III

The compound used in the method of the present invention may have a structure similar to that of Ferric Quinnate. The compound used in the present invention may be a compound with a structure similar to the structure of a human histo blood group antigen.

The compound used in the method of the present invention may be administered orally. This is advantageous because it is easy to administer compounds orally to animals. Oral administration is also a preferred method of administering a compound to ensure that it reaches the gastrointestinal tract.

Preferably the compound may be administered in an animal's feed or drinking water.

In the method of the present invention the compound may be administered to the animal at any time during its lifetime. In one embodiment the compound is administered to the animal at least once a day for a period of time before slaughter of the animal. For example the compound may be administered to the animal for between 1 and 10 days, preferably for between 1 and 8 days, between 1 and 6 days, between 1 and 4 days, before slaughter or for 2 or 1 days. In one embodiment a single dose of the compound may be administered to the animal between 1 and 4 days before slaughter. In one embodiment the compound may be administered to the animal every day for 3 days, 4 days or 5 days before slaughter. Chickens are often colonized by *Campylobacter* between 7 and 10 days before slaughter. Therefore in one embodiment the compound may be administered to a chicken less than 10 days before slaughter to disinfect the chicken and reduce colonisation of the gastrointestinal tract of the chicken before slaughter. In another embodiment the compound of the present invention may be administered to an animal before colonisation of the gastrointestinal tract of the animal with *Campylobacter* in order to prevent colonisation of the gastrointestinal tract of the animal with *Campylobacter*. In one embodiment the compound of the present invention is administered to a chicken more than 10 days before slaughter to prevent transmission of *Campylobacter* within a flock of chickens.

It is advantageous to administer the compound to the animal a short time before slaughter because the animal the amount of *Campylobacter* in the gastrointestinal tract of the animal is reduced at the time of slaughter so that there is a lower risk of contamination of the carcass with *Campylobacter*.

In one embodiment of the present invention the compound may be administered to an animal at a dosage of 0.3-32 mg/day/kilo as a solution having a range of concentration from 34-340 μM (0.02-0.2 g/L). A concentration of 0.2 g/L has an effect on colonization during the first three days post-infection and also on the binding of *Campylobacter* to blood group antigens may be reduced by 60%. In another embodiment the compound may be administered at a concentration of 2 g/L, which may prevent *Campylobacter* colonisation of the gastrointestinal tract of the animal and/or reduce the number of *Campylobacter* in the gastrointestinal tract of the animal to substantially zero.

In another embodiment the present invention provides a method for reducing the amount of *Campylobacter* in meat comprising the steps of: Providing an animal with a compound as defined in any one of the preceding claims; and preparing a meat product from the animal. The animal may be any type of animal, preferably a poultry bird, preferably a chicken.

In another embodiment the present invention provides a method for identifying a compound for use in disinfection of animals, preventing or reducing adhesion of *Campylobacter* to the gastrointestinal tract or treatment of *Campylobacter* infection in humans or animals, said method comprising the steps of:
a) providing a simulation of MOMP or glycosylated MOMP;
b) selecting a candidate molecule that fits within the cavity between loops 4 and 7 of MOMP or selecting a candidate molecule which interacts with at least one of amino acid residues $Arg^{352}$, $Lys^{278}$, $Lys^{385}$, $Asn^{258}$, $Leu^{290}$, $Tyr^{294}$, $Phe^{395}$ $Ile^{337}$, $Arg^{381}$, $Asp^{261}$ and $Ser^{397}$ of MOMP.

Compounds may be selected by docking them into an in silico model of MOMP to find a molecule that fits into the binding site of MOMP where the human histo blood group antigen binds with MOMP.

Preferably the compound is a molecule that can interact with at least one of amino acid residues $Arg^{352}$, $Lys^{278}$, $Lys^{385}$, $Asn^{258}$ $Leu^{290}$, $Tyr^{294}$, $Phe^{395}$ $Ile^{337}$, $Arg^{381}$, $Asp^{261}$ and $Ser^{397}$ of MOMP.

Preferably the compound is a molecule that can interact with at least one or more of amino acid residues $Arg^{352}$, $Lys^{278}$ and $Lys^{385}$ of MOMP or at least one or more of residues $Asn^{258}$ and $Lys^{278}$ or at least the residues 352 and 385 of MOMP. The compound may interact with at least residues $Leu^{290}$, $Tyr^{294}$, $Phe^{395}$ and/or $Ile^{337}$ of MOMP or at least one or more of residues $Lys^{278}$, $Arg^{352}$ and $Arg^{381}$ of MOMP or at least one of $Asp^{261}$ and $Ser^{397}$ of MOMP.

The major contributors in the interaction of glycosylated MOMP with $Le^b$ are residues $Arg^{352,381}$ and $Lys^{278}$, whereas only residues 352 and 278 are involved in the interaction of non-glycosylated MOMP with $Le^b$. Residues $Arg^{352,381}$ are conserved in all sequences examined whilst residue $Lys^{278}$ is semi-conserved and is replaced by Arg in some strains. The molecular properties of this amino acid suggests it would be able to mediate BgAg binding through hydrogen bond formation in a similar fashion to residues $Arg^{352,381}$.

The present inventors have constructed an in silico model of glycosylated MOMP. The in silico model of MOMP may be used to identify amino acid residues that are in contact with various human histo-blood group antigens when they bind to MOMP. This in silico model allows the conformational changes that take place in MOMP when it is glycosylated to be studied. This can be advantageous because it allows selection of further compounds that could interact with MOMP, in particular compounds that can bind to the amino acids that have been identified. These compounds can then be tested in vivo or in vitro to check whether they bind to MOMP protein.

The adhesion of *Campylobacter*, in particular *Campylobacter jejuni* (*C. jejuni*) to human histo-blood group antigens is via the major subunit protein of the flagella (flaA) and the major outer membrane protein (MOMP). MOMP was shown to be glycosylated at $Threonine^{268}$. This glycosylation was shown by in silico modelling techniques to have a notable effect on the conformation of MOMP and to increase adhesion of MOMP to human histo-blood group antigens.

Residues of MOMP that have been identified as binding to various natural human histo-blood group antigens include $Arg^{352}$, $Lys^{278}$, $Lys^{385}$, $Asn^{258}$, $Leu^{290}$, $Tyr^{294}$, $Phe^{395}$ $Ile^{337}$, $Arg^{381}$, $Asp^{261}$ and $Ser^{397}$ of MOMP. It is advantageous to select candidate molecules that may be used in the present invention because they bind to MOMP by interacting with one or more of these residues in the structure of MOMP.

Once compounds have been selected in silico, they may made and tested to measure the binding to MOMP protein in vitro or in vivo. A quantity of the selected compound can be prepared for use in the methods of the present invention.

Compounds that are useful in the method of the present invention may be included in animal feed, as a feed ingredient or as a feed supplement. The animal feed, feed ingredient or feed supplement may be suitable for any animal, in particular animals that are to be slaughtered for human consumption, preferably poultry, more preferably chickens.

Compounds that are useful in the methods of the present invention may be provided to an animal in liquid or solid form or as a powder. They may be included as an ingredient in feed or animal food or as an ingredient in a feed or food supplement. In one embodiment the compounds are provided to chickens in chicken feed or as a feed ingredient mixed with chicken feed.

A feed may be a food intended for or suitable for consumption by animals. A food or a foodstuff may be a food that is intended or suitable for consumption by humans.

The present invention provides a method of disinfecting a foodstuff or a food comprising administering a compound as defined in any one of the preceding claims in an effective amount to the foodstuff to reduce the amount of *Campylobacter* in the foodstuff.

This is advantageous because it reduces the risk of infection with *Campylobacter* of humans who consume the foodstuff.

A foodstuff or a food may be for human consumption, in particular the food may be a meat product, for example a fresh meat product, a processed meat product, a chilled meat product, a frozen meat product or a cooked meat product. The meat product may be, for example a beef, lamb, pork, duck, chicken, goose, turkey, rabbit, fish or shellfish meat product. Preferably the meat product may be a poultry meat product, more preferably a chicken meat product.

The present invention also provides a compound as defined in the present invention for use in the prophylaxis or treatment of *Campylobacter* infection in humans. A compound as defined in the present invention may be used in the manufacture of a medicament for the prophylaxis or treatment of *Campylobacter* infection in humans.

The compound may be provided to humans to prevent or treat infection of humans with *Campylobacter* (campylobacteriosos). This is advantageous because the compounds prevent or reduce adhesion of *Campylobacter* to the epithelial cells in the gastrointestinal tract. This may prevent or reduce infection with *Campylobacter* because *Campylobacter* adheres to cells in the human gastrointestinal tract by docking onto human histo-blood group antigens that are expressed on the cells of the gastrointestinal tract. The compounds may compete with natural human histo-blood group antigens that are on the epithelial cells for binding of MOMP and FlaA and therefore reduce the amount of binding of *Campylobacter* to the cells.

The in silico model of MOMP may be used to develop or refine a vaccine against *Campylobacter* for use in humans.

The in silico model of MOMP may be used to develop or refine a vaccine against *Campylobacter* for use in birds, preferably poultry, more preferably chickens.

Subunit (or killed) vaccines have a number of advantages over live vaccines, including safety and ease of production, storage and distribution. To date only limited success has been achieved with subunit vaccines administered orally. The reason for this is assumed to be the lack of oral delivery to the appropriate site for development of immune-mediated protection. The assumption is that the most appropriate site would be the intestinal mucosa. Such delivery requires the presentation of antigen with a mucosal adjuvant. Currently there are no known mucosal adjuvants for birds.

Recently a number of delivery systems have been developed for mammalian mucosal vaccination regimes. One such system utilises a non-ionic, hydrophilic immunomodulator, Pluronic block copolymer F127, and the polysaccharide chitosan formulated into microspheres (Lee, Da Silva et al. 2008). Chitosan is used in a number of biomedical applications because of its bioavailability, biocompatibility, biodegradability, high charge density and non-toxicity. In addition this material has been shown to weaken the tight junctions of epithelial cell layers allowing the uptake of antigen and to reduce the rate of mucociliary clearance reducing antigen removal. Although this material appeared to be valuable in the development of mammalian vaccines and drug delivery systems it had not been tested in birds.

The microspheres were made using an ionic gelation process with tripolyphosphate (TPP). Briefly, 0.25% chitosan in 2% acetic acid was added drop-wise to 15 w/v % TPP under magnetic stirring. The mixture was sonicated and the MS beads removed from the TPP solution by centrifugation, washed with distilled water and resuspended in PBS. The antigens were then loaded onto the beads by co-incubating overnight at 37° C. After incubation, the suspension was centrifuged to separate the beads from unloaded antigens (MOMP/FlaA). The levels of antigen uptake were determined by protein concentration assays of protein solutions pre- and post-loading.

The present invention provides a method of treating or preventing *Campylobacter* infection in humans comprising administering to the human an effective amount of a compound as defined in any one of the preceding claims.

The present invention provides a kit comprising:
a) at least one compound as described in the present invention and optionally instructions for using the kit.

There now follows by way of example only a detailed description of the present invention with reference to the accompanying drawings, in which;

FIG. 1 shows the competitive effect of the soluble glycoconjugates, i.e. H-II, Le$^b$ or Le$^y$ on attachment of strain NCTC11168 to a series of BgAs. A) An ELISA plate was coated with a selection of BgAgs. Specific binding was calculated by subtracting the BSA (negative control) values from the BgAg absorbance. Binding of strain NCTC11168 to BgAgs was inhibited significantly (p<0.05) by pre-incubation of cells with soluble glycoconjugates prior to adding them to the ELISA plate. Error bars; mean of triplicate values±SEM, number of repeating experiments was 3. Each group of bars, from left to right, NCTC11168, NCTC11168-H-II, NCTC11168-Leb, NCTC11168-Ley.

B) Identification of BgAg-binding proteins from strain NCTC11168 by using Re-Tagging method. Two proteins were identified at sizes of 45 and 59 kDa, corresponding to MOMP and FlaA, respectively.

FIG. 2 shows A) Inhibition of binding of strain NCTC11168 to H-II glycoconjugate in the absence of an inhibitor (non-treated, NT) and in the presence of purified MOMP of Cj-281 (MOMP(−)), low binder strain, S3—Table 1). Purified MOMP from NCTC11168 (MOMP(+)), and pre-incubation of NCTC11168 bacterial cells with H-II glycoconjugate (H-II). Pre-treatment of all examined MOMP and H-II had significantly reduced (p<0.001, ***) the bacterial binding to H-II antigen. In contrast, MOMP(−) had a lower effect compared with H-II or MOMP(+) due to the lower affinity for the H-II antigen. B) ELISA plate was coated with a selection of BgAgs. Specific binding was calculated by subtracting the BSA (negative control) values from the BgAg absorbance at 405 nm. Strain NCTC11168 and Cj-266 (high binder strain, S3—Table 1), and corresponding ΔflaA mutants, have been examined for binding to Le$^b$, H-II, H-I, Le$^x$ and Le$^a$. t-test confirmed the reduction in binding seen with mutants are significant (Le$^b$; p=2.5E-05, H-II; p=0.012, H-I; p=0.001, Le$^x$; p=0.029 and Le$^a$; p=0.000) in strain NCTC11168. However, Cj-266ΔflaA mutation had no effect on binding, which indicates the binding capacity was compensated by MOMP protein. Each group of bars from left to right: NCTC11168, 11168-ΔflaA, Cj-266, Cj-266ΔflaA. C) A double mutant (DM) of ΔflaA and single substitution of glycosylation site in MOMP protein (Thr$^{268}$ was substituted with Gly) was constructed in both strain NCTC11168 and Cj-266, and the binding to Le$^b$ H-I and H-II was examined. The binding was significantly reduced in NCTC11168-MOMP$^{T/G}$ but the reduced binding was not significant in Cj-266-MOMP$^{T/G}$. Although, t-test confirmed the reduction in binding seen with NCTC11168-DM and Cj-266-DM the mutants are significant (p<0.05). Each group of bars from left to right: Leb, H-II, H-1.

FIG. 3 shows an overview of the mass spectrometry analysis by LC-MS/MS for both protein identification and glycosylated peptide characterization. A) Base peak chromatogram: Tryptic peptides are loaded on an on-line coupled C18 column and eluted into the mass spectrometer for analysis. B and C) MS precursor scan of the doubly charged glycosylated peptide at m/z 978.91 C) CID-MS/MS spectrum of the selected ion. D) Detection of glycan constituent of purified MOMP from different strains using biotinylated labeled lectins. GSL II: *Griffonia* (*Bandeiraea*) *simplicifolia* lectin II, DSL: *Datura Stramonium* lectin, ECL: *Erythrina cristagalli* lectin, LEL: *Lycopersicon esculentum* (tomato) lectin, STL: *Solanum tuberosum* (potato) lectin, VVA: *Vicia villosa* agglutinin and Jacalin: *Artocarpus integrifolia* lectin.

Jacalin lectin showed significant binding to NCTC11168 purified MOMP than the other used lectins. Jacalin lectin specifically recognizes Galβ1-3GalNAcα$_1$-Ser/Thr (T-antigen) and/or GalNAc. E) Further analysis was revealed by using an antibody against the T-antigen to confirm Jacalin specificity. MOMP(s) purified form strains 255, 281 (low binder clinical isolates) and MOMP$^{T/G}$ didn't reveal significant binding to either Jacalin lectin or anti-T antigen compared with MOMP purified from strain NCTC11168 wild type. Error bars=mean of triplicate values±SED, No 2. Two independent experiments (P value). For each pair of bars: left hand bar—Jacalin lectin, right hand bar—Anti-Tantigen.

FIG. 4 shows a representation of MOMP (A, right) and glycosylated MOMP (A, left) in the approximate boundaries of the hydrophobic part of the outer membrane (OM). B), the superimposed lowest energy structure of MOMP (green) on the lowest energy structure of glycosylated MOMP (magenta) with RMSD of 1.291. Loops are shown in colours; 13 strands are green, L1 (residues 41-60, red), L2 (residues 87-109, magenta), L3 (residues 128-147, orange), L4 (residues 169-200 yellow) L5 (residues 227-233, black), L6 (residues 256-274, blue), L7 (residues 296-333, gray), L8 (residues 360-379, cyan) and L9 (residues 399-414, purple).

FIG. 5 shows a stereo cartoon of the MOMP backbone viewed from the extracellular side: β strands are green, L1 (red), L2 (magenta), L3 (orange), L4 (yellow) L5 (black) (L5), L6 (blue), L7 (gray), L8 (cyan) and L9 (purple) and its side view. The conformational changes in the glycosylate group induced by introduction of the ligands into the cavity of glycosylated MOMP. The complexes with Le$^b$ (A) and H-II (D). In addition, hydrogen bonds shown in light blue involved in the interactions of MOMP (B and E) and its glycolysated form (C and F) with Le$^b$ and H-II respectively in their active sites.

FIG. 6 shows examples of compounds that can be used in the present invention.

FIG. 7 shows the effect of a series of histo blood group antigens on biofilm formation. Comparison of biofilm formation between NCTC11168-WT, and corresponding mutants, ΔflaA and MOMP-T/G in presence and absence of free sugars. A) The most significant decrease in biofilm formation is seen in wild type strain compared to the mutants. However, the biofilm formation of MOMP268T/G strain is comparable to ΔflaA, which indicate that O-glycosylation of MOMP also play important role for this formation. For each group of bars from left to right: NCTC11168, NCTC11168 (sugar), MOMP-T/G, MOMP-T/G(sugar). B) Similar re-sults were observed except for core-II, other examined sugars significantly reduced the biofilm formation. For each group of bars from left to right: NCTC11168, NCTC11168(sugar), Δfla A, Δfla A (sugar).

FIG. 8 shows the lowest energy structure of MOMP from MD simulation with stereo cartoon of the MOMP backbone viewed from the extracellular side. MOMP forms hydrophilic channels through the outer membrane. The folding of β-barrel OMPs promotes trimer assembly and integration of the channel into the outer membrane. Moreover, two-dimensional crystallographic analysis showed that MOMP is structurally related to the family of trimeric bacterial porins.

CD spectroscopy analysis also demonstrated that the folded monomer mainly com-prised β-sheet secondary structure, in agreement with the so called β-barrel structure of porins. MOMP folded monomers are able to form channels in artificial lipid bilayers with the same conductance properties as monomers embedded into trimers, which suggests that the folded monomer is the functional unit of the MOMP porin.

Figure 17:
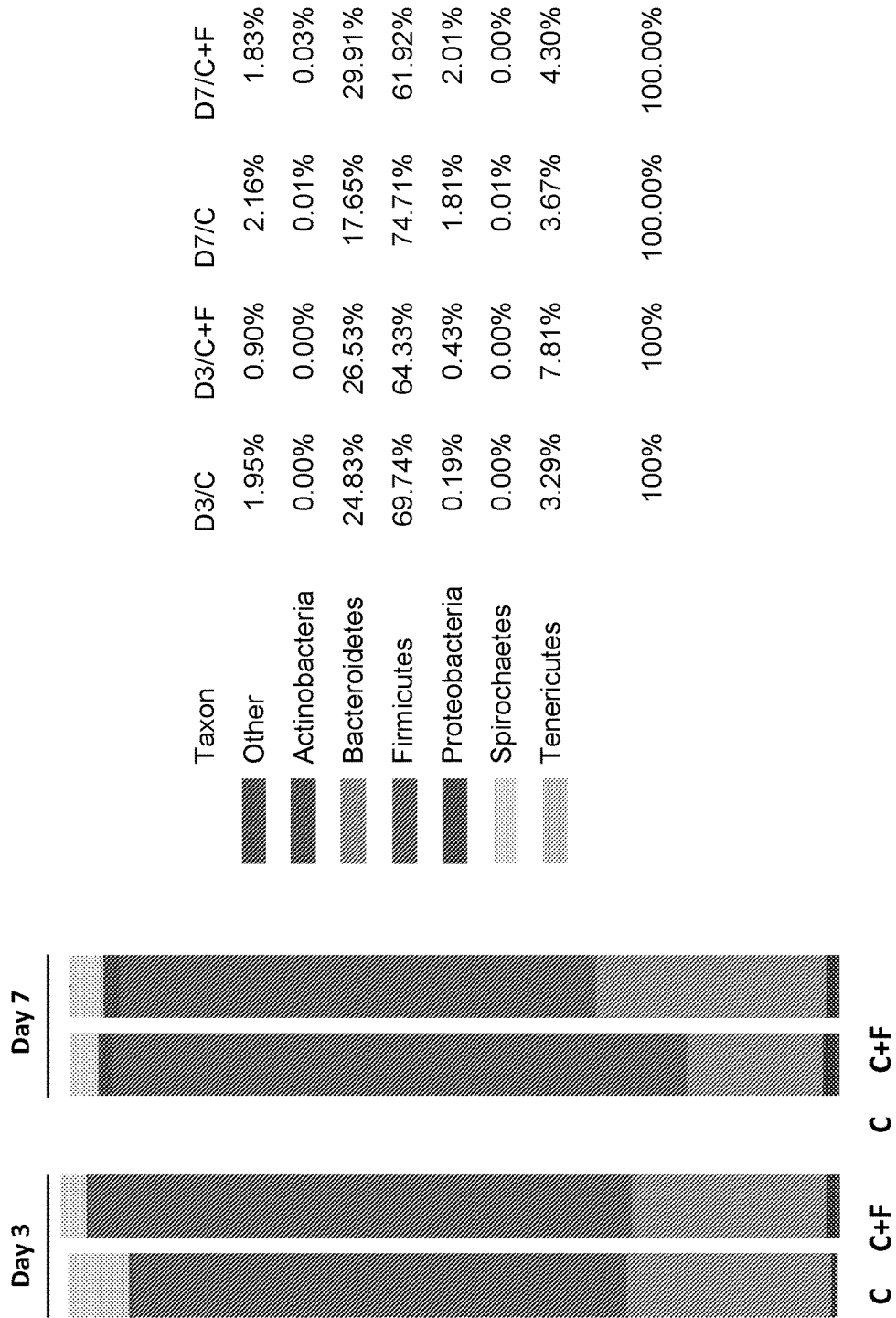

FIG. 17 shows metagenomic analysis of population treated with FeQ Phylum level. 1—Ley R, Bäckhed F, Turnbaugh P, Lozupone C, Knight R, Gordon J (2005). "Obesity alters gut microbial ecology". Proc Natl Acad Sci USA 102 (31): 11070-5. doi:10.1073/pnas.0504978102. PMC 1176910. PMID 16033867

2—Ley R, Turnbaugh P, Klein S, Gordon J (2006). "Microbial ecology: human gut microbes associated with obesity". Nature 444 (7122): 1022-3. doi:10.1038/4441022a. PMID 17183309.

3—Turnbaugh P, Ley R, Mahowald M, Magrini V, Mardis E, Gordon J (2006). "An obesity-associated gut microbiome with increased capacity for energy harvest". Nature 444 (7122): 1027-31. doi:10.1038/nature05414. PMID 17183312.

*Campylobacter jejuni* is an important cause of human food-borne gastroenteritis. Despite the high prevalence and medical importance of *C. jejuni* infection, fundamental aspects of pathogenesis remain poorly understood, in particular the detailed molecular interactions between host and pathogen. Human histo-blood group antigens (BgAgs) are often targeted by mucosal organisms as levers for adherence prior to invasion. Using a retagging approach, the corresponding surface-exposed BgAgs-binding adhesins of *C. jejuni* were identified as the major subunit protein of the flagella (FlaA) and the major outer membrane protein (MOMP). O-glycosylation of FlaA has previously been reported, and is required for filament assembly and for modulating flagella functionality. Purified MOMP like FlaA was O-glycosylated. The O-glycosylation was localised to Thr$^{268}$ and suggested as Gal$_{\beta1-3}$-(GalNAc)$_3$-α1-Thr$^{268}$. Site-directed substitution of MOMP Thr$^{268}$/Gly led to a significant reduction in binding to BgAgs. Furthermore, molecular dynamics (MD) simulation modelling techniques suggested that O-glycosylation of MOMP has a notable effect on the conformation of the protein.

Thus, *C. jejuni* uses O-glycosylation of surface-exposed proteins to modulate the conformation and binding capability.

Prevention and treatment of human infection with *Campylobacter* and its consequences are hampered by a poor understanding of the detailed molecular interaction between the host and the pathogen.

Studies by the present inventors have shown that *C. jejuni* specifically bind all human BgAgs, and identified the bacterial ligands responsible for binding. These are the flagellin protein FlaA and the major outer membrane protein MOMP.

The present studies have also found that MOMP is O-glycosylated, and shares a common BgAg binding site with FlaA, which has already been shown to be O-glycosylated. Glycosylation of MOMP causes it to undergo conformational changes which alters its affinity for binding of, and hence recognition of, BgAgs compared with unglycosylated MOMP protein. Conformational MOMP epitopes are important in host immunity, and variation in surface-exposed regions probably occurs as a result of positive immune selection during infection. Identification of the protein glycosylation profile of *C. jejuni*, in the outer membrane is helpful in understanding the diverse pathogenicity of *C. jejuni* strains among different hosts.

The present studies have created an in silico model of glycosylated MOMP, which have been used to identify the amino acids which mediate the bacterial binding to BgAgs. The model and the amino acids that are essential for binding to BgAgs may be used to identify candidate drug targets. The model may also be used to predict which molecules will bind to MOMP and can reduce the adhesion of the *Campylobacter* carrying MOMP to cell walls.

The present studies have found that BgAgs can inhibit bacterial adhesion and biofilm formation and have identified molecules that can be used (a) for treatment of humans suffering from Campylobacteriosis; (b) to prevent colonisation of chickens with *Campylobacter* ssp; and (c) to eliminate chicken colonisation in infected flocks.

Previous attempts to reduce the risk of human infection with *Campylobacter* ssp involved the use of vaccines employing nucleic acids encoding *Campylobacter* proteins, in particular flagellin (US200712049553).

This is completely different from the approach of the present invention which uses specific compounds to block the ligand binding site of the *Campylobacter* and hence inhibit *Campylobacter* adherence and colonisation in the chicken gastrointestinal tract. Compounds that are mimetics or synthetic human histo-blood group antigens and synthetic sugars such as Ferric Quinate (Fe-Q) may be used in the present invention.

EXAMPLES

*C. jejuni* Binds a Wide Range of Human BgAgs

To determine the range and specificity of BgAgs that bind *C. jejuni*, Core-I, Core-II, Le$^b$, Le$^x$, and Le$^y$ were immobilised in specialised 96-well ELISA plates and incubated with log-phase digoxigenin (Dig)-labelled *C. jejuni* strain NCTC11168. The strain bound to all the examined BgAgs, the degree varying only marginally between BgAgs (S1—Fig.).

Blood group antigens were obtained from IsoSep (Sweden). The lab strain (ATCC11168) was obtained from ATCC bank and the clinical strains from a collection belong to Prof. Julian M. Ketley (Department of Genetics, University of Leicester, Leicester LE1 7RH, UK).

Figure 1:
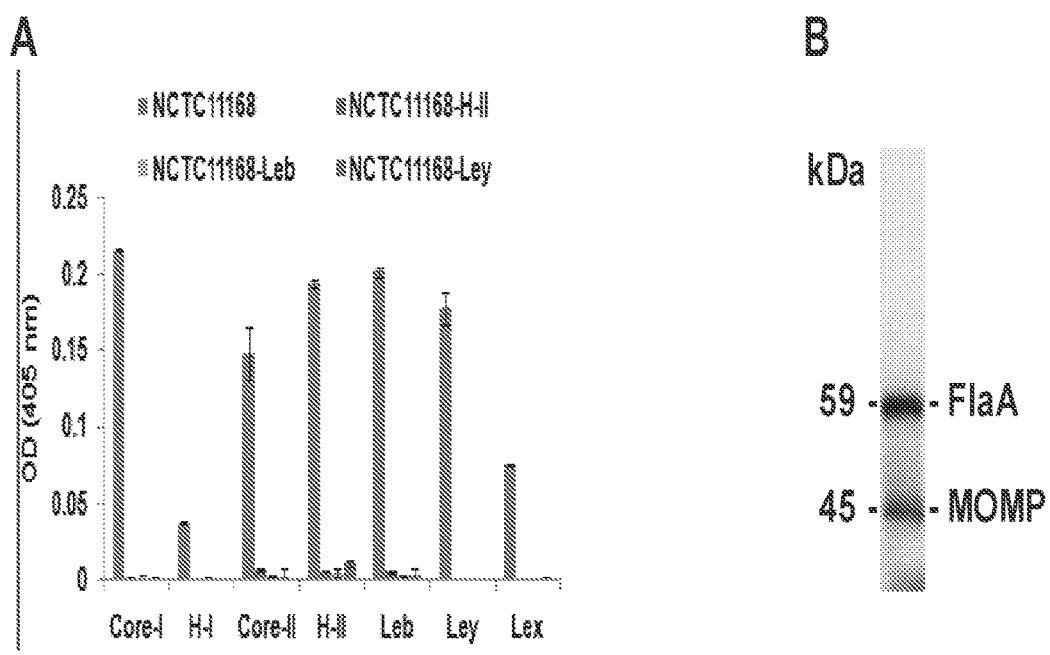

Pre-incubation of bacteria or coated plates with soluble BgAgs inhibited the binding, confirming specificity (FIG. 1A). In addition, adhesion assays by co-culturing *C. jejuni* strain NCTC11168 and Caco-II cells was carried out. Soluble H-II caused significant reduction in bacterial binding to the host cells (S2—Fig.). In addition, the same range of immobilized BgAgs was used to test the ability of 39 clinical isolates of *C. jejuni*. All *C. jejuni* isolates bound to all examined BgAgs, albeit to a variable degree (S3—Table). Correlation analysis between each sugar and principal component analysis was performed. It enables a visualization of the correlations—the structurally closer (S4—Table) the sugars are to each other, the more similar they are in terms of binding capacity (S4—Fig.).

The high degree of specificity by *H. pylori* BgAg-binding adhesions is in contrast to our findings with *C. jejuni*, which appears to bind to a wide range of related antigens. This may reflect the fact that *H. pylori* has a very restricted host range (infecting only humans), whereas *C. jejuni* is able to establish infection in a wide range of birds and mammals and may have gained an evolutionary advantage by broadening its specificity and maximising its survival in different hosts.

*C. jejuni* FlaA and MOMP Mediate the Binding to a Wide Range of Human BgAgs.

For identification and purification of BgAgs-binding bacterial adhesins, a retagging technique was used. Two generated protein bands in FIG. 1B identified by mass spectrometry as the major outer-membrane protein (MOMP, 45 kDa) and FlaA (the major flagella component, 59 kDa), respectively. The *C. jejuni* MOMP is a multi-functional porin and is essential for bacterial survival; it is predicted to comprise outer membrane-spanning beta stands separating periplasmic and surface-exposed loops. That it is encoded by the porA gene which is extremely genetically diverse and the variability of the porA surface loops provides evidence that immune selection strongly influences the diversity of this protein. Interestingly, the greatest variation in both putative amino acid sequence and length was formed in loop 4.

Figure 2:
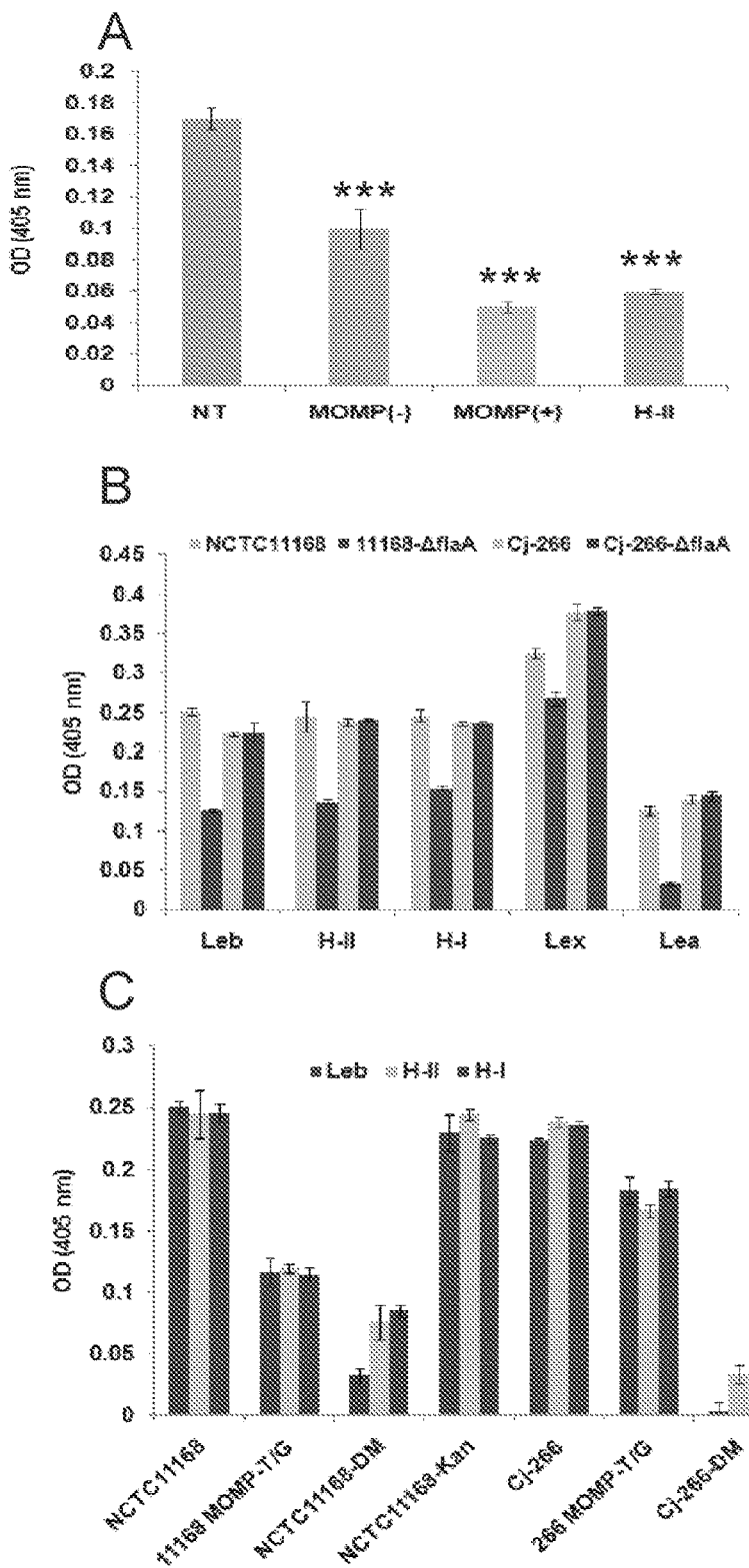

MOMP was purified under native conditions from strain NCTC11168 and inhibition ELISA and confocal experiments showed that both purified MOMP and H-II significantly inhibited binding of NCTC11168 to H-II antigen (FIG. 2A). Deletion mutant of ΔflaA in strains NCTC11168 and Cj-266 (a clinical isolate, S3—Table) were constructed. This had significantly reduced the binding capacity to all examined BgAgs except for Le$^x$ in strain NCTC11168 (FIG. 2B). By contrast, ΔflaA deletion in strain Cj-266 didn't exhibit reduced binding to BgAgs (FIG. 2B), which indicated that MOMP per se is sufficient for adherence to BgAgs.

Invasive properties could be partially restored by centrifugation of the mutants onto the tissue culture cells, indicating that motility is a major, but not the only, factor involved. Here, we identified the corresponding *C. jejuni* adhesins, which mediate the bacterial binding to BgAgs.

Ability of MOMP268T/G to Colonise Chicks

Figure 10:
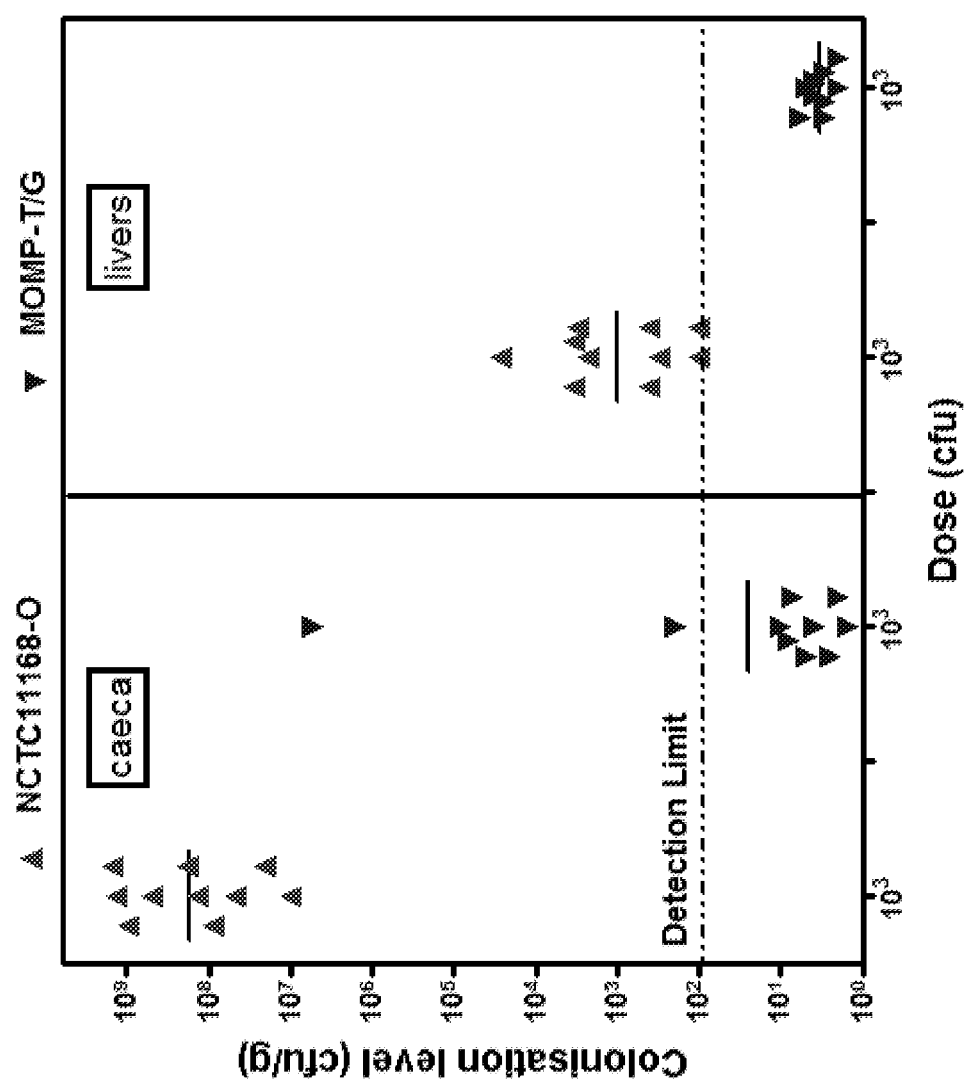
FIG. 10 shows colonisation levels of chicks challenged with wild-type *campylobacter* strain NCT11168-0 or mutant *campylobacter* strain MOMP$^{268T/G}$.
Figure 11:
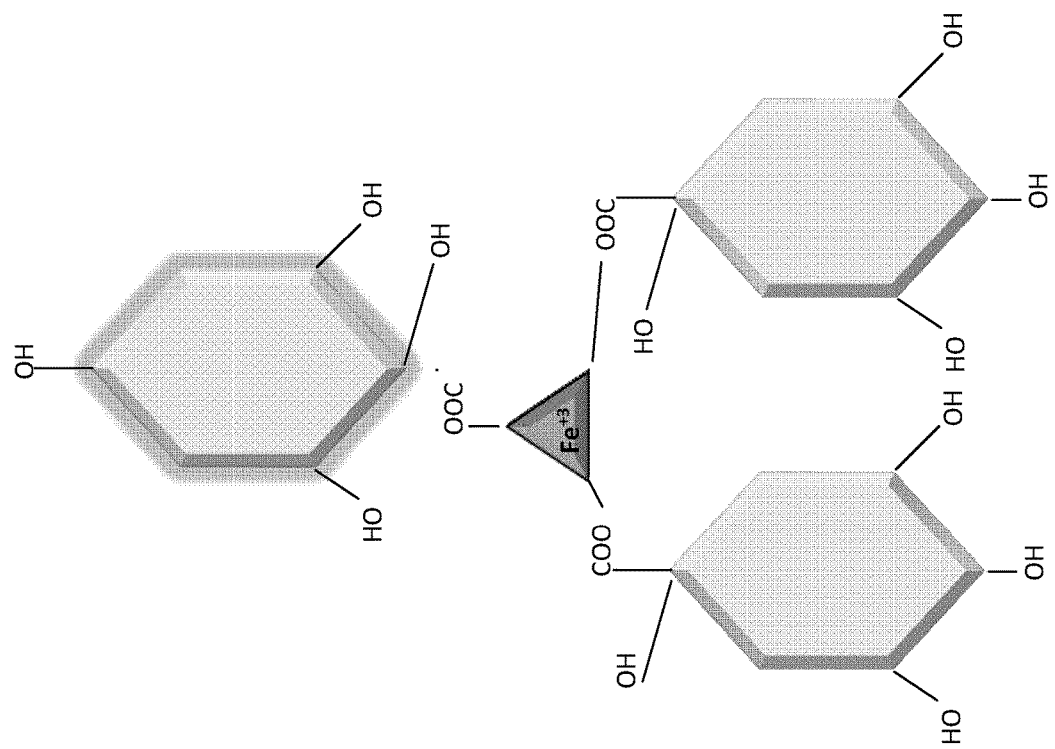
FIG. 11 shows Ferric-Quinate 1, 3, 4, 5-Tetrahydroxy Cyclohexan carboxylic acid

The ability of MOMP268T/G to colonise chicks was determined. 6-weeks old birds (n=10 per group) were challenged with 3×10³ cfu wild-type strain NCTC11168-O or its isogenic mutant MOMP268T/G by oral gavage. Caecal colonisation levels were determined in birds from each group at 7 days post-challenge. The results show a significant reduction in the geometric mean colonisation levels in the caeca in the MOMP$^{268T/G}$ group compared to the wild-type (See FIG. 10). In addition, the ability of the mutant strain to invade the chicken's liver was examined. The results showed that MOMP$^{268T/G}$ was completely unable to invade compared to the wild-type strain, These results confirm the importance and biological relevance of MOMP glycosylation in the establishment of colonisation in vivo. Values less than 100 in FIG. 10 are arbitrary figures, and no *campylobacter* was recovered.

Ferric Quinate; an Inhibitor for *C. jejuni* Adherence

A number of phenolic compounds, including caffeic and quinic acids (Baqar et al.), have been shown to have high levels of antioxidant activity and other potentially health-promoting effects in vitro. Also, quinic acid occurs in tea, coffee, fruits and vegetables. In particular, plants use the low molecular mass D-(-)-quinic acid (Baqar et al.) for mobilization of Iron and further use of this metal by cellular structures in metabolic pathways (Menelaou et al., 2009).

Ferric quinate Fe(QA)3 was identified as having promising inhibitory effects in vitro and in vivo on *C. jejuni* adhesion to BgAgs.

Figure 12:
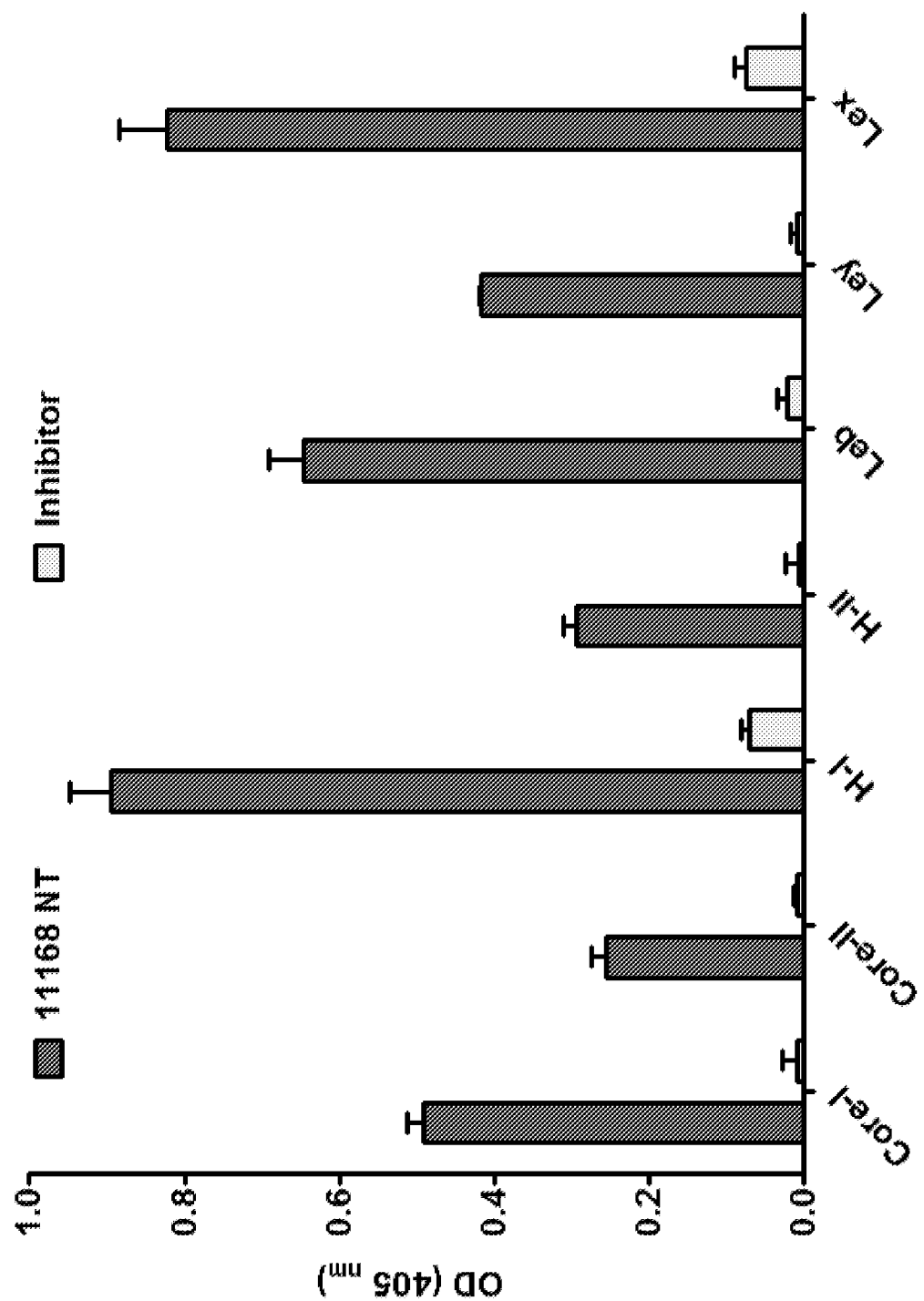
FIG. 12 shows the inhibitory potential of Ferric Quinate Fe(QA)3 on adherence of *C. jejuni* was analyzed by ELISA using BgAgs (Core-I, Core-II, H-I, H-II, Leb, Ley and Lex).
Figure 13:
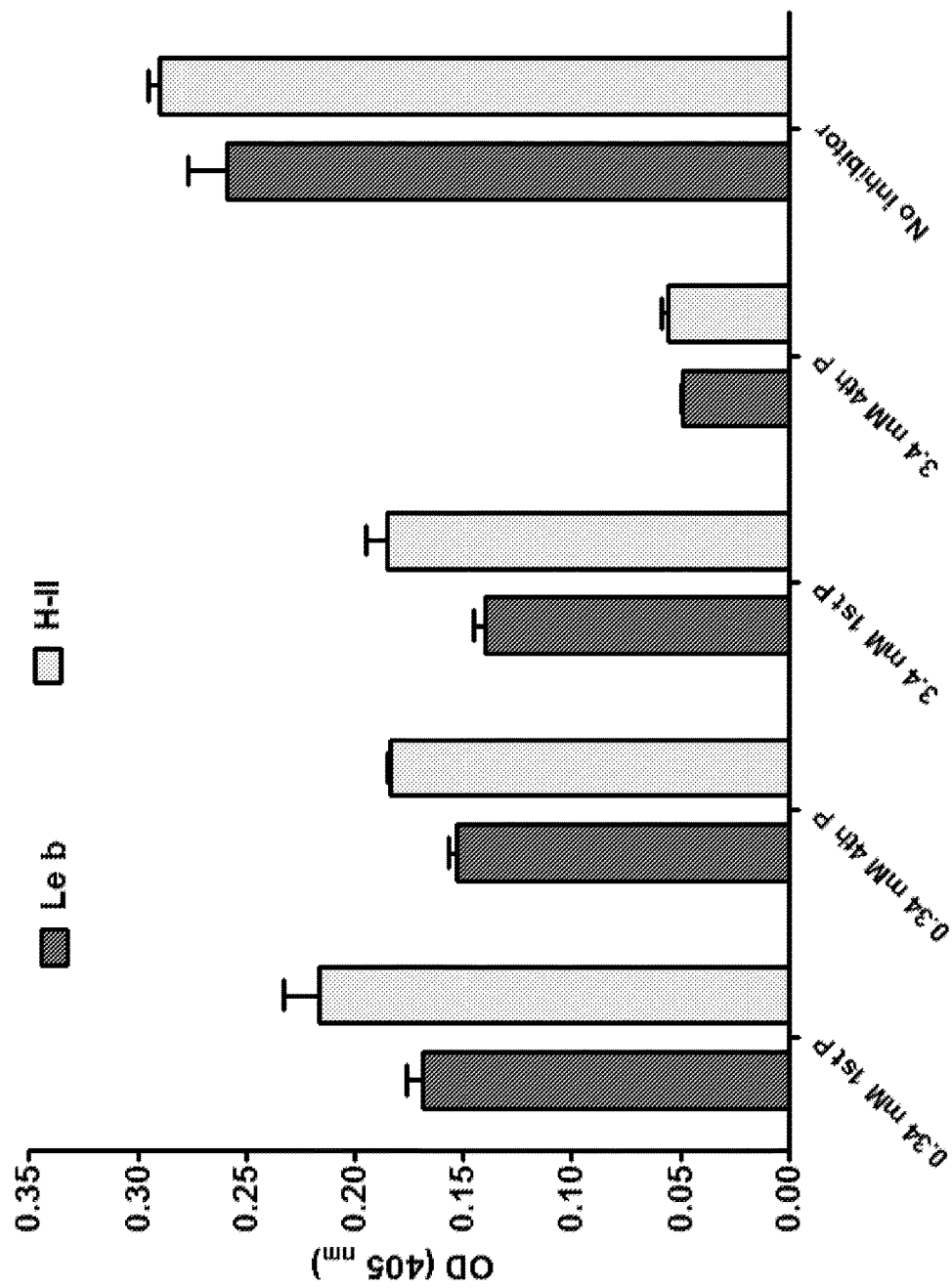
FIG. 13 shows the inhibitory potential of Ferric Quinate Fe(QA)3 on adherence of *C. jejuni* was analyzed by ELISA using BgAgs (Core-I, Core-II, H-I, H-II, Leb, Ley and Lex).

The inhibitory potential of Ferric Quinate Fe(QA)3 on adherence of *C. jejuni* was analyzed by ELISA using BgAgs (Core-I, Core-II, H-I, H-II, Leb, Ley and Lex). *C. jejuni* was pre-incubated with 34 μM Fe(QA)3 and specific inhibition was also analyzed by post-treatment of *C. jejuni* with Fe(QA)3 which bound to BgAgs at the time. The result showed that Fe(QA)3 conferred a 90% inhibition of binding, while Quinic Acid alone provided no inhibition of *C. jejuni* binding to all examined BgAgs. In addition the results from the bacterial culture (MH) containing Fe(QA)3 approach also demonstrated reproducible inhibition of microbial adherence. In addition, the sequential passages (P) of bacteria to the new plate containing Fe(QA)3 didn't cause any resistance concerning the binding abilities (see FIGS. 12 and 13).

To further clarify the growth-effect properties of Fe(QA)3, we investigated the effect of adding Fe(QA)3 to the culture medium. Supplementation with the different concentrations of Fe(QA)3, (34 and 340 μM) did not affect the growth of *C. jejuni* NCTC11168 strain.

These inhibitory properties against *C. jejuni* adherence to BgAgs were analyzed in vivo. Ferric Quinate was used as an additive to water (0.034-0.34 mM) and as an inhibitor of *C. jejuni* NCTC11168 strain adherence to, and thus colonization, in the chicken intestinal tract. 6-weeks old birds (n=10 per group) were challenged with 3×103-5 cfu wild-type strain NCTC11168-O by oral gavage. Caecal colonisation levels were determined in birds from each group at 3 and 7 days post-challenge.

Figure 14:
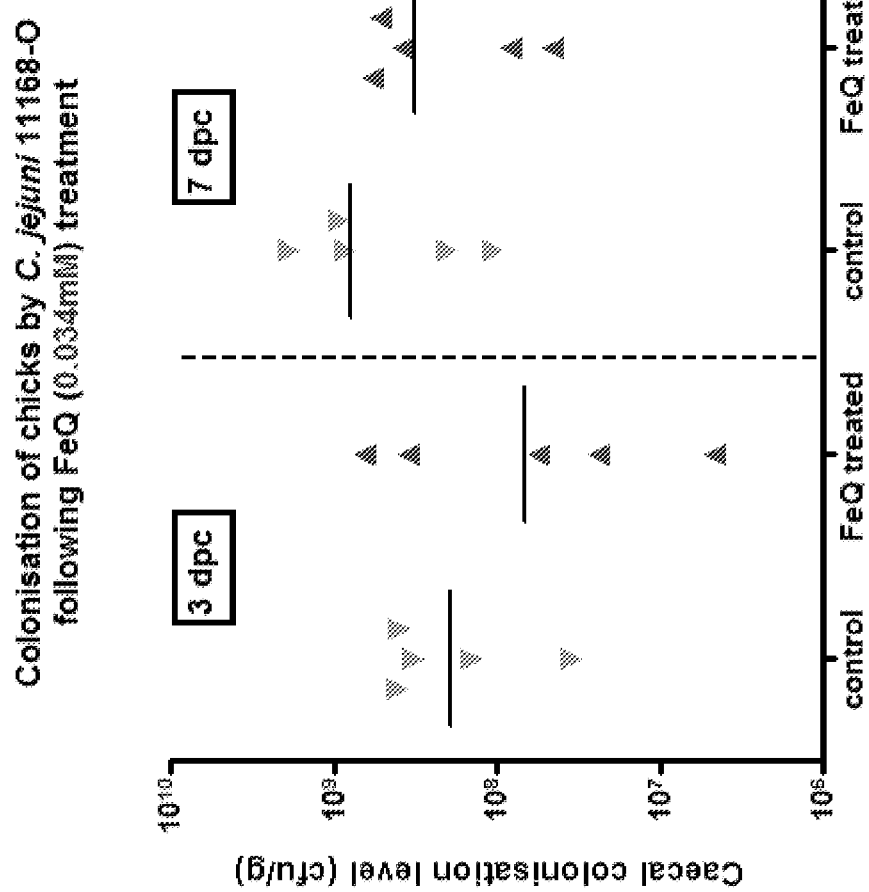
FIG. 14 shows colonisatin of chicks by *C. jejuni* 11168-O following FeQ (0.034 mM) treatment.
Figure 15:
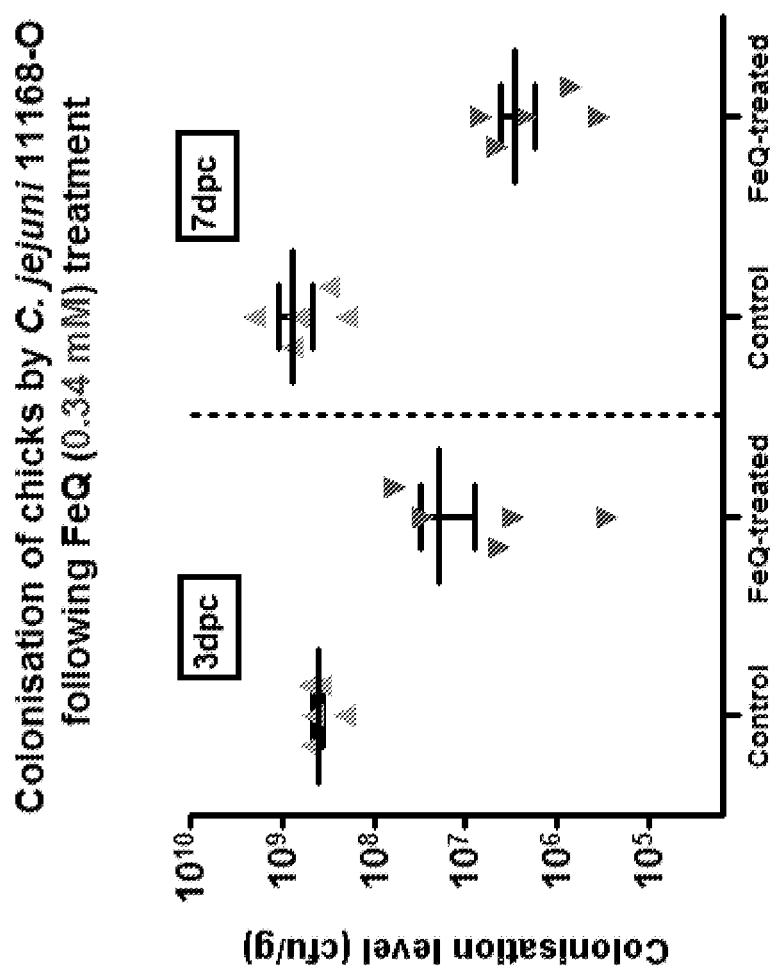
FIG. 15 shows colonisatin of chicks by *C. jejuni* 11168-O following FeQ (0.34 mM) treatment.
Figure 16:
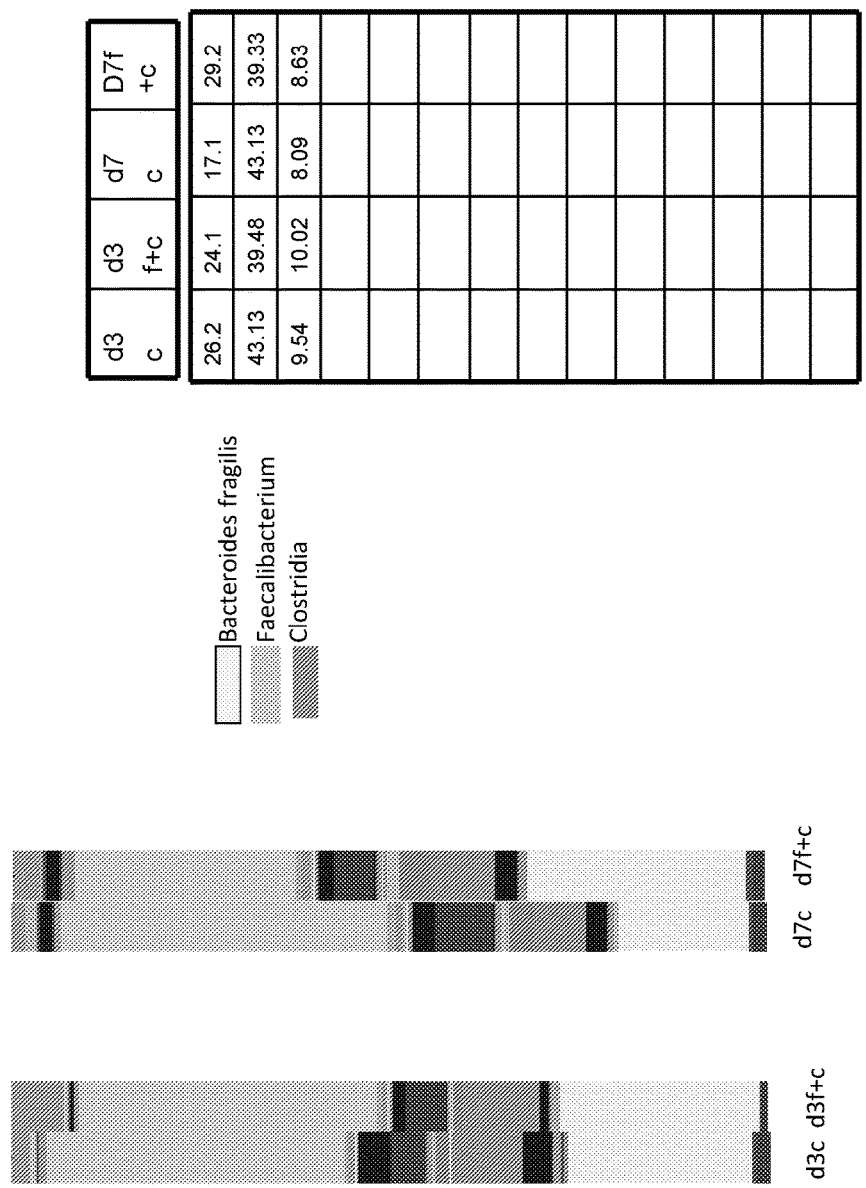
FIG. 16 shows metagenomic analysis of population treated with FeQ Genus/species level.

The complex reduced significantly the adhesion of *C. jejuni* (2-3 Log at 0.34 mM concentration) to the intestinal mucosa and epithelial lining by inhibiting the binding between bacterial adhesins, such as MOMP (confirmed by model), may FlaA, and the corresponding binding sites in the host intestinal epithelium see FIGS. 14 and 15.

In A Metagenomic analysis of population treated with FeQ at a Genus/species level a difference can be seen between FeQ treated and non-treated birds at day 7, there is a shift in the population with increase of Bacteriodetes phylum, especially *Bacteroides feacalis* (1, 2, 3).

MOMP is O-Glycosylated.

*Campylobacter* specifically modify their flagellar proteins with O-linked glycans that can constitute up to 10% of the protein mass. These modifications are necessary for flagellum assembly, and thus affect secretion of virulence-modulating proteins, bacterial colonization of the gastrointestinal tract, autoagglutination and biofilm formation.

Figure 3:
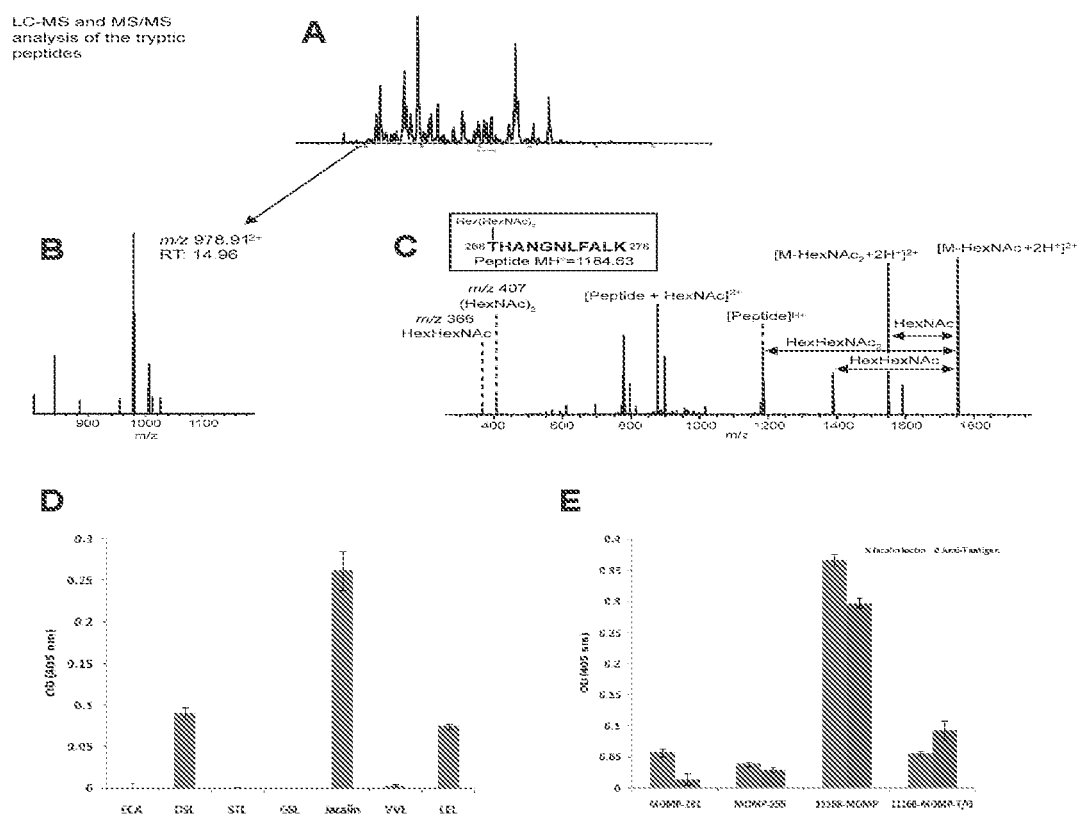

MOMP was purified from strains NCTC11168 and Cj-281 under native conditions and analysed by Nanoflow LC-MS/MS FT/ICR following in-gel protein digestion as described in A. Shevchenko, M. Wilm, O. Vorm, M. Mann, *Anal Chem* 68, 850 (Mar. 1, 1996). The migration of trypsin-digested MOMP peptides from both strains was essentially identical except for one peptide corresponding to amino acids 268-278, corresponding to the predicted loop 6: the strain NCTC11168 peptide showed a greater mass; MS/MS analysis confirmed that glycosylation of Thr-268 with a Hex-(HexN-acetylamine)$_3$ (where Hex can be Glucose or Galactose) was responsible for the observed shift (FIGS. 3A, B and C). FASTA sequence alignment of clinical isolates indicated that Thr-268 on loop 6 of strain NCTC11168 appears to be conserved in 52% of isolates.

Site-directed substitution of Thr$^{268}$ to Gly was carried out on MOMP of strain NCTC11168 and a clinical isolate Cj-266 (yielding MOMP$^{268T/G}$, S5—Table). This substitution caused a clear shift in the protein's migration, strongly suggesting the loss of its glycosylation (S5). The ability of this mutant to bind to a range of BgAgs in an ELISA assay was examined and it was shown to have a reduction in binding to each of examined BgAgs (FIG. 2A). Also, a reduced biofilm formation was observed, which indicates that O-glycosylation of MOMP plays an important role in this context (S8—Fig. A and B).

The Role of PglB and PseD Transferases on MOMP Glycosylation.

Flagellin is the only O-glycosylated *C. jejuni* protein to have been reported and glycans constitute ca. 10% to this protein's weight. The predominant O-glycans attached to the *Campylobacter* flagellum are derivatives of pseudaminic acid or legionaminic acid, which are C9 sugars that are related to sialic acids. In addition, the related human gastric pathogen *H. pylori* also O-glycosylates its flagella with Pse, similarly to *C. jejuni*, and modification is required for bacterial motility and flagellar assembly.

Interestingly, specific loss of Pse5Am due to mutation of the Pse biosynthesis A gene (pseA) in *C. jejuni* subsp. *jejuni* 81-176 resulted in loss of auto-agglutination and reduced adherence to and invasion of intestinal epithelial cells in vitro, and reduced virulence in the ferret model.

Also, PseD as a putative PseAm transferase showed that mutation in pseD lacked PseAm on flagellin and failed to auto-agglutinate.

The general protein glycosylation (Pgl) pathway involves several key "Pgl" enzymes, of which PglB is critical for protein N-glycosylation i.e. transfer of the first glycan molecules to the target proteins at specific Asn residues.

In order to evaluate the contribution of PseD and PglB transferases on *C. jejuni* MOMP glycosylation and its role on bacterial binding activity, a pglB deletion mutant was created in strain Cj81-176 and pseD deletion in strain NCTC11168; pglB deletion had no detectable impact on MOMP gel migration, glycan staining (data not shown), or bacterial binding to any of the examined BgAgs (S7—Fig. A). However, strain NCTC11168 pseD deletion resulted a significant reduction in binding to all examined BgAs and biofilm formation (data not shown).

These findings indicate that *C. jejuni* strain NCTC11168 encodes a transferase that is involved in post-translational modification of protein, which plays an important role in bacterial adhesion and reveals unusual post-translational modifications; an O-linked Hex-(HexNAc)$_3$ at Thr$^{268}$. These post-translational modifications might undergo phase variation and may also vary in structure from one generation of *C. jejuni* to the next, and have a function in immune escape.

Moreover, these findings provide new insights into MOMP structure and resolve long-standing issues regarding the adhesion molecules which mediate the bacterial binding to the BgAgs. The pathogenesis and study the effects on processes such as colonization, invasion, and the ability to stimulate the host inflammatory response remain to be elucidated.

Determination of MOMP Glycan Composition.

Lectin kit was used for determination of the MOMP glycosylation constituent. The kit consists of 7 different lectins with overlapping specificity. The purified NCTC11168-MOMP in lectin array revealed significant binding to Jacalin lectin and in a lesser extent to GSL and LEL (FIG. 3D). Among the galactose-specific lectins, the lectin from *Artocarpus integrifolia*, known in the literature as Jacalin, exhibits specificity toward human tumour specific Thomsen-Friedenreich disaccharide (T-antigen, Gal$\beta_{1-3}$GalNAc$\alpha_1$-Ser/Thr).

Moreover, to confirm the Jacalin binding specificity, monoclonal anti-T-antigen was used against purified MOMP isolated from different strains (NCTC11168-MOMP, NCTC11168 MOMP$^{268T/G}$ and two clinical isolates with low binding activity; Cj281 and Cj-255). FIG. 3E shows that anti-T antigen antibody and Jacalin lectin reacted specifically with purified NCTC11168-MOMP. The observation that NCTC11168-MOMP interacts with Jacalin and anti-T antigen but not MOMP isolated from low binder strains and NCTC11168 MOMP$^{268T/G}$ (FIG. 3E) indicates that strain NCTC11168-MOMP is likely to be the O-linked trimeric form of T-antigen (Gal$\beta_{1-3}$GalNAc$\beta_{1-4}$GalNAc$\beta_{1-4}$GalNAc$\alpha_1$-Thr$^{268}$).

Glycosylation of MOMP with T-antigen presented herein provides an important insight on the role of glycosylation for *C. jejuni* binding activity to Lewis antigens and in MOMP immunogenicity. Further determination of the other N- and O-glycosylated outer membrane proteins may shed light into the development of a glycoconjugate based vaccine in the future.

The Role of Glycan in MOMP Binding to BgAgs

The advances in computer technology and new modelling techniques have facilitated simulations of peptide folding at the atomic level. Although gram-negative bacteria possess quite different homology in primary sequences of their porins, they are remarkably similar in their beta-barrel structure. Hence, we employed the beta-barrel structure from *Comamonas acidovorans* (1E54.pdb) as a template and constructed our model based on this assumption. In order to understand better the role of MOMP glycosylation in *C. jejuni* binding to the BgAgs, here we present the construction and molecular dynamic properties of MOMP and its glycosylated form.

The initial structure was constructed and showed to have 9 loops and 18 beta-strands. The lowest energy structure obtained from molecular dynamics (MD) simulations at 300 Kelvin (K) is represented in S9—Fig. A and B. This structure was glycosylated at residue 268 with a glycosyl group. The lowest energy structure of glycosylated MOMP (gly-MOMP) obtained from MD simulations was superimposed on the lowest energy structure of MOMP to see the conformational changes induced by the introduction of glycosylation as presented in FIG. 4B. It shows that the major changes occur in loops 4, 6 and 7 constructed roughly of 169-200, 256-274 and 296-333 residues where loop 6 bears the glycosyl group. However, it shows that a small change appears in the barrels. The approximate boundaries of two proteins in the hydrophobic part of the outer membrane are indicated by horizontal lines as represented in FIG. 4A.

Interestingly, the galactosyl residue has a favourable interaction with Arg$^{328}$ residue as indicated in FIG. 4 but upon complex with H-II the glycosylated residue undergoes considerable conformational changes where this interaction vanishes and the group tends to move towards loop 4 to interact with Thr$^{186\ and\ 187}$ (FIG. 4A). In contrast, this conformational change did not occur in the case of gly-MOMP with $L_e$b.

The MOMP protein has a canal-like cavity as seen in S9—Fig. A and B, which is expected to be capable of accommodating very large molecules. A mimic of Lewis antigen, type-1 Lewis carbohydrate determinant (Le$^b$) and type-2 H-II antigen (S9—Scheme 2) were docked into the cavity of MOMP and gly-MOMP. These complexes were computed for MD simulations. The average energies derived from MD simulations of complexes are listed in S9—Table. The introduction of the ligands within the cavity of MOMP leads to a remarkable effect on conformational changes in the loops, especially in loops 4 and 7. These two loops are the longest among the rest and obviously undergo significant conformational changes compared with others. Interestingly, it was found that gly-MOMP has a relatively stable structure since it shows that only loop 7 slightly undergoes conformational changes upon this complex. This may mean that glycosylation enhances the stability of the protein and allow it to be immunologically inert through molecular mimicry of its host.

Corresponding MOMP amino acids, which mediate binding to Le$^b$ and H-II antigens. The interactions involved in the complexes of both proteins with Le$^b$ and H-II are represented in FIG. 5A-F. The channel of these barrel proteins largely contains arginine and lysine residues, which are likely responsible for the recognition of these sugars. It is apparent that gly-MOMP has favourable interactions with Le$^b$ compared to MOMP. The residues Arg$^{352}$, Lys$^{278\ and\ 385}$ seems to be the major contributor in the interaction of the glycosylated protein with Le$^b$ via hydrogen bonds whereas only the residues Asn$^{258}$ and Lys$^{278}$ are involved in the interaction of MOMP with Le$^b$. The residues 352 and 385 are the members of the beta-barrel 7, which are the part of loop 7. This loop, as mentioned earlier, mostly undergoes conformation changes during the molecular dynamic simulation (FIG. 4B). The glycosyl group interacts with this loop, thus leading to favourable conformational change for the interaction, and consequently resulting in a well-orientation of these residues to interact with Le$^b$. The glycosyl group is sandwiched between loops 4 and 7, probably influencing the dynamics of these loops, thus contributing to the binding ability of the protein. Calculations also show that the glycosylated protein has more favourable van der Waals (vdw) interactions compared with MOMP. It appears that the residues Leu$^{290}$, Tyr$^{294}$, Phe$^{395}$ and Ile$^{337}$ are well-located over the hydrophobic surface of Le$^b$ in the complex of gly-MOMP compared with MOMP (FIGS. 5B and C). This is reflected in 67 kcal/mol vdw energy difference between two complexes. It seems that H-II is bound to proteins with a similar mode to Le$^b$. The residues Lys$^{278}$ Arg$^{352\ and\ 381}$, are involved in the complex of both proteins with H-II (FIGS. 5E and F). The only difference is in the residues Asp$^{261}$ and Ser$^{397}$, the first is involved in the complex of MOMP and the second in gly-MOMP. The very large binding energy obtained for the complex of H-II by MMPBSA could not be explained but it still shows that gly-MOMP binds to H-II better than MOMP itself.

The other outcome gathered from MD calculations is the conformation and alignment of the ligands within the cavities of two proteins. They show that both ligands have different conformational orientations in the active sites of the proteins as indicated in S9—FIG. 2A,B.

In conclusion, although MD simulations were carried out in short MD simulation time and in implicit salvation medium, it still shows that glycosylation of major outer membrane proteins provides better conformational changes and consequently affinity for binding and hence recognition of Lewis antigens compared with its parent protein. Conformational MOMP epitopes are important in host immunity, and variation in surface-exposed regions probably occurs as a result of positive immune selection during infection. porA diversity has been exploited in genotyping studies using highly discriminatory nucleotide sequences to identify potentially epidemiologically linked cases of clinical manifestations of *C. jejuni* infection. Interestingly, the host immune response has been suggested to play a role in defining the more antigenically homogeneous clonal complexes, and this could also reflect niche adaptation. For example, alignment of MOMP sequences isolated from human and chicken associated strains demonstrates that they differ predominantly at loop 4, therefore variation of loop 4 could influence the bacterial binding ability and consequently niche adaptation.

Moreover, identification of protein glycosylation profile of *C. jejuni*, mainly those related to outer membrane, are fundamental to understanding the diverse pathogenicity of *C. jejuni* strains among different hosts. The model can be mined for sub-networks of biological interest, such as essential amino acid that suggest candidate drug targets. Importantly, some low confidence interactions may be found to be biologically significant by experimental validation.

The model for *C. jejuni* interaction to Le$^b$ and H-II antigens mediated by MOMP generated here substantially increases our knowledge about the protein and its glycosylation and the role in interactions detected thus far for the *C. jejuni* outer membrane.

Thus, the structural glycobiology will play a key role in unraveling other glycan structures that mediate the host-bacteria interaction through MOMP/FlaA proteins, contributing decisively for identification and validation of new glycan receptors for these bacterial lectins. This information will be of major importance for the improvement and design of new therapies to overcome the *C. jejuni* infection.

Biofilm Formation

Auto-agglutination (AAG) has been demonstrated to be critical for virulence for a variety of pathogens, and can play a role in adherence, microcolony formation, biofilm formation, and resistance to acid and phagocytosis. In two previous studies on AAG of *C. jejuni* (N. Misawa, M. J. Blaser, *Infect Immun* 68, 6168 (November, 2000) and N. J. Golden, D. W. Acheson, *Infect Immun* 70, 1761 (April, 2002)), there appeared to be an association with adherence or invasion of intestinal epithelial cells.

The impact of flaA mutation and/or MOMP-T/G substitution on biofilm was examined. Biofilms were generated over 48 h on polystyrene plates at 42° C. under microaerophilic conditions, and stained with crystal violet before they were assessed by opacity measurement, using an ELISA reader at $A_{595}$. In control samples without sugar added, biofilm formation of strain NCTC11168-ΔflaA deletion and MOMP$^{T/G}$ were significantly lower than wild type strain (WT). Already known from previous studies, O-linked glycosylation of flagellin is necessary for proper assembly of flagella filaments, also flaA mutation leads to reduction in biofilm formation due to reduced motility. To determine the role of host BgAgs in inhibiting biofilm formation, various antigens were added into the media inoculated with different strains. A reduced biofilm formation was observed in presence of free sugar structures in media; most dramatic drop is seen in WT. For wild type strain, the H-II produced the highest reduction by 90% and followed by Le$^b$ structure with 80% compared with other examined BgAgs. Probably, the greater reduction is due to the higher affinity, which effects the equilibrium equation, and requires longer time for detachment of free sugar from surface molecules and prevents the biofilm formation.

Figure 7:
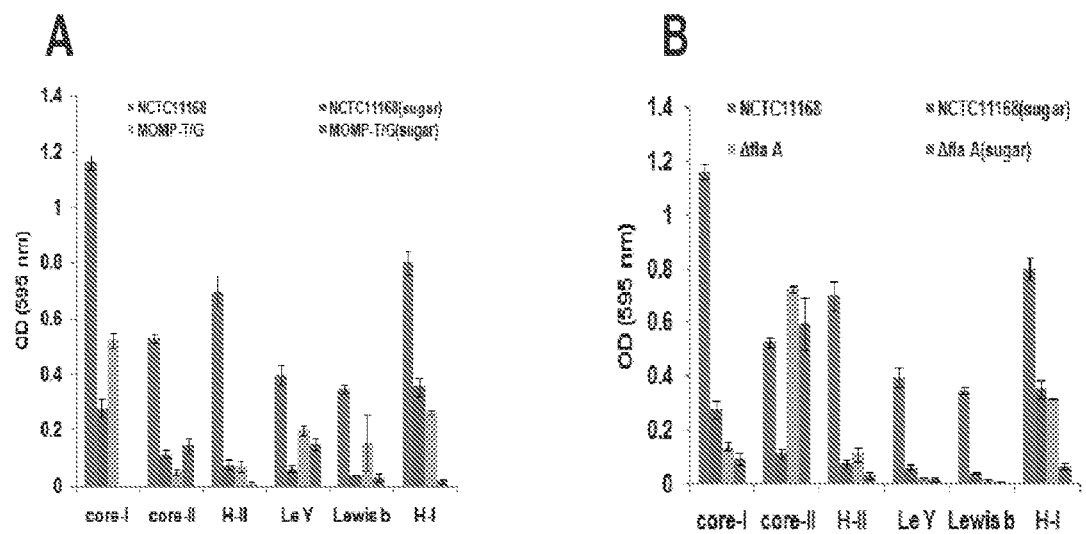
Figure 8:
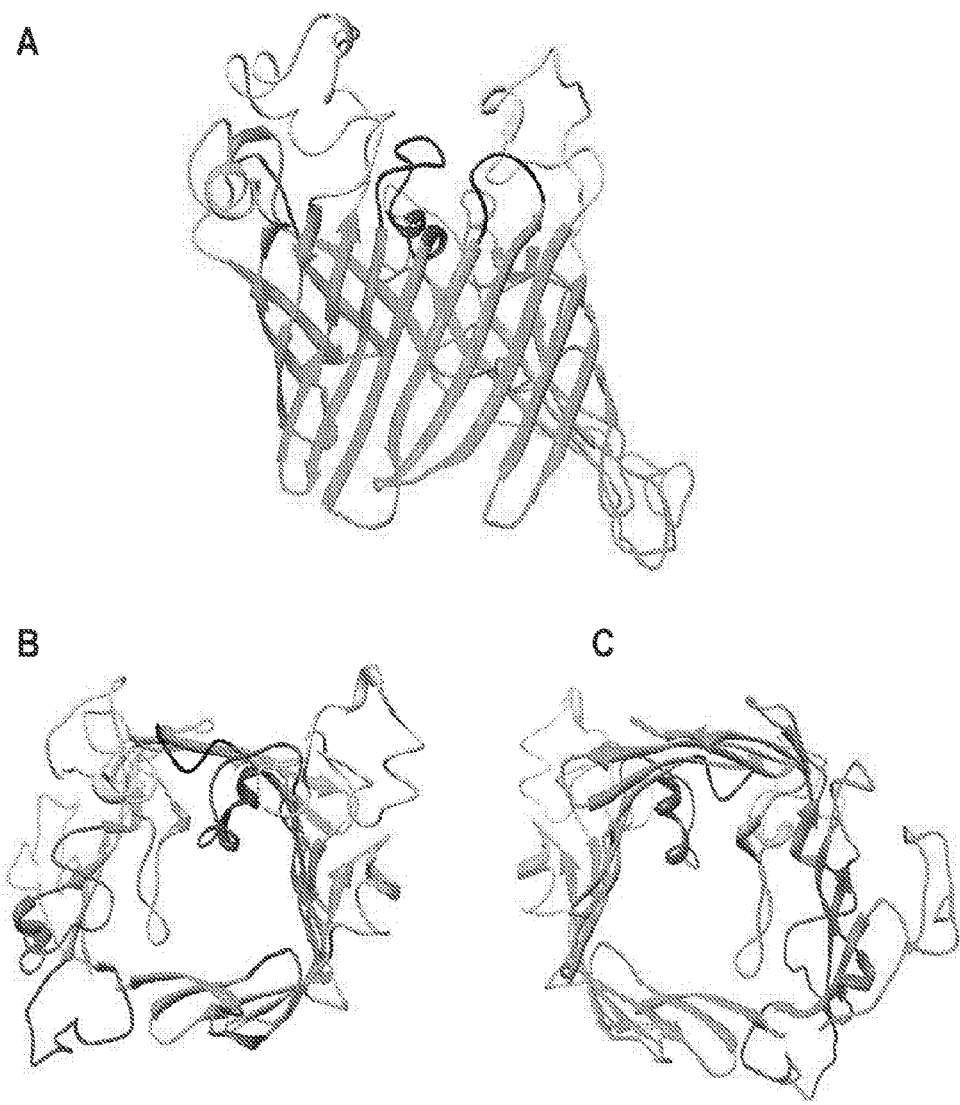

Although, the stronger binding affinity more interruption in biofilm formation. These data suggest that BgAgs compete with AAG and biofilm determinants on flagellin and MOMP, also confirmed the validity of the model and underlined the critical role of O-glycosylation in biofilm formation (FIG. 7—Figure A and B).

This experiment was repeated and same pattern was achieved. Taking in account that position of plate might affect growth; we added the samples and its control in identical position on different plates. In addition, we took an aliquot from each sample and grow on CCDA, it showed that growth were equal in all.

The Lowest Energy Structure of MOMP Protein.

Functional and structural studies of outer membrane proteins from Gram-negative bacteria are frequently carried out using refolded proteins. Although several structures of bacterial OMPs (outer membrane proteins) are now available, a large number of these proteins are still structurally and functionally poorly characterized. A model was generated for *C. jejuni* MOMP to study the effect of glycosylation on MOMP conformation and also the role of it in bacterial binding activity. The model may be used for predicting the functions of uncharacterized proteins and for mapping functional pathways in *C. jejuni* and other prokaryotes. The data can provide a framework for understanding dynamic biological processes, such as the *C. jejuni* primary attachment to histo-blood group antigens.

Alignment of porA from Different Bacterial Isolates

CLUSTAL W (1.81) multiple sequence alignment using BLOSUM weight matrix, of *Campylobacter jejuni* major outer membrane sequences downloaded from the Uniprot Database (http://www.uniprot.org/). Also, three non-binder (NB) and three high binder (HB) clinical isolates were added into this series (in house sequencing). Amino acid positions refer to positions in strain NCTC11168 (P80672).

The alignment showed the major contributors of the interaction of the glycosylated MOMP with Le$^b$ via hydrogen bonds are residues 352 (Arg), 381 (Arg), and 278 (Lys), whereas only the residues 352 and 278 are involved in the interaction of non-glycosylated MOMP with Le$^b$. Amino acid sequence alignments indicating MOMP active sites of *C. jejuni* isolates from different patients has been sufficiently stable for this purpose. Interestingly, residue 278 (Lys) is semi-conserved in 16 isolates and was substituted by Arg which is able to mediate the binging through hydrogen bond in similar fashion as residues 381(Arg) and 352(Arg).

In addition, alignment of these sequences also demonstrates that they differ predominantly at loop 4 but the binding pocket between loop 4 and 7 is relatively conserved. A definitive study on MOMP host association would require glycosylation analysis data for isolates from a wide variety of hosts. A complicating factor in exploring these relationships for all *C. jejuni* may be their ability to colonize multiple hosts and thereby undergo exposure to many different immune responses.

Moreover, the glycosylation site $Thr^{268}$ in the MOMP proteins was conserved in 52% of bacterial isolates aligned in this study, which indicate the importance role of Thr in 268 position.

Computational Modelling

All molecular dynamic simulations were conducted by using AMBER (version 10.0) (40) suite of programmes on the Linux/Intel PC cluster of TR-GRID maintained by TUBITAK (Scientific and Technologic Research Council of Turkey). Simulations were initiated using the following amino acid sequence SEQ ID No. 1(MKLVKLSLVAALAAGAFSAANATPLEEAIKDVD-VSG VLRYRYDTGNFDKNFVNNSNLNNSKQDH-KYRAQVNFSAAIADNFKAFVQ FDYNAADGGYGAN-GIKNDQKGLFVRQLYLTYTNEDVATSVIAGKQQLNLI WTDNAIDGLVGTGVKVVNNSIDGLTLAAFAVDSF-MAAEQGADLLEHSNIS TTSNQAPFKVDSVGNLY-GAAAVGSYDLAGGQFNPQLWLAYWDQVAFFY AVDAAYSTTIFDGINWTLEGAYLGNSLDSELDDK-THANGNLFALKGSIEVN GWDASLGGLYYGDKEKA-STVVIEDQGNLGSLLAGEEIFYTTGSRLNGDTG RNIF-GYVTGGYTFNETVRVGADFVYGGTKTEAANHLG-GGKKLEAVARVD YKYSPKLNFSAFYSYVN-LDQGVNTNES ADHSTVRLQALYKF). The model was constructed using the idea of the similarity of secondary structure of these class of proteins. The core structure of MOMP was initiated by using the skeleton of outer membrane protein of anion-selective porin from *Comamonas acidovorans* (1E54.pdb) and *Pseudomonas aeruginosa* (2QTK.pdb) as described in S. Biswas, M. M. Mohammad, L. Movileanu, B. van den Berg, *Structure* 16, 1027 (July, 2008), as a template to build the beta-barrels. A combination of HyperChem (HyperChem™ Professional 7.51), chimera (UCSF), and the LEaP module as implemented in AMBER was used to build the core and add the loops and turns. The initial structure was heated from 0 Kelvin (K) to 325 K with a restrain of 10 kcal $mol^{-1}$ $Å^{-2}$ on residues of beta-barrels to avoid the effect of conformational changes in loops on beta-barrels for a period of 200 ps in four steps, followed by simulations from 0 K to 325 K for another period of 200 ps without any restrains in four steps. The system was further simulated at 300 K for a period of 8 ns. All molecular dynamics (MD) simulations were carried out using pmemd (Particle Mesh Ewald Molecular Dynamics) model of programme as implemented in AMBER. The ff99SB force field was employed and solvation effects were incorporated using the Generalized Born model, as implemented in AMBER. A lower energy structure was chosen and this was glycosylated at the residue 268 (Thr) with Gal(β 1-3)-GalNAc(β 1-4)-GalNAc(β 1-4)-GalNAc-α-linked to the protein as illustrated in Scheme 1 using xleap as implemented in AMBER. Glycam04 force field was used for carbohydrate unit. The charge on the oxygen of the site chain of Thr was changed from −0.6761 to −0.4599 and the atom type of OS was assigned. The angle and dihedral parameters for dimethylether (CT-OS-CG) and dimethoxymethane (H2-CG-OS-CT) were used for the glycosylated angle and dihedral for the carbohydrate linkage.

The system was minimized with 500 steps of steepest descent minimization followed by 500 steps of conjugate gradient minimization and heated at 400 K for a period of 10 ps to avoid bad contacts with a restrain of 10 kcal $mol^{-1}$ $Å^{-2}$ on the protein backbone and to have the carbohydrate groups in a good shape. The system was heated from 0 K to 325 K for a period of 200 ps without any restrains, followed by simulation at 300 K for a period of 3.5 ns.

Root-mean-square deviation (RMSD) analysis for the complex system was carried out on the trajectories by the ptraj module of AMBER (v10). 3D structures were displayed using by Chimera (UCSF), and RMSD graphics are shown by XMGRACE package programme.

Docking calculations were performed to accommodate the Lewis antigen ($Le^b$) and H-II antigen as seen Scheme 2 within the cavity of the protein. Docking of the $Le^b$ was carried out using DOCK 6.0. Docking was performed with default settings to obtain a population of possible conformations and orientations for $Le^b$ at the binding site. Spheres around the centre of the binding pocket were defined as binding pocket for the docking runs. Since Dock 6.0 program employs sphgen to produce spheres and hence for technical reasons, sphgen cannot handle more than 99999 spheres, the residues forming loops were stripped off and thus the calculations of spheres and grids were only performed with the beta-barrels forming the cavity. Then the coordinates of the $Le^b$ obtained was recorded and AN/II-Bee (Austian model with Bond and charge correction), atomic partial charges and atom types of general amber force field (GAFF) were assigned for it using antechamber as implemented in AMBER. Xleap was used to accommodate the $Le^b$ within the cavity of MOMP with combine command as well as to produce topology/parameter and coordinate files. The atom type of $Le^b$ was changed to those described in Glycam04 force field. The system was minimized, followed by MD simulation at 300 K for about 6.0 ns. The same procedure was applied to the glycosylated protein.

MM/PBSA Calculations:

This study applies a second-generation form of the Mining Minima algorithm, termed M2, to analyze the binding reactions of host-guest complexes in water. The MM-PB/SA module of AMBER (v9) was applied to compute the binding free energy ($\Delta G_{bind}$) of each complex using the MM/PBSA method. For each complex, a total number of 200 snapshots were extracted from the last 1 ns of the complex trajectories.

During conformational searching and the evaluation of configuration integrals, Welec is computed with a simplified but fast generalized Born model. The electrostatic solvation energy of each energy-well is then corrected toward a more accurate but time-consuming finite-difference solution of the Poisson equation. The dielectric cavity radius of each atom is set to the mean of the solvent probe radius 1.4 Å for water and the atom's van der Waals radius, and the dielectric boundary between the molecule and the solvent is the solvent-accessible molecular surface. The solvation calculations use a water dielectric constant of 80. The MM/PB SA method can be conceptually summarized as:

$$\Delta G_{bind}=G_{complex}-[G_{host}+G_{ligand}] \quad (1)$$

$$G=E_{gas}+G_{sol}-TS \quad (2)$$

$$E_{gas}=E_{bond}+E_{angle}+E_{torsion}+E_{vdw}+E_{ele} \quad (3)$$

$$G_{sol}=G_{PB}+G_{SA} \quad (4)$$

$$H=E_{gas}+G_{sol} \quad (5)$$

$$G_{sol}=G_{PB}+G_{SA} \quad (6)$$

$$H=E_{gas}+G_{sol} \quad (7)$$

$$S_{tot}=S_{vib}+S_{trans}+S^{rot} \quad (8)$$

$$\Delta G=\Delta H-T\Delta S \quad (9)$$

where $G_{complex}$, $G_{host}$, and $G_{ligand}$ are the absolute free energies of the complex, host and the ligand species respectively as shown equation (1). Each of them is calculated by summing an internal energy in gas phase ($E_{gas}$), a solvation free energy ($G_{sol}$), and a vibrational entropy term equation (eq 2). $E_{gas}$ is Standard force field energy, including strain energies from covalent bonds and torsion angles as well as noncovalent van der Waals and electrostatic energies (eq 3). The solvation free energy, $G_{sol}$, is calculated with a PB/SA model, which dissects solvation free energy as the sum of an electrostatic component (GPB) and a nonpolar component (GSA) as shown in eq. 8, $S_{tot}$ is the total entropy comprising of translational ($S_{trans}$), vibrational ($S_{vib}$) and rotational ($S_{rot}$) entropies as gas phase for each species as shown in eq. 6. In present study the entropy term was not included in calculations.

programme implemented in amber was used to derive the charges for each fragment. The capes, acetyl and NHMe were removed from each fragment and the model was built using xleap. ff99SB library was used to build library file for the model, which includes parameters such as atom type, bond, angles and dihedral. The topology and coordinate files were recorded for the model.

2) Conformational Search Using Molecular Dynamic Simulation

The structure was minimized at a total of 1000 steps; 500 of steepest descent (ncyc=500) followed by 500 of conjugate gradient (maxcyc-ncyc) in vacuum, followed by heating from 0 K to 700 K at seven steps each with 100 ps. The

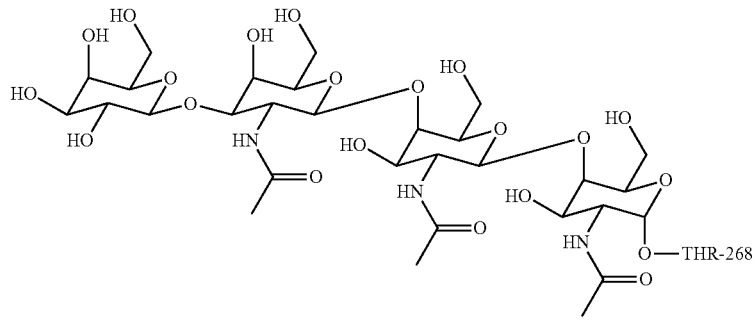

Scheme 1.
The structure of glycosylate group, Gal(β1-3)-GalNAc(β1-4)-GalNAc(β1-4)-GalNAcα1-Thr.

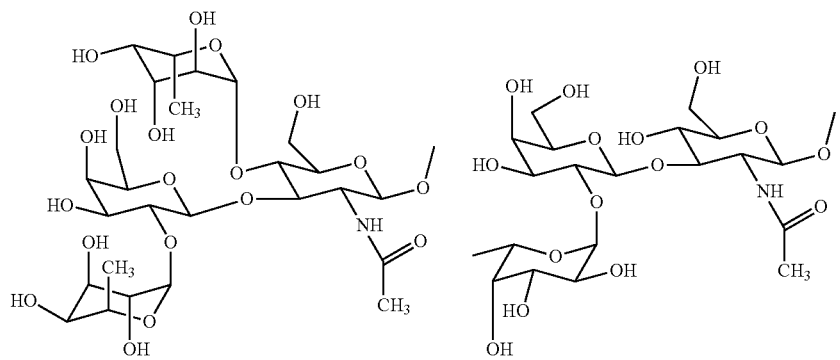

Scheme 2.
The structure of the lagands used are type I and II Lewis antigens. Lewis b (left) H-II antigen (right).

Building and Developing Amber Parameters for the Inhibitors

1) Charge Derivation for the Inhibitor

Figure 9:
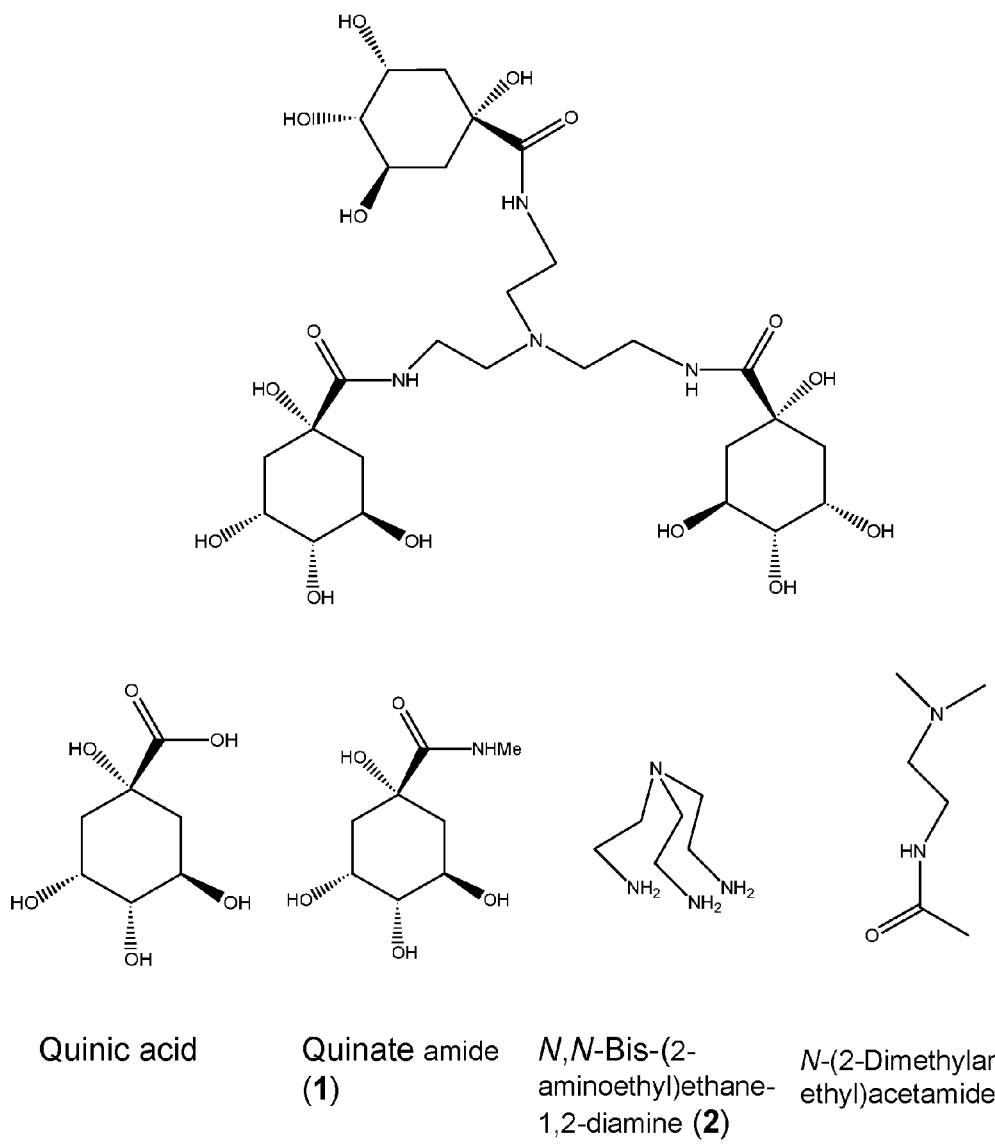
FIG. 9 shows molecules used in the modelling of molecules that bind to MOMP.

The model was divided into two fragments, one included quinate caped with NHMe ((1) in FIG. 9) and another included N,N-bis-(2-aminoethyl)ethane-1,2-diamine core ((2) in FIG. 9), which was further simplified into N,N-dimethylethane-1,2-diamine caped with acetyl ((3) in FIG. 9). The first stage was to optimize quinate amide and acate amide residues. This was done with a QM method at a reasonably high level of theory, which was done with MP2/6-31G* employing Gaussian 03 package programme. The original x-ray structure of quinic acid was used for quinate amide. The next stage was to calculate an ESP for each of the two optimized geometries that can ultimately be read by the RESP programme. HF/6-31G* as the level of theory was used to derive ESP for two structures. The RESP system was further run at 700 K for 1 ns. Few conformational minima were chosen and they were and they were cooled down to 300 K, each of which was further run at 300 K for 5 ns. From these runs a few conformations with minimum energy were chosen and they were minimized amber then with quantum mechanical calculation at B3LYP/6-31G* level of theory to locate the structure with the lowest energy.

Alignment of porA from Different C. jejuni Isolates.

CLUSTAL W (1.81) multiple sequence alignment using BLOSUM weight matrix, of Campylobacter jejuni major outer membrane sequences downloaded from the Uniprot Database (http://www.uniprot.org/). Also, three non-bind (NB) and three high binder (HB) j, clinical isolates were added into this series from in house sequencing. Amino acid positions referred to in this application relate to the amino acid positions in strain NCTC11168 (P80672) SEQ ID No 1

```
          10         20         30         40
MKLVKLSLVA ALAAGAFSAA NATPLEEAIK DVDVSGVLRY 50         60         70         80
RYDTGNFDKN FVNNSNLNNS KQDHKYRAQV NFSAAIADNF 90        100        110        120
KAFVQFDYNA ADGGYGANGI KNDQKGLFVR QLYLTYTNED 130        140        150        160
VATSVIAGKQ QLNLIWTDNA IDGLVGTGVK VVNNSIDGLT 170        180        190        200
LAAFAVDSFM AAEQGADLLE HSNISTTSNQ APFKVDSVGN 210        220        230        240
LYGAAAVGSY DLAGGQFNPQ LWLAYWDQVA FFYAVDAAYS 250        260        270        280
TTIFDGINWT LEGAYLGNSL DSELDDKTHA NGNLFALKGS 290        300        310        320
IEVNGWDASL GGLYYGDKEK ASTVVIEDQG NLGSLLAGEE 330        340        350        360
IFYTTGSRLN GDTGRNIFGY VTGGYTFNET VRVGADFVYG 370        380        390        400
GTKTEAANHL GGGKKLEAVA RVDYKYSPKL NFSAFYSYVN 410        420
LDQGVNTNES ADHSTVRLQA

LYKF
```

Annotation with "*", ":", "." refers to identical, conserved, semi-conserved amino acid substitutions respectively.

```
Hb1
                                                                (SEQ ID NO: 2)
MKLVKLSLVAALAAGAFSAANATPLEEAIKDVDVSGVLRYRYDTGNFDKNFVN-NSNLNN   59

Q2LAB2
                                                                (SEQ ID NO: 3)
MKLVKLSLVAALAAGAFSAANATPLEEAIKDVDVSGVLRYRYDTGNFDKNFVN-NSNLNN   59

Q2LAB0
                                                                (SEQ ID NO: 4)
MKLVKLSLVAALAAGAFSAANATPLEEAIKDVDVSGVLRYRYDTGNFDKNFVN-NSNLNN   59

Hb2
                                                                (SEQ ID NO: 5)
MKLVKLSLVAALAASAFSAANATPLEEAIKDVDVSGVLRYRYDTGNFDKNFVN-NSNLNN   59

NB1
                                                                (SEQ ID NO: 6)
MKLVKLSLVAALAASAFSAANATPLEEAIKDVDVSGVLRYRYDTGNFDKNFVN-NSNLNN   59

Q9F791
                                                                (SEQ ID NO: 7)
MKLVKLSLVAALAASAFSAANATPLEEAIKDVDVSGVLRYRYDTGNFDKNFVN-NSNLNN   59

Hb3
                                                                (SEQ ID NO: 8)
MKLVKLSLVAALAASAFSAANATPLEEAIKDVDVSGVLRYRYDTGNFDKNFVN-NSNLNN   59

D3FNB0
                                                                (SEQ ID NO: 9)
MKLVKLSLVAALAAGAFSAANATPLEEAIKDVDVSGVLRYRYDTGNFDKNFVN-NSNLNN   59

Q2LAB1
                                                               (SEQ ID NO: 10)
MKLVKLSLVAALAAGAFSAANATPLEEAIKDVDVSGVLRYRYDTGNFDKNFVN-NSNLNN   59

Q2LAB8
                                                               (SEQ ID NO: 11)
MKLVKLSLVAALAAGAFSAANATPLEEAIKDVDVSGVLRYRYDTGNFDKNFVN-NSNLNN   59

Q2LAA5
                                                               (SEQ ID NO: 12)
MKLVKLSLVAALAAGAFSAANATPLEEAIKDVDVSGVLRYRYDTGNFDKNFVN-NSNLNN   59

Q2LAB6
                                                               (SEQ ID NO: 13)
MKLVKLSLVAALAAGAFSAANATPLEEAIKDVDVSGVLRYRYDTGNFDKNFVN-NSNLNN   59

Q2LA95
                                                               (SEQ ID NO: 14)
MKLVKLSLVAALAAGAFSAANATPLEEAIKDVDVSGVLRYRYDTGNFDKNFVN-NSNLNN   59

P80672
                                                               (SEQ ID No. 1)
MKLVKLSLVAALAAGAFSAANATPLEEAIKDVDVSGVLRYRYDTGNFDKNFVN-NSNLNN   59
```

Q2LAC5

(SEQ ID NO: 15)

MKLVKLSLVAALAAGAFSAANATPLEEAIKDVDVSGVLRYRYDTGNFDKNFVN-NSNLNN  59

Q2LAA2

(SEQ ID NO: 16)

MKLVKLSLVAALAAGAFSAANATPLEEAIKDVDVSGVLRYRYDTGNFDKNFVN-NSNLNN  59

Q2LAB7

(SEQ ID NO: 17)

MKLVKLSLVAALAAGAFSAANATPLEEAIKDVDVSGVLRYRYDTGNFDKNFVN-NSNLNN  59

Q2LAB9

(SEQ ID NO: 18)

MKLVKLSLVAALAAGAFSAANATPLEEAIKDVDVSGVLRYRYDTGNFDKNFVN-NSNLNN  59

Q2LA91

(SEQ ID NO: 19)

MKLVKLSLVAALAAGAFSAANATPLEEAIKDVDVSGVLRYRYDTGNFDKNFVN-NSNLNN  59

NB2

(SEQ ID NO: 20)

MKLVKLSLVAALAAGAFSAANATPLEEAIKDVDVSGVLRYRYDTGNFDKNFVN-NSNLNN  59

Q2LA98

(SEQ ID NO: 21)

MKLVKLILVAALAAGAFSAANATPLEEAIKDVDVSGVLRYRYDTGNFDKNFVN-NSNLNN  59

A3ZHA2

(SEQ ID NO: 22)

MKLVKLSLVAALAAGAFSAANATPLEEAIKDVDVSGVLRYRYDTGNFDKNFVN-NSNLNN  59

Q9F792

(SEQ ID NO: 23)

MKLVKLSLVAALAAGAFSAANATPLEEAIKDVDVSGVLRYRYDTGNFDKNFVN-NSNLNN  59

Q2LAC0

(SEQ ID NO: 24)

MKLVKLSLVAALAAGAFSAANATPLEEAIKDVDVSGVLRYRYDTGNFDKNFVN-NSNLNN  59

Q0GF63

(SEQ ID NO: 25)

MKLVKLSLVAALAAGAFSAANATPLEEAIKDVDVSGVLRYRYDTGNFDKNFVN-NSNLNN  59

Q2LAB3

(SEQ ID NO: 26)

MKLVKLSLVAALAAGAFSAANATPLEEAIKDVDVSGVLRYRYDTGNFDKNFVN-NSNLNN  59

Q2LA93

(SEQ ID NO: 27)

MKLVKLSLVAALAAGAFSAANATPLEEAIKDVDVSGVLRYRYDTGTFDKNWGTPNSNLND  60

Q2LAA0

(SEQ ID NO: 28)

MKLVKLSLVAALAAGAFSAANATPLEEAIKDVDVSGVLRYRYDTGTFDKNWGTPNSNLND  60

Q2LAC1

(SEQ ID NO: 29)

MKLVKLSLVAALAAGAFSAANATPLEEAIKDVDVSGVLRYRYDTGTFDKNWGTPNSNLND  60

Q2LAC4

(SEQ ID NO: 30)

MKLVKLSLVAALAAGAFSAANATPLEEAIKDVDVSGVLRYRYDTGTFDKNWGTPNSNLND  60

Q2LA94

(SEQ ID NO: 31)

MKLVKLSLVAALAAGAFSAANATPLEEAIKDVDVSGVLRYRYDTGTFDKNWGTPNSNLND  60

Q2LA92

(SEQ ID NO: 32)

MKLVKLSLVAALAAGAFSAANATPLEEAIKDVDVSGVLRYRYDTGNFDKNFLN-NSNLNN  59

Q2LAA4

(SEQ ID NO: 33)

MKLVKLSLVAALAAGAFSAANATPLEEAIKDVDVSGVLRYRYDTGNFDKNFIN-NSNLNN  59

Q2LA89

(SEQ ID NO: 34)

MKLVKLSLVAALAAGAFSAANATPLEEAIKDVDVSGVLRYRYDTGNFDKNFIN-NSNLNN  59

-continued

NB3
(SEQ ID NO: 35)
MKLVKLSLVAALAAGAFSAANATPLEEAIKDVDVSGVLRYRYETSN-DWSNANFGSGIS-    58

Q2LAA9
(SEQ ID NO: 36)
MKLVKLSLVAALAAGAFSAANATPLEEAIKDIDVSGVLRYRYETSN-DWSNANFGSGIS-    58

B5QHE5
(SEQ ID NO: 37)
MKLVKLSLVAALAASAFSAANATPLEEAIKDIDVSGVLRYRYESSN-PWSNANFGSGIS-    58

Q2LA96
(SEQ ID NO: 38)
MKLVKLSLVAALAASAFSAANATPLEEAIKDIDVSGVLRYRYESSN-PWSNANFGSGIS-    58

Q2LAB4
(SEQ ID NO: 39)
MKLVKLSLVAALAASAFSAANATPLEEAIKDIDVSGVLRYRYESSN-PWSNANFGSGIS-    58

Q2LA97
(SEQ ID NO: 40)
MKLVKLSLVAALAASAFSAANATPLEEAIKDIDVSGVLRYRYESSN-PWSNANFGSGIS-    58

Q2LAA7
(SEQ ID NO: 41)
MKLVKLSLVAALAAGAFSAANATPLEEAIKDIDVSGVLRYRYESSN-PWSNANFGSGIS-    58

Q9F788
(SEQ ID NO: 42)
MKLVKISLVAALAAGAFSAANATPLEEAIKDIDVSGVLRYRYESSN-PWSNANFGSGIS-    58

Q2LA87
(SEQ ID NO: 43)
MKLVKLSLVAALAAGAFSAANATPLEEAIKDIDVSGVLRYRYESSN-PWSNANFGSGIS-    58

Q2LA90
(SEQ ID NO: 44)
MKLVKLSLVAALAAGAFSAANATPLEEAIKDIDVSGVLRYRYESSN-PWSNANFGSGIS-    58

Q2LAA3
(SEQ ID NO: 45)
MKLVKLSLVAALAAGAFSAANATPLEEAIKDIDVSGVLRYRYESSN-PWSNGNYGSGIS-    58

Q0GF62
(SEQ ID NO: 46)
MKLVKLSLVAALAAGAFSAANATPLEEAIKDIDVSGVLRYRYDTSN-DWNNAGFGSGIS-    58

***:***.************:********:::..  .   .*.:.

Hb1
(SEQ ID NO: 2 cont'd)
SKQDHKYRAQVNFSAAIADNFKAFVQFDYNAADGGY----GANGIKNDQKGLFVRQLYLT    115

Q2LAB2
(SEQ ID NO: 3 cont'd)
SKQDHKYRAQVNFSAAIADNFKAFVQFDYNAADGGY----GANGIKNDQKGLFVRQLYLT    115

Q2LAB0
(SEQ ID NO: 4 cont'd)
SKQDHKYRAQVNFSAAIADNFKAFVQFDYNAADGGY----GANGIKNDQKGLFVRQLYLT    115

Hb2
(SEQ ID NO: 5 cont'd)
SKQDHKYRAQVNFSAAIADNFKAFVQFDYNAADGGY----GANGIKNDQKGLFVRQLYLT    115

NB1
(SEQ ID NO: 6 cont'd)
SKQDHKYRAQVNFSAAIADNFKAFVQFDYNAADGGY----GANGIKNDQKGLFVRQLYLT    115

Q9F791
(SEQ ID NO: 7 cont'd)
SKQDHKYRAQVNFSAAIADNFKAFVQFDYNAADGGY----GANGIKNDQKGLFVRQLYLT    115

Hb3
(SEQ ID NO: 8 cont'd)
SKQDHKYRAQVNFSAAIADNFKAFVQFDYNAADGGY----GANGIKNDQKGLFVRQLYLT    115

```
D3FNB0
                                                     (SEQ ID NO: 9 cont'd)
SKQNHKYRAQVNFSAAIADNFKAFIQFDYNAADGGY----GANGIKNDQKGLFVRQLYLT  115

Q2LAB1
                                                    (SEQ ID NO: 10 cont'd)
SKQDHKYRAQVNFSAAIADNFKAFVQFDYNAADGGY----GANGIKNDQKGLFVRQLYLT  115

Q2LAB8
                                                    (SEQ ID NO: 11 cont'd)
SKQDHKYRAQVNFSAAIADNFKAFVQFDYNAADGGY----GANGIKNDQKGLFVRQLYLT  115

Q2LAA5
                                                    (SEQ ID NO: 12 cont'd)
SKQDHKYRAQVNFSAAIADNFKAFVQFDYNAADGGY----GANGIKNDQKGLFVRQLYLT  115

Q2LAB6
                                                    (SEQ ID NO: 13 cont'd)
SKQDHKYRAQVNFSAAIADNFKAFVQFDYNAADGGY----GANGIKNDQKGLFVRQLYLT  115

Q2LA95
                                                    (SEQ ID NO: 14 cont'd)
SKQDHKYRAQVNFSAAIADNFKAFVQFDYNAADGGY----GANGIKNDQKGLFVRQLYLT  115

P80672
                                                     (SEQ ID NO: 1 cont'd)
SKQDHKYRAQVNFSAAIADNFKAFVQFDYNAADGGY----GANGIKNDQKGLFVRQLYLT  115

Q2LAC5
                                                    (SEQ ID NO: 15 cont'd)
NKQDHKYRAQVNFSAAIADNFKAFIQFDYNAVDGGT----GVNNVKNAEKGLFVRQLYLT  115

Q2LAA2
                                                    (SEQ ID NO: 16 cont'd)
NKQDHKYRAQVNFSAAIADNFKAFIQFDYNAVDGGT----GVDNVTNAEKGLFVRQLYLT  115

Q2LAB7
                                                    (SEQ ID NO: 17 cont'd)
NKQDHKYRAQVNFSAAIADDFKAFIQFDYNAVDGGT----GVDNVTNAEKGLFVRQLYLT  115

Q2LAB9
                                                    (SEQ ID NO: 18 cont'd)
SKQDHKYRAQVNFSAAIADNFKAFIQFDYNAVDGGT----GVDNVTNTEKGLFVRQLYLT  115

Q2LA91
                                                    (SEQ ID NO: 19 cont'd)
NKQDHKYRAQVNFSAAIADNFKAFIQFDYNAVDGGT----GVDNVTNAEKGLFVRQLYLT  115

NB2
                                                    (SEQ ID NO: 20 cont'd)
NKQDHKYRAQVNFSAAIADNFKAFIQFDYNAVDGGT----GVDNVTNAEKGLFVRQLYLT  115

Q2LA98
                                                    (SEQ ID NO: 21 cont'd)
NKQDHKYRAQVNFSAAIADNFKAFIQFDYNAVDGGT----GVDNVTNAEKGLFVRQLYLT  115

A3ZHA2
                                                    (SEQ ID NO: 22 cont'd)
NKQDHKYRAQVNFGAAIADNFKAFIQFDYNAVDGGT----GVDNVTNAEKGLFVRQLYLT  115

Q9F792
                                                    (SEQ ID NO: 23 cont'd)
NKQDHKYRAQVNFGAAIADNFKAFIQFDYNAVDGGT----GVDNVTNAEKGLFVRQLYLT  115

Q2LAC0
                                                    (SEQ ID NO: 24 cont'd)
NKQDHKYRAQVNFGAAIADNFKAFIQFDYNAVDGGT----GVGNVKNAEKGLFVRQLYLT  115

Q0GF63
                                                    (SEQ ID NO: 25 cont'd)
NKQDHKYRAQVNFSAAIADNFKAFIQFDYNAVDGGT----GVDNVTNAEKGLFVRQLYLT  115

Q2LAB3
                                                    (SEQ ID NO: 26 cont'd)
NKQDHKYRAQVNFSAAIADNFKAFIQFDYNAVDGGT----GVDNATNAEKGLFVRQLYLT  115

Q2LA93
                                                    (SEQ ID NO: 27 cont'd)
SKQDHKYRAQVNFSAAIADNFKAFIQFDYNAVDGGT----GVDNKTNAEKGLFVRQLYLT  116
```

```
Q2LAA0
                                                (SEQ ID NO: 28 cont'd)
SKQDHKYRAQVNFSAAIADNFKAFIQFDYNAVDGGT----GVDNKTNAEKGLFVRQLYLT  116

Q2LAC1
                                                (SEQ ID NO: 29 cont'd)
SKQDHKYRAQVNFSAAIADNFKAFVQFDYNAVDGGT----GVDNATNAQKGFFVRQLYLT  116

Q2LAC4
                                                (SEQ ID NO: 30 cont'd)
SKQDHKYRAQVNFSAAIADNFKAFVQFDYNAVDGGT----GVDNATNAQKGFFVRQLYLT  116

Q2LA94
                                                (SEQ ID NO: 31 cont'd)
SKQDHKYRAQVNFSAAIADNFKAFIQFDYNAVDGGT----GVDNATNAEKGLFVRQLYLT  116

Q2LA92
                                                (SEQ ID NO: 32 cont'd)
SKQDHKYRAQVNFSAAIADNFKAFVQFDYNAVDGGT----GVDNATNAEKGLFVRQLYLT  115

Q2LAA4
                                                (SEQ ID NO: 33 cont'd)
SKQDHKYRAQVNFSAAIADNFKAFVQFDYNAADGGT----GVDNATNAQKGLFVRQLYLT  115

Q2LA89
                                                (SEQ ID NO: 34 cont'd)
SKQDHKYRAQVNFSAAIADNFKAFVQFDYNAADGGY----GANEIKNDQKGLFVRQLYLT  115

NB3
                                                (SEQ ID NO: 35 cont'd)
GKQDHKYRAQVNFGAASADNFKAFVQFDYSQADGGY----GADSISNTSDTLSVRQLYLT  114

Q2LAA9
                                                (SEQ ID NO: 36 cont'd)
GKQDHKYRAQVNFSGAISDNFKAFVQFDYNSQDGGY----GADSISNTSDTLSVRQLYLT  114

B5QHE5
                                                (SEQ ID NO: 37 cont'd)
GKQDHKYRAQVNFSGAISDNFKAFVQFDYNSQDGGY----GADSISNTSDTLSVRQLYLT  114

Q2LA96
                                                (SEQ ID NO: 38 cont'd)
GKQDHKYRAQVNFSGAISDNFKAFVQFDYNSQDGGY----GADSISNTSDTLSVRQLYLT  114

Q2LAB4
                                                (SEQ ID NO: 39 cont'd)
GKQDHKYRAQVNFSGAISDNFKAFVQFDYNSQDGGY----GTDSISNTSDTLTVRQLYLT  114

Q2LA97
                                                (SEQ ID NO: 40 cont'd)
GKQDHKYRAQVNFSGAISDNFKAFVQFDYNSQDGGY----GTDSISNTSDTLTVRQLYLT  114

Q2LAA7
                                                (SEQ ID NO: 41 cont'd)
GKQDHKYRAQVNFSGAISDNFKAFVQFDYNSQDGGY----GTDSISNTSDTLTVRQLYLT  114

Q9F788
                                                (SEQ ID NO: 42 cont'd)
GKQDHKYRAQVNFSGAISDNFKAFVQFDYNSQDGGY----GTDSISNTSDTLTVRQLYLT  114

Q2LA87
                                                (SEQ ID NO: 43 cont'd)
GKQDHKYRAQVNFSGAISDNFKAFVQFDYNSQDGGY----GTDSISNTSDTLTVRQLYLT  114

Q2LA90
                                                (SEQ ID NO: 44 cont'd)
GKQDHKYRAQVNFSGAISDNFKAFVQFDYNSQDGGY----GADSISNTSDTLTVRQLYLT  114

Q2LAA3
                                                (SEQ ID NO: 45 cont'd)
GKQDHKYRAQVNFNTAIADNFKAFVQFDYNSKDGGY----GENSISNTSDTLSVRQLYLT  114

Q0GF62
                                                (SEQ ID NO: 46 cont'd)
GKQTHNYRAQINFSGAIADNFKAFVQFDYAAVDGGYNVTNGTGNQRNDQNSLTVRQLYLT  118

.** *:****:**. * :*:****:****   ***    *  .  * .. : *******
Hb1
                                                (SEQ ID NO: 2 cont'd)
YTNEDVATSVIAGKQQLNLIWTDNAIDGLVGTGVKVVNNSIDGLTLAAFAVDSFMAAEQG  175
```

-continued

Q2LAB2
(SEQ ID NO: 3 cont'd)
YTNEDVATSVIAGKQQLNLIWTDNAIDGLVGTGVKVVNNSIDGLTLAAFAVDSFMAAEQG 175

Q2LAB0
(SEQ ID NO: 4 cont'd)
YTNEDVATSVIAGKQQLNLIWTDNAIDGLVGTGVKVVNNSIDGLTLAAFAVDSFMAAEQG 175

Hb2
(SEQ ID NO: 5 cont'd)
YTNEDVATSVIAGKQQLNTIWTDNGVDGLVGTGIKVVNNSIDGLTLAAFAVDSFMAEEQG 175

NB1
(SEQ ID NO: 6 cont'd)
YTNEDVATSVIAGKQQLNTIWTDNGVDGLVGTGIKVVNNSIDGLTLAAFAVDSFMAEEQG 175

Q9F791
(SEQ ID NO: 7 cont'd)
YTNEDVATSVIAGKQQLNTIWTDNGVDGLVGTGIKVVNNSIDGLTLAAFAVDSFMAEEQG 175

Hb3
(SEQ ID NO: 8 cont'd)
YTNEDVATSVIAGKQQLNTIWTDNGVDGLVGTGIKVANNSIDGLTLAAFAVDSFMAEEQG 175

D3FNB0
(SEQ ID NO: 9 cont'd)
YTNEDVATSVIAGKQQLNTIWTDNGVDGLVGTGIKVVNNSIDGLTLAAFAVDSFMAEEQG 175

Q2LAB1
(SEQ ID NO: 10 cont'd)
YTNEDVATSVIAGKQQLNTIWTDNGVDGLVGTGIKVVNNSIDGLTLAAFAVDSFMAEEQG 175

Q2LAB8
(SEQ ID NO: 11 cont'd)
YTNEDVATSVIAGKQQLNTIWTDNGVDGLVGTGIKVVNNSIDGLTLAAFAVDSFMAEEQG 175

Q2LAA5
(SEQ ID NO: 12 cont'd)
YTNEDVATSVIAGKQQLNTIWTDNGVDGLVGTGIKVVNNSIDGLTLAAFAVDSFMAEEQG 175

Q2LAB6
(SEQ ID NO: 13 cont'd)
YTNEDVATSVIAGKQQLNTIWTDNGVDGLVGTGIKVVNNSIDGLTLAAFAVDSFMAEEQG 175

Q2LA95
(SEQ ID NO: 14 cont'd)
YTNEDVATSVIAGKQQLNTIWTDNGVDGLVGTGIKVVNNSIDGLTLAAFAVDSFMAAEQG 175

P80672
(SEQ ID NO: 1 cont'd)
YTNEDVATSVIAGKQQLNLIWTDNAIDGLVGTGVKVVNNSIDGLTLAAFAVDSFMAAEQG 175

Q2LAC5
(SEQ ID NO: 15 cont'd)
YTNEDVATSVIAGKQQLNLIWTDNAIDGLVGTGVKVVNNSIDGLTLAAFAADSFMAAEQG 175

Q2LAA2
(SEQ ID NO: 16 cont'd)
YTNEDVATSVIAGKQQLNLIWTDNAIDGLVGTGVKVVNNSIDGLTLAAFAADSFMAAEQG 175

Q2LAB7
(SEQ ID NO: 17 cont'd)
YTNEDVATSVIAGKQQLNLIWTDNAIDGLVGTGVKVVNNSIDGLTLAAFAADSFMAAEQG 175

Q2LAB9
(SEQ ID NO: 18 cont'd)
YTNEDVATSVIAGKQQLNLIWTDNAIDGLVGTGVKVVNNSIDGLTLAAFAADSFMAAEQG 175

Q2LA91
(SEQ ID NO: 19 cont'd)
YTNEDVATSVIAGKQQLNLIWTDNAIDGLVGTGVKVVNNSIDGLTLAAFAVDSFMAAEQG 175

NB2
(SEQ ID NO: 20 cont'd)
YTNEDVATSVIAGKQQLNLIWTDNAIDGLVGTGIKVVNNSIDGLTLAAFAADSFMAAEQG 175

Q2LA98
(SEQ ID NO: 21 cont'd)
YTNEDVATSVIAGKQQLNLIWTDNAIDGLVGTGIKVVNNSIDGLTLAAFAADSFMAAEQG 175

A3ZHA2

(SEQ ID NO: 22 cont'd)
YTNEDVATSVIAGKQQLNLIWTDNAIDGLVGTGVKVVNNSIDGLTLAAFAADSFMAAEQG 175

Q9F792

(SEQ ID NO: 23 cont'd)
YTNEDVATSVIAGKQQLNLIWTDNAIDGLVGTGVKVVNNSIDGLTLAAFAADSFMAAEQG 175

Q2LAC0

(SEQ ID NO: 24 cont'd)
YTNEDVATSVIAGKQQLNLIWTDNAIDGLVGTGVKVVNNSIDGLTLAAFAADSFMAAEQG 175

Q0GF63

(SEQ ID NO: 25 cont'd)
YTNEDVATSVIAGKQQLNFIWTDNAIDGLVGTGVKVVNNSIDGLTLAAFAVDSFMAAEQG 175

Q2LAB3

(SEQ ID NO: 26 cont'd)
YTNEDVATSVIAGKQQLNLIWTDNAIDGLVGTGVKVVNNSIDGLTLAAFAVDSFMTAEQG 175

Q2LA93

(SEQ ID NO: 27 cont'd)
YTNEDVATSVIAGKQQLNIIWTDNGVDGLVGTGIKVVNNSIDGLTLAAFAVDSFMAAEQG 176

Q2LAA0

(SEQ ID NO: 28 cont'd)
YTNEDVATSVIAGKQQLNIIWTDNGVDGLVGTGIKVVNNSIDGLTLAAFAVDSFMAAEQG 176

Q2LAC1

(SEQ ID NO: 29 cont'd)
YTNEDVATSVIAGKQQLNIIWTDNGIDGLVGTGVKVVNNSIDGLTLAAFAVDSFMATEQG 176

Q2LAC4

(SEQ ID NO: 30 cont'd)
YTNEDVATSVIAGKQQLNIIWTDNGIDGLVGTGVKVVNNSIDGLTLAAFAVDSFMATEQG 176

Q2LA94

(SEQ ID NO: 31 cont'd)
YTNEDVATSVIAGKQQLNTIWTDNGIDGLVGTGVKVVNNSIDGLTLAAFAVDSFMATEQG 176

Q2LA92

(SEQ ID NO: 32 cont'd)
YTNEDVATSVIAGKQQLNIIWTDNGVDGLVGTGVKVVNNSIDGLTLAAFAVDSFMATEQG 175

Q2LAA4

(SEQ ID NO: 33 cont'd)
YTNEDVATSVIAGKQQLNTIWTDNGIDGLVGTGVKVVNNSIDGLTLAAFAVDSFMAEEQG 175

Q2LA89

(SEQ ID NO: 34 cont'd)
YTNEDVATSVIAGKQQLNTIWTDNGIDGLVGTGVKVINNSIDGLTLAAFAVDSFMAAEQG 175

NB3

(SEQ ID NO: 35 cont'd)
YTNEDVATSVIAGKQQLNTIWTDNGIDGLVGTGIKVVNNSIDGLTLAAFAMDSFNEEVPA 174

Q2LAA9

(SEQ ID NO: 36 cont'd)
YTNEDVATSVIAGKQQLNTIWTDNGIDGLVGTGIKVVNNSIDGLTLAAFAMDSFNEEVPA 174

B5QHE5

(SEQ ID NO: 37 cont'd)
YTNEDVATSVIAGKQQLNTIWTDNAIDGLVGTGIKVVNNSIDGLTLAAFAMDSFNEASDT 174

Q2LA96

(SEQ ID NO: 38 cont'd)
YTNEDVATSVIAGKQQLNTIWTDNAIDGLVGTGIKVVNNSIDGLTLAAFAMDSFNEASDT 174

Q2LAB4

(SEQ ID NO: 39 cont'd)
YTNEDVATSVIAGKQQLNTIWTDNGIDGLVGTGVKVVNNSIDGLTLAAFAMDSFNEASDT 174

Q2LA97

(SEQ ID NO: 40 cont'd)
YTNEDVATSVIAGKQQLNTIWTDNGVDGLVGTGIKVVNNSIDGLTLAAFAMDSFNEASDT 174

Q2LAA7

(SEQ ID NO: 41 cont'd)
YTNEDVATSVIAGKQQLNTIWTDNGIDGLVGTGVKVVNNSIDGLTLAAFAMDSFNEASDT 174

-continued

Q9F788
(SEQ ID NO: 42 cont'd)
YTNEDVATSVIAGKQQLNTIWTDNGIDGLVGTGVKVVNNSIDGLTLAAFAMDSFNEASDT 174

Q2LA87
(SEQ ID NO: 43 cont'd)
YTNEDVATSVIAGKQQLNTIWTDNAIDGLVGTGVKVVNNSIDGLTLAAFAMDSFNEASDT 174

Q2LA90
(SEQ ID NO: 44 cont'd)
YTNEDVATSVIAGKQQLNFIWTDNAIDGLVGTGIKVVNNSIDGLTLAAFAMDSFNEASDT 174

Q2LAA3
(SEQ ID NO: 45 cont'd)
YTNEDVATSVIAGKQQLNTIWTDNGVDGLVGTGIKVVNNSIDGLTLAAFAMDSFNEASDT 174

Q0GF62
(SEQ ID NO: 46 cont'd)
YTNEDVATSVIAGKQQLNTIWTDNDIDGLVGTGIKVVNNSIDGLTLAAFAVDSYNTDE-- 176

*************** * :***: *********** :

Hb1
(SEQ ID NO: 2 cont'd)
AD----------LLGHS-TTS----TTQKAAPFKVDSVGNLYGAAAVGSYDLAGGQFNPQ 220

Q2LAB2
(SEQ ID NO: 3 cont'd)
AD----------LLGHS-TTSTTH-TTQKAAPFKVDSVGNLYGAAAVGSYDLAGGQFNPQ 223

Q2LAB0
(SEQ ID NO: 4 cont'd)
AD----------LLGHS-TTS----TTQKAAPFKVDSVGNLYGAAAVGSYDLAGGQFNPQ 220

Hb2
(SEQ ID NO: 5 cont'd)
AD----------LLGQS-TIS----TTQNAAPFKVDSVGNLYGAAAVGSYDLAGGQFNPQ 220

NB1
(SEQ ID NO: 6 cont'd)
AD----------LLGQS-TIS----TTQNAAPFKVDSVGNLYGAAAVGSYDLAGGQFNPQ 220

Q9F791
(SEQ ID NO: 7 cont'd)
AD----------LLGQS-TIS----TTQNAAPFKVDSVGNLYGAAAVGSYDLAGGQFNPQ 220

Hb3
(SEQ ID NO: 8 cont'd)
AD----------LLGQS-TIS----TTQNAAPFKVDSVGNLYGAAAVGSYDLAGGQFNPQ 220

D3FNB0
(SEQ ID NO: 9 cont'd)
AD----------LLGKS-TIS----TTQKAAPFQADSLGNLYGAAAVGSYDLAGGQFNPQ 220

Q2LAB1
(SEQ ID NO: 10 cont'd)
AD----------LLGQS-TIS----TTQKAAPFQADSLGNLYGAAAVGSYDLAGGQFNPQ 220

Q2LAB8
(SEQ ID NO: 11 cont'd)
AD----------LLGQS-TIS----TTQKAAPFQADSLGNLYGAAAVGSYDLAGGQFNPQ 220

Q2LAA5
(SEQ ID NO: 12 cont'd)
TD----------LLGQS-TIS----TTQNTAPFQADSLGNLYGAAAVGSYDLAGGQFNPQ 220

Q2LAB6
(SEQ ID NO: 13 cont'd)
TD----------LLGQS-TIS----TTQNTALFQADSLGNLYGAAAVGSYDLAGGQFNPQ 220

Q2LA95
(SEQ ID NO: 14 cont'd)
AD----------LLGHSNTST----ATPNQVPFKVDSVGNLYGAAAVGSYDLAGGQFNPQ 221

P80672
(SEQ ID No: 1 cont'd)
AD----------LLEHS-NIS----TTSNQAPFKVDSVGNLYGAAAVGSYDLAGGQFNPQ 220

Q2LAC5
(SEQ ID NO: 15 cont'd)
AD----------LLGHS-NIS----TTSKQAPFKVDSVGNLYGAAAVGSYDLAGGQFNPQ 220

```
Q2LAA2
                                                (SEQ ID NO: 16 cont'd)
AD----------LLGHS-TTSTT----QATAPFKVDSVGNLYGAAAVGSYDLAGGQFNPQ  220

Q2LAB7
                                                (SEQ ID NO: 17 cont'd)
AD----------LLGHS-TTSTT----QATAPFKVDSVGNLYGAAAVGSYDLAGGQFNPQ  220

Q2LAB9
                                                (SEQ ID NO: 18 cont'd)
AD----------LLEHS-TISTT----QNAAPFKVDSVGNLYGAAAVGSYDLAGGQFNPQ  220

Q2LA91
                                                (SEQ ID NO: 19 cont'd)
AD----------LLGHS-NISTT---NANQAPFKVDSVGNLYGAAAVGSYDLAGGQFNPQ  221

NB2
                                                (SEQ ID NO: 20 cont'd)
AD----------LLGHS-NIST----TPNQAPFKVDSVGNLYGAAAVGSYDLAGGQFNPQ  220

Q2LA98
                                                (SEQ ID NO: 21 cont'd)
AD----------LLGHR-NISTI---TPNQAPFKVDSVGNLYGAAAVGSYDLAGGQFNPQ  221

A3ZHA2
                                                (SEQ ID NO: 22 cont'd)
AD----------LLGHS-NISTT---S-NQVPFKVDSVGNLYGAAAVGSYDLAGGQFNPQ  220

Q9F792
                                                (SEQ ID NO: 23 cont'd)
AD----------LLGHS-NISTT---S-NQAPFKVDSVGNLYGAAAVGSYDLAGGQFNPQ  220

Q2LAC0
                                                (SEQ ID NO: 24 cont'd)
AD----------LLGHS-NTSTA---TPNQAPFKVDSVGNLYGAAAVGSYDLAGGQFNPQ  221

Q0GF63
                                                (SEQ ID NO: 25 cont'd)
AE----------LLGHS-NIS----TTSNQAPFKVDSVGNLYGAAAVGSYDLAGGQFNPQ  220

Q2LAB3
                                                (SEQ ID NO: 26 cont'd)
AD----------LLGHN-----------GSQFNPDSIGNLYGAAAVGSYDLAGGQFNPQ  213

Q2LA93
                                                (SEQ ID NO: 27 cont'd)
SD----------LVG-----------ANN-TFKVDSIGNLYGAAAVGSYDLAGGQFNPQ  213

Q2LAA0
                                                (SEQ ID NO: 28 cont'd)
SD----------LVG-----------ANNSTFKVDSIGNLYGAAAVGSYDLAGGQFNPQ  214

Q2LAC1
                                                (SEQ ID NO: 29 cont'd)
SD----------LVG-----------HNGSQFNPDSIGNLYGAAAVGSYDLAGGQFNPQ  214

Q2LAC4
                                                (SEQ ID NO: 30 cont'd)
SD----------LVG-----------HNGSQFNPDSIGNLYGAAAVGSYDLAGGQFNPQ  214

Q2LA94
                                                (SEQ ID NO: 31 cont'd)
SD----------LVG-----------HNGSKFSPDSIGNLYGAAAVGSYDLAGGQFNPQ  214

Q2LA92
                                                (SEQ ID NO: 32 cont'd)
SD----------LLGQSTYVSND---KNNNDSFKLDSIGNLYGAAAVGSYDLAGGQFNPQ  222

Q2LAA4
                                                (SEQ ID NO: 33 cont'd)
AD----------LLGHS-NIS--S-AN-NSAPFKLDSIGNLYGGAAVGSYEFLGGQFNPQ  220

Q2LA89
                                                (SEQ ID NO: 34 cont'd)
AD----------LLGHS-NIS--S-AKPNIAPFKLDSIGNLYGGAAVGSYEFLGGQFNPQ  221

NB3
                                                (SEQ ID NO: 35 cont'd)
TT-----------TNG-FNKGNV--NGDGDVSSALDWSKNIYGAAAIGSYDLIGGQFNPQ  220
```

-continued

Q2LAA9

(SEQ ID NO: 36 cont'd)
TT----------TNGNFNKGNV--NGDGDVSSALDWSKNIYGAAAIGSYDIAGGQFNPQ 221

B5QHE5

(SEQ ID NO: 37 cont'd)
TVTITQD-NSQKITGVQFNRGNP--KGDSDVSGALDWSKNIYGAAAIGSYDIAGGQFNPQ 231

Q2LA96

(SEQ ID NO: 38 cont'd)
TVTITQD-NSQKITGVQFNRGNP--KGDSDVSGALDWSKNIYGATAIGSYDIAGGQFNPQ 231

Q2LAB4

(SEQ ID NO: 39 cont'd)
TVTITQD-SNQKITGVQFNRGNP--KGDSDVSGALDWSKNIYGAAAIGSYDIAGGQFNPQ 231

Q2LA97

(SEQ ID NO: 40 cont'd)
TVTITQN-SSQKITGVQFNRGNP--KGDGDVSGALDWSKNIYGAAAIGSYDITGGQFNPQ 231

Q2LAA7

(SEQ ID NO: 41 cont'd)
TVTITQD-NNQKITGVQFNRGNP--KGDSDVSGALDWSKNIYGAAAIGSYDIAGGQFNPQ 231

Q9F788

(SEQ ID NO: 42 cont'd)
TVTITQD-NNQKITGVQFNRGNP--KGDSDVSGALDWSKNIYGAAAIGSYDIAGGQFNPQ 231

Q2LA87

(SEQ ID NO: 43 cont'd)
TVTITQD-NNQKITGVQFNRGNP--KGDSDVSGALDWSKNIYGAAAIGSYDIAGGQFNPQ 231

Q2LA90

(SEQ ID NO: 44 cont'd)
TVTITQN-GSQKITGVQFNRGNP--KGDGDASGALDWSKNIYGAAAIGSYDLAGGQFNPQ 231

Q2LAA3

(SEQ ID NO: 45 cont'd)
TVIITQDPSSNKITGVQFNRGNP--KGDGDVSGALDWSKNIYGAAAIGSYDIAGGQFNPQ 232

Q0GF62

(SEQ ID NO: 46 cont'd)
-------------QGYKDNNGRPDLTYTGDASQYLTWG-NIYGAAAVGSYDLAGGQFNPQ 222

```
                    *:**.:*:***:: *******
                    (Ser 262) (Thr 268)
```

Hb1

(SEQ ID NO: 2 cont'd)
LWLAYWDQVAFFYAVDAAYSTTIFDGINWTLEGAYLGNSLDSELDDKTHAN--------- 271

Q2LAB2

(SEQ ID NO: 3 cont'd)
LWLAYWDQVAFFYAVDAAYSTTIFDGINWTLEGAYLGNSLDSELDDKTHAN--------- 274

Q2LAB0

(SEQ ID NO: 4 cont'd)
LWLAYWDQVAFFYAVDAAYSTTIFDGINWTLEGAYLGNSLDSELDDKTHAN--------- 271

Hb2

(SEQ ID NO: 5 cont'd)
LWLAYWDQVAFFYAVDAAYSTTIFDGINWTLEGAYLGNSLDSELDDKTHAN--------- 271

NB1

(SEQ ID NO: 6 cont'd)
LWLAYWDQVAFFYAVDAAYSTTIFDGINWTLEGAYLGNSLDSELDDKTHAN--------- 271

Q9F791

(SEQ ID NO: 7 cont'd)
LWLAYWDQVAFFYAVDAAYSTTIFDGINWTLEGAYLGNSLDSELDDKTHAN--------- 271

Hb3

(SEQ ID NO: 8 cont'd)
LWLAYWDQVAFFYAVDAAYSTTIFDGINWTLEGAYLGNSLDSELDDKTHAN--------- 271

D3FNB0

(SEQ ID NO: 9 cont'd)
LWLAYWDQVAFFYAVDAAYSTTIFDGINWTLEGAYLGNSLDSELNDKRHAN--------- 271

-continued

Q2LAB1
                                                  (SEQ ID NO: 10 cont'd)
LWLAYWDQVAFFYAVDAAYSTTIFDGINWTLEGAYLGNSLDSELDDKRHAN---------  271

Q2LAB8
                                                  (SEQ ID NO: 11 cont'd)
LWLAYWDQVAFFYAVDAAYSTTIFDGINWTLEGAYLGNSLDSELDDKTHAN---------  271

Q2LAA5
                                                  (SEQ ID NO: 12 cont'd)
LWLAYWDQVAFFYAVDAAYSTTIFDGINWTLEGAYLGNSLDSELDDKRHAN---------  271

Q2LAB6
                                                  (SEQ ID NO: 13 cont'd)
LWLAYWDQVAFFYAVDAAYSTTIFDGINWTLEGAYLGNSLDSELDDKRHAN---------  271

Q2LA95
                                                  (SEQ ID NO: 14 cont'd)
LWLAYWDQVAFFYAVDAAYSTTIFDGINWTLEGAYLGNSLDSELDDTTHAN---------  272

P80672
                                                  (SEQ ID No. 1 cont'd)
LWLAYWDQVAFFYAVDAAYSTTIFDGINWTLEGAYLGNSLDSELDDKTHAN---------  271

Q2LAC5
                                                  (SEQ ID NO: 15 cont'd)
LWLAYWDQVTFFYAVDAAYSTTIFDGINWTLEGAYLGNSLDSELDDKTHAN---------  271

Q2LAA2
                                                  (SEQ ID NO: 16 cont'd)
LWLAYWDQVAFFYAVDAAYSTTIFDGINWTLEGAYLGNSLDSELDDKTHAN---------  271

Q2LAB7
                                                  (SEQ ID NO: 17 cont'd)
LWLAYWDQVAFFYAVDAAYSTTIFDGINWTLEGAYLGNSLDSELDDKTHAN---------  271

Q2LAB9
                                                  (SEQ ID NO: 18 cont'd)
LWLAYWDQVAFFYAVDAAYSTTIFDGINWTLEGAYLGNSLDSELDDKTHAN---------  271

Q2LA91
                                                  (SEQ ID NO: 19 cont'd)
LWLAYWDQVAFFYAVDAAYSTTIFDGINWTLEGAYLGNSLDSELDDKTHAN---------  272

NB2
                                                  (SEQ ID NO: 20 cont'd)
LWLAYWDQVAFFYAVDAAYSTTIFDGINWTLEGAYLGNSLDSELDDKTHAN---------  271

Q2LA98
                                                  (SEQ ID NO: 21 cont'd)
LWLAYWDQVAFFYAVDAAYSTTIFDGINWTLEGAYLGNSLDSELDDKTHAN---------  272

A3ZHA2
                                                  (SEQ ID NO: 22 cont'd)
LWLAYWDQVAFFYAVDAAYSTTIFDGINWTLEGAYLGNSLDSELDDKTHAN---------  271

Q9F792
                                                  (SEQ ID NO: 23 cont'd)
LWLAYWDQVAFFYAVDAAYSTTIFDGINWTLEGAYLGNSLDSELDDQAHAN---------  271

Q2LAC0
                                                  (SEQ ID NO: 24 cont'd)
LWLAYWDQVAFFYAVDAAYSTTIFDGINWTLEGAYLGNSLDSELDDTTHAN---------  272

Q0GF63
                                                  (SEQ ID NO: 25 cont'd)
LWLAYWDQVAFFYAVDAAYSTTIFDGINWTIEGAYLGNSIDSELDDTTHTN---------  271

Q2LAB3
                                                  (SEQ ID NO: 26 cont'd)
LWLAYWDQVAFFYALDASYSTTIFDGINWTLEGAYLGNSVDSDLDSTRYAN---------  264

Q2LA93
                                                  (SEQ ID NO: 27 cont'd)
LWLAYWDQVAFFYAVDAAYSTTIFDGINWTLEGAYLGNSVDSDLNSAEHAN---------  264

Q2LAA0
                                                  (SEQ ID NO: 28 cont'd)
LWLAYWDQVAFFYALDVSYSTTIFDGINWTLEGAYLGNSLDSELNDKTYAN---------  265

-continued

Q2LAC1
(SEQ ID NO: 29 cont'd)
LWLAYWDQVAFFYALDASYSTTIFDGINWTLEGAYLGNSVDSDLDSAKYAN--------- 265

Q2LAC4
(SEQ ID NO: 30 cont'd)
LWLAYWDQVAFFYALDASYSTTIFDGINWTLEGAYLGNSVDSDLDSARYAN--------- 265

Q2LA94
(SEQ ID NO: 31 cont'd)
LWLAYWDQVAFFYALDASYSTTIFDGINWTLEGAYLGNSVDSDLNSAEYAN--------- 265

Q2LA92
(SEQ ID NO: 32 cont'd)
LWLAYWDQVAFFYAVDAAYSTTIFDGINWTLEGAYLGNSLDSELDDRTYAN--------- 273

Q2LAA4
(SEQ ID NO: 33 cont'd)
LWLAYWDQVAFFYAVDAAYSTTIFDGINWTLEGAYLGNSIDSELDKTTHTN--------- 271

Q2LA89
(SEQ ID NO: 34 cont'd)
LWLAYWDQVAFFYAVDAAYSTTIFDGINWTLEGAYLGNSIDSELDDKTHTN--------- 272

NB3
(SEQ ID NO: 35 cont'd)
LWLAYMSDNAFLYALDAAYSTTIFDGINWSIEGAYLGNSVDNKLKDRLDAA--------N 272

Q2LAA9
(SEQ ID NO: 36 cont'd)
LWLAYMSDNAFLYALDAAYSTTIFDGINWSIEGAYLGNSVDNKLKDRLDAA--------N 273

B5QHE5
(SEQ ID NO: 37 cont'd)
LWLAYMSDNAFLYALDATYSTTIFDGINWTIEGAYLGNSVDNKLKDRLDAA--------N 283

Q2LA96
(SEQ ID NO: 38 cont'd)
LWLAYMSDNAFLYALDATYSTTIFDGINWTIEGAYLGNSVDNKLKDRLDAA--------N 283

Q2LAB4
(SEQ ID NO: 39 cont'd)
LWLAYMSDNAFLYALDAAYSTTIFDGINWTIEGAYLGNSVDNKLKDRLDAA--------N 283

Q2LA97
(SEQ ID NO: 40 cont'd)
LWLAYMS DNAFLYALDAAYSTIFDGINWSIEGAYLGNSVDNKLKDRLGVA--------N 283

Q2LAA7
(SEQ ID NO: 41 cont'd)
LWLAYMSDNAFLYALDAAYSTTIFDGINWTIEGAYLGNSVDNKLKDRLDAA--------N 283

Q9F788
(SEQ ID NO: 42 cont'd)
LWLAYMSDNAFLYALDAAYSTTIFDGINWTIEGAYLGNSVDNKLKDRLDAA--------N 283

Q2LA87
(SEQ ID NO: 43 cont'd)
LWLAYMSDNAFLYALDAAYSTTIFNGINWTIEGAYLGNSVDNKLKDRLDAA--------N 283

Q2LA90
(SEQ ID NO: 44 cont'd)
LWLAYMSDNAFLYALDAAYSTTIFDGINWTIEGAYLGNSVDNKLKDRLNVA--------N 283

Q2LAA3
(SEQ ID NO: 45 cont'd)
LWLAYMSDNAFLYALDAAYNTTIFDGINWTIEGAYLGNSVDNKLKDRLDAA--------N 284

Q0GF62
(SEQ ID NO: 46 cont'd)
LWLAYMSDNAFLYALDLAYNTTIFDGINWSIEGAYLGNSVDNKLKDRFHAAGDPESSAAN 282

*****  .:  :*:**:*  :*.**:::******:*...*..  .
(Lys 273)

Hb1
(SEQ ID NO: 2 cont'd)
GNLFALKGSIEVNGWDASLGGLYYGDKEKASTVVIEDQGNLGSLLAGEEIFYTTGSRLNG 331

-continued

Q2LAB2

(SEQ ID NO: 3 cont'd)
GNLFALXGSIEVNGWDASLGGLYYGDKEKASTVVIEDQGNLGSLLAGEEIFYTTGSRLNG 334

Q2LAB0

(SEQ ID NO: 4 cont'd)
GNLFALKGSIEVNGWDASLGGLYYGDKEKASTVVIEDQGNLGSLLAGEEIFYTTGSRLNG 331

Hb2

(SEQ ID NO: 5 cont'd)
GNLFALKGSIEVNGWDASLGGLYYGDKEKASTVVIEDQGNLGSLLAGEEIFYTTGSRLNG 331

NB1

(SEQ ID NO: 6 cont'd)
GNLFALKGSIEVNGWDASLGGLYYGDKEKASTVVIEDQGNLGSLLAGEEIFYTTGSRLNG 331

Q9F791

(SEQ ID NO: 7 cont'd)
GNLFALKGSIEVNGWDASLGGLYYGDKEKASTVVIEDQGNLGSLLAGEEIFYTTGSRLNG 331

Hb3

(SEQ ID NO: 8 cont'd)
GNLFALKGSIEVNGWDASLGGLYYGDKEKASTVVIEDQGNLGSLLAGEEIFYTTGSRLNG 331

D3FNB0

(SEQ ID NO: 9 cont'd)
GNLFALKGSIEVNGWDASLGGLYYGDKEKASTVVIEDQGNLGSLLAGEEIFYTTGSRLNG 331

Q2LAB1

(SEQ ID NO: 10 cont'd)
GNLFALKGSIEVNGWDASLGGLYYGDKEKASTVVIEDQGNLGSLLAGEEIFYTTGSRLNG 331

Q2LAB8

(SEQ ID NO: 11 cont'd)
GNLFALXGTIEVNGWDASLGGLYYGDKEKASTVVIEDQGNLGSLLAGEEIFYTTGSRLNG 331

Q2LAA5

(SEQ ID NO: 12 cont'd)
GNLFALKGSIEVNGWDASLGGLYYGDKEKASTVVIEDQGNLGSLLAGEEIFYTTGSRLNG 331

Q2LAB6

(SEQ ID NO: 13 cont'd)
GNLFALKGSIEVNGWDASLGGLYYGDKEKASTVVIEDQGNLGSLLAGEEIFYTTGSRLNG 331

Q2LA95

(SEQ ID NO: 14 cont'd)
GNLFALKGSIEVNGWDASLGGLYYGDKEKASTVVIEDQGNLGSLLAGEEIFYTTGSRLNG 332

P80672

(SEQ ID NO: 1 cont'd)
GNLFALKGSIEVNGWDASLGGLYYGDKEKASTVVIEDQGNLGSLLAGEEIFYTTGSRLNG 331

Q2LAC5

(SEQ ID NO: 15 cont'd)
GNLFALXGTIEVNGWDASLGGLYYGDKEKASTVVIEDQGNLGSLLAGEEIFYTTGSRLNG 331

Q2LAA2

(SEQ ID NO: 16 cont'd)
GNLFALKGSIEVNGWDASLGGLYYGDKEKASTVVIEDQGNLGSLLAGEEIFYTTGSRLNG 331

Q2LAB7

(SEQ ID NO: 17 cont'd)
GNLFALKGSIEVNGWDASLGGLYYGDKEKASTVVIEDQGNLGSLLAGEEIFYTTGSRLNG 331

Q2LAB9

(SEQ ID NO: 18 cont'd)
GNLFALKGSIEVNGWDASLGGLYYGDKEKASTVVIEDQGNLGSLLAGEEIFYTTGSRLNG 331

Q2LA91

(SEQ ID NO: 19 cont'd)
GNLFALXGSIEVNGWDASLGGLYYGDKEKASTVVIEDQGNLGSLLAGEEIFYTTGSRLNG 332

NB2

(SEQ ID NO: 20 cont'd)
GNLFALKGSIEVNGWDASLGGLYYGDKEKASTVVIEDQGNLGSLLAGEEIFYTTGSRLNG 331

Q2LA98

(SEQ ID NO: 21 cont'd)
GNLFALKGSIEVNGWDASLGGLYYGDKEKASTVVIEDQGNLGSLLAGEEIFYTTGSRLNG 332

-continued

A3ZHA2
(SEQ ID NO: 22 cont'd)
GNLFALXGSIEVNGWDASLGGLYYGDKEKASTVVIEDQGNLGSLLAGEEIFYTTGSRLNG 331

Q9F792
(SEQ ID NO: 23 cont'd)
GNLFALKGSIEVNGWDASLGGLYYGDKEKASTVVIEDQGNLGSLLAGEEIFYTTGSRLNG 331

Q2LAC0
(SEQ ID NO: 24 cont'd)
GNLFALXGSIEVNGWDASLGGLYYGDKEKASTVVIEDQGNLGSLLAGEEIFYTTGSRLNG 332

Q0GF63
(SEQ ID NO: 25 cont'd)
GNFFALKGGIEVNGWDASLGGLYYGDKEKASTVVIEDQGNLSSLLAGEEIFYTTGSRLNG 331

Q2LAB3
(SEQ ID NO: 26 cont'd)
GNFFALXGGIEVNGWDASLGGLYYGDKEKASTVIIDDQGNLSSLLAGEEIFYTTGSRLNG 324

Q2LA93
(SEQ ID NO: 27 cont'd)
GNLFALXGSIEVNGWDASLGGLYYGDKEKASTVVIEDQGNLGSLLAGEEIFYTTGSRLNG 324

Q2LAA0
(SEQ ID NO: 28 cont'd)
GNLFALFGSIEVNGWDASLGGLYYGDKEKASTVAIEDQGNLGSLLAGEEIFYTTGSRLNG 325

Q2LAC1
(SEQ ID NO: 29 cont'd)
GNLFALXGSIEVNGWDASLGGLYYGDKEKASTVVIEDQGNLGSLLAGEEIFYTTGSRLNG 325

Q2LAC4
(SEQ ID NO: 30 cont'd)
GNLFALXGSIEVNGWDASLGGLYYGDKEKASTVVIEDQGNLGSLLAGEEIFYTTGSRLNG 325

Q2LA94
(SEQ ID NO: 31 cont'd)
GNLFALXGSIEVNGWDASLGGLYYGDKEKASTVVIEDQGNLGSLLAGEEIFYTTGSRLNG 325

Q2LA92
(SEQ ID NO: 32 cont'd)
GNLFALXGSIEVNGWDASLGGLYYGDKEKASTVVIEDQGNLGSLLAGEEIFYTTGSRLNG 333

Q2LAA4
(SEQ ID NO: 33 cont'd)
GNLFALRGSVELNGWDASLGGLYYGDKEKASTVVIEDQGNIGSLLAGEEIFYTTGSRLNG 331

Q2LA89
(SEQ ID NO: 34 cont'd)
GNLFALRGSVELNGWDASLGGLYYGDKEKASTVVIEDQGNIGSLLAGEEIFYTTGSRLNG 332

NB3
(SEQ ID NO: 35 cont'd)
GNFFALRGTVEVNGWDASLGGLYYGKKDKATVTTIEDQGNIGSLLAGEEIFYTRGSNLNG 332

Q2LAA9
(SEQ ID NO: 36 cont'd)
GNFFALRGTVEVNGWDASLGGLYYGKKDKATVTTIEDQGNIGSLLAGEEIFYTRGSNLNG 333

B5QHE5
(SEQ ID NO: 37 cont'd)
GNFFALRGTVEVNGWDASLGGLYYGKKDKITVTTIEDQGNLGSLLAGEEIFYTRGSNLNG 343

Q2LA96
(SEQ ID NO: 38 cont'd)
GNFFALRGTVEVNGWDASLGGLYYGKKDKITVTTIEDQGNLGSLLAGEEIFYTRGSNLNG 343

Q2LAB4
(SEQ ID NO: 39 cont'd)
GNFFALRGTVEVNGWDASLGGLYYGKKDKITVTTIEDQGNLGSLLAGEEIFYTRGSNLNG 343

Q2LA97
(SEQ ID NO: 40 cont'd)
GNFFALRGTVEVNGWDASLGGLYYGKKDKVTVTTIEDQGNLGSLLAGEEIFYTRGSNLNG 343

Q2LAA7
(SEQ ID NO: 41 cont'd)
GNFFALRGTVEVNGWDASLGGLYYGKKDKVTLTTIEDQGNLGSLLAGEEIFYTNGSNLNG 343

```
Q9F788
                                                        (SEQ ID NO: 42 cont'd)
GNFFALRGTVEVNGWDASLGGLYYGKKDKVTLTTIEDQGNLGSLLAGEEIFYTNGSNLNG  343

Q2LA87
                                                        (SEQ ID NO: 43 cont'd)
GNFFALRGTVEVNGWDASLGGLYYGKKDKVTLTTIEDQGNLGSLLAGEEIFYTNGSNLNG  343

Q2LA90
                                                        (SEQ ID NO: 44 cont'd)
GNFFALRGTVEVNGWDATLGGLYYGDKDNLTVTTIEDQGNLGSLLAGEEIFYTRGSNLNG  343

Q2LAA3
                                                        (SEQ ID NO: 45 cont'd)
GNFFALRGTVEVNGWDASLGGLYYGKKDKATVTTIEDQGNLGSLLAGQEIFYTRGSNLNG  344

Q0GF62
                                                        (SEQ ID NO: 46 cont'd)
GNFFALRGTVEVNGWDASLGGLYYGKKDKFTVTTIEDQGNLGSLLAGEEIFYTHGSRLNG  342

**:***:*  :*:*****:*******.*::  :  .  *:****:.*****:***** **.***
              (Arg 352)                      (Arg 381)

Hb1
                                                        (SEQ ID NO: 2 cont'd)
DTGRNIFGYVTGGYTFNETVPVGADFVYGGTKTEAAN-HLGGGKKLEAVARVDYKYSPKL  390

Q2LAB2
                                                        (SEQ ID NO: 3 cont'd)
DTGRNIFGYVTGGYTFNETVRVGADFVYGGTKTEAAN-HLGGGKKLEAVARVDYKYSPKL  393

Q2LAB0
                                                        (SEQ ID NO: 4 cont'd)
DTGRNIFGYVTGGYTFNETVRVGADFVYGGTKTEAAN-HLGGGKKLEAVARVDYKYSPKL  390

Hb2
                                                        (SEQ ID NO: 5 cont'd)
DTGRNIFGYVTGGYTFNETVRVGADFVYGGTKTEAAN-HLGGGKKLEAVARVDYKYSPKL  390

NB1
                                                        (SEQ ID NO: 6 cont'd)
DTGRNIFGYVTGGYTFNETVRVGADFVYGGTKTEAAN-HLGGGKKLEAVARVDYKYSPKL  390

Q9F791
                                                        (SEQ ID NO: 7 cont'd)
DTGRNIFGYVTGGYTFNETVRVGADFVYGGTKTEAAN-HLGGGKKLEAVARVDYKYSPKL  390

Hb3
                                                        (SEQ ID NO: 8 cont'd)
DTGRNIFGYVTGGYTFNEIVRVGADFVYGGTKTEAAN-HLGGGKKLEAVARVDYKYSPKL  390

D3FNB0
                                                        (SEQ ID NO: 9 cont'd)
DTGRNIFGYVTGGYTFNETVRVGADFVYGGTKTEATN-HLGGGKKLEAVARVDYKYSPKL  390

Q2LAB1
                                                        (SEQ ID NO: 10 cont'd)
DTGRNIFGYVTGGYTFNETVRVGADFVYGGTKTEATN-HLGGGKKLEAVARVDYKYSPKL  390

Q2LAB8
                                                        (SEQ ID NO: 11 cont'd)
DTGRNIFGYVTGGYTFNETVRVGADFVYGGTKTEATN-HLGGGKKLEAVARVDYKYSPKL  390

Q2LAA5
                                                        (SEQ ID NO: 12 cont'd)
DTGRNIFGYVTGGYTFNETVRVGADFVYGGTKTEATN-HLGGGKKLEAVARVDYKYSPKL  390

Q2LAB6
                                                        (SEQ ID NO: 13 cont'd)
DTGRNIFGYVTGGYTFNETVRVGADFVYGGTKTEATN-HLGGGKKLEAVARVDYKYSPKL  390

Q2LA95
                                                        (SEQ ID NO: 14 cont'd)
DTGRNIFGYVTGGYTFNETVRVGADFVYGGTKTEAAN-HLGGGKKLEAVARVDYKYSPKL  391

P80672
                                                        (SEQ ID NO: 1 cont'd)
DTGRNIFGYVTGGYTFNETVRVGADFVYGGTKTEAAN-HLGGGKKLEAVARVDYKYSPKL  390
```

```
Q2LAC5
                                                    (SEQ ID NO: 15 cont'd)
DTGRNIFGYVTGGYTFNETVRVGADFVYGGTKTEAAANHLGGGKKLEAVARVDYKYSPKL 391

Q2LAA2
                                                    (SEQ ID NO: 16 cont'd)
DTGRNIFGYVTGGYTFNETVRVGADFVYGGTKTEAAN-HLGGGKKLEAVARVDYKYSPKL 390

Q2LAB7
                                                    (SEQ ID NO: 17 cont'd)
DTGRNIFGYVTGGYTFNETVRVGADFVYGGTKTEAAN-HLGGGKKLEAVARVDYKYSPKL 390

Q2LAB9
                                                    (SEQ ID NO: 18 cont'd)
DTGRNIFGYVTGGYTFNETVRVGADFVYGGTKTEAAN-HLGGGKKLEAVARVDYKYSPKL 390

Q2LA91
                                                    (SEQ ID NO: 19 cont'd)
DTGRNIFGYVTGGYTFNETVRVGADFVYGGTKTEAAN-HLGGGKKLEAVARVDYKYSPKL 391

NB2
                                                    (SEQ ID NO: 20 cont'd)
DTGRNIFGYVTGGYTFNETVRVGADFVYGGTKTEDTA-HVGGGKKLEAVARVNYKYSPKL 390

Q2LA98
                                                    (SEQ ID NO: 21 cont'd)
DTGRNIFGYVTGGYTFNETVRVGADFVYGGTKTEDTA-HVGGGKKLEAVARVDYKYSPKL 391

A3ZHA2
                                                    (SEQ ID NO: 22 cont'd)
DTGRNIFGYVTGGYTFNETVRVGADFVYGGTKTEAAN-HLGGGKKLEAVARVDYKYSPKL 390

Q9F792
                                                    (SEQ ID NO: 23 cont'd)
DTGRNIFGYVTGGYTFNETVRVGADFVYGGTKTEAAN-HLGGGKKLEAVARVDYKYSPKL 390

Q2LAC0
                                                    (SEQ ID NO: 24 cont'd)
DTGRNIFGYVTGGYTFNETVRVGADFVYGGTKTEAAS-HLGGGKKLEAVARVDYKYSPKL 391

Q0GF63
                                                    (SEQ ID NO: 25 cont'd)
DTGRNIFGYVTGGYTFNETVRVGADFVYGGTKTEAAS-HLGGGKKLEAVARVDYKYSPKL 390

Q2LAB3
                                                    (SEQ ID NO: 26 cont'd)
DTGRNIFGYVTGGYTFNETVRVGADFVYGGTKTEAAN-HLGGGKKLEAVARVDYKYSPKL 383

Q2LA93
                                                    (SEQ ID NO: 27 cont'd)
DTGRNIFGYVTGGYTFNETVRVGADFVYGGTKTEAAS-HLGGGKKLEAVARVDYKYSPKL 383

Q2LAA0
                                                    (SEQ ID NO: 28 cont'd)
DTGRNIFGYVTGGYTFNETVRVGADFVYGGTKTEAAG-HLGGGKKLEAVARVDYKYSPKL 384

Q2LAC1
                                                    (SEQ ID NO: 29 cont'd)
DTGRNIFGYVTGGYTFNETVRVGADFVYGGTKTEAAN-HLGGGKKLEAVARVDYKYSPKL 384

Q2LAC4
                                                    (SEQ ID NO: 30 cont'd)
DTGRNIFGYVTGGYTFNETVRVGADFVYGGTKTEAAN-HLGGGKKLEAVARVDYKYSPKL 384

Q2LA94
                                                    (SEQ ID NO: 31 cont'd)
DTGRNIFGYVTGGYTFNETVRVGADFVYGGTKTEATT-HLGGGKKLEAVARVDYKYSPKL 384

Q2LA92
                                                    (SEQ ID NO: 32 cont'd)
DTGRNIFGYVTGGYTFNETVRVGADFVYGGTKTEAVG-HLGGGKKLEAVARVDYKYSPKL 392

Q2LAA4
                                                    (SEQ ID NO: 33 cont'd)
DTGRNIFGYVTGGYTFNETVRVGADFVYGGTKTETAG-HLGGGKKLEAVARVDYKYSPKL 390

Q2LA89
                                                    (SEQ ID NO: 34 cont'd)
DTGRNIFGYVTGGYTFNETVRVGADFVYGGTKTEAAN-HLGGGKKLEAVARVDYKYSPKL 391
```

-continued

```
NB3                                              (SEQ ID NO: 35 cont'd)
DIGRNIFGYVTGGYTFNETVRVGADFVYGGTKTNIIG---GGGKKLEAVARVDYKYSPKL 389

Q2LAA9                                           (SEQ ID NO: 36 cont'd)
DIGRNIFGYVTGGYTFNETVRVGADFVYGGTKTNIIG---QGGKKLEAVARVDYKYSPKL 390

B5QHE5                                           (SEQ ID NO: 37 cont'd)
DLGRNIFGYVTGGYTFNEAVRVGADFVYGGTKTNIIG---QGGKKLEAVARVDYKYSPKL 400

Q2LA96                                           (SEQ ID NO: 38 cont'd)
DLGRNIFGYVTGGYTFNEAVRVGADFVYGGTKTNIIG---QGGKKLEAVARVDYKYSPKL 400

Q2LAB4                                           (SEQ ID NO: 39 cont'd)
DLGRNIFGYVTGGYTFNEAVRVGADFVYGGTKTNIIG---QGGKKLEAVARVDYKYSPKL 400

Q2LA97                                           (SEQ ID NO: 40 cont'd)
DLGRNIFGYVTGGYTFNEAVRVGADFVYGGTKTNIIG---QGGKKLEAVARVDYKYSPKL 400

Q2LAA7                                           (SEQ ID NO: 41 cont'd)
DIGRNIFGYVTAGYTFNETVRVGADFVYGGTKTNIIG---QGGKKLEAVARVDYKYSPKL 400

Q9F788                                           (SEQ ID NO: 42 cont'd)
DIGRNIFGYVTAGYTFNETVRVGADFVYGGTKTNIIG---QGGKKLEAVARVDYKYSPKL 400

Q2LA87                                           (SEQ ID NO: 43 cont'd)
DIGRNIFGYVTAGYTFNETVRVGADFVYGGTKTNIIG---QGGKKLEAVARVDYKYSPKL 400

Q2LA90                                           (SEQ ID NO: 44 cont'd)
DLGRNIFGYVTGGYTFNEAVRVGADFVYGGTKTNIIG---QGGKKLEAVARVDYKYSPKL 400

Q2LAA3                                           (SEQ ID NO: 45 cont'd)
DLGRNIFGYVTAGYTFNEAVRVGADFVYGGTKTGEIG---NGGKKLEAVARVDYKYSPKL 401

Q0GF62                                           (SEQ ID NO: 46 cont'd)
DAGRNIFGYVTGGYTFNETVRVGADFVYGGTKTENVG---EGGKKLEAVARVDYKYSPKL 399

* *********.****** **************       ***********:*******
          (Ser 397)

(SEQ ID NO: 2 cont'd)
Hb1             NFSAFYSYVNLDQGVNTNESADHSTVRLQALYKF           424

(SEQ ID NO: 3 cont'd)
Q2LAB2          NFSAFYSYVNLDQGVNTNESADHSTVRLQALYKF           427

(SEQ ID NO: 4 cont'd)
Q2LAB0          NFSAFYSYVNLDQGVNTNESADHSTVRLQALYKF           424

(SEQ ID NO: 5 cont'd)
Hb2             NFSAFYSYVNLDQGVNTNESADHSTVRLQALYKF           424

(SEQ ID NO: 6 cont'd)
NB1             NFSAFYSYVNLDQGVNTNESADHSTVRLQALYKF           424

(SEQ ID NO: 7 cont'd)
Q9F791          NFSAFYSYVNLDQGVNTNESADHSTVRLQALYKF           424

(SEQ ID NO: 8 cont'd)
Hb3             NFSAFYSYVNLDQGVNTNESADHXTVRLQALYKF           424

(SEQ ID NO: 9 cont'd)
D3FNB0          NFSAFYSYVNLDQGVNTNESADHSTVRLQALYKF           424

(SEQ ID NO: 10 cont'd)
Q2LAB1          NFSAFYSYVNLDQGVNTNESADHSTVRLQALYKF           424

(SEQ ID NO: 11 cont'd)
Q2LAB8          NFSAFYSYVNLDQGVNTNESADHSTVRLQALYKF           424
```

-continued

```
                                          (SEQ ID NO: 12 cont'd)
Q2LAA5         NFSAFYSYVNLDQGVNTNESADHSTVRLQALYKF          424

(SEQ ID NO: 13 cont'd)
Q2LAB6         NFSAFYSYVNLDQGVNTNESADHSTVRLQALYKF          424

(SEQ ID NO: 14 cont'd)
Q2LA95         NFSAFYSYVNLDQGVNTNESADHSTVRLQALYKF          425

P80672
                                           (SEQ ID NO: 1 cont'd)
               NFSAFYSYVNLDQGVNTNESADHSTVRLQALYKF          424

(SEQ ID NO: 15 cont'd)
Q2LAC5         NFSAFYSYVNLDQGVNTNESADHSTVRLQALYKF          425

(SEQ ID NO: 16 cont'd)
Q2LAA2         NFSAFYSYVNLDQGVNTNESADHSTVRLQALYKF          424

(SEQ ID NO: 17 cont'd)
Q2LAB7         NFSAFYSYVNLDQGVNTNESADHSTVRLQALYKF          424

(SEQ ID NO: 18 cont'd)
Q2LAB9         NFSAFYSYVNLDQGVNTNESADHSTVRLQALYKF          424

(SEQ ID NO: 19 cont'd)
Q2LA91         NFSAFYSYVNLDQGANTNESADHSTVRLQALYKF          425

(SEQ ID NO: 20 cont'd)
NB2            NFSAFYSYVNLDQGVNTNESADHSTVRLQALYKF          424

(SEQ ID NO: 21 cont'd)
Q2LA98         NFSAFYSYVNLDQGVNTNESADHSTVKLQALYKF          425

(SEQ ID NO: 22 cont'd)
A3ZHA2         NFSAFYSYVNLDQGVNTNESADHSTVRLQALYKF          424

(SEQ ID NO: 23 cont'd)
Q9F792         NFSAFYSYVNLDQGVNTNESADHSTVRLQALYKF          424

(SEQ ID NO: 24 cont'd)
Q2LAC0         NFSAFYSYVNLDQGVNTNESADHSTVRLQALYKF          425

(SEQ ID NO: 25 cont'd)
Q0GF63         NFSAFYSYVNLDQGVNTNESADHSTVRLQALYKF          424

(SEQ ID NO: 26 cont'd)
Q2LAB3         NFSAFYSYVNLDQGVNTNESADHSTVRLQALYKF          417

(SEQ ID NO: 27 cont'd)
Q2LA93         NFSAFYSYVNLDQGVNTNESADHSTVRLQALYKF          417

(SEQ ID NO: 28 cont'd)
Q2LAA0         NFSAFYSYVNLDQGVNTNESADHSTVRLQALYKF          418

(SEQ ID NO: 29 cont'd)
Q2LAC1         NFSAFYSYVNLDQGVNTNESADHSTVRLQALYKF          418

(SEQ ID NO: 30 cont'd)
Q2LAC4         NFSAFYSYVNLDQGVNTNESADHSTVRLQALYKF          418

(SEQ ID NO: 31 cont'd)
Q2LA94         NFSAFYSYVNLDQGVNTNESADHSTVRLQALYKF          418

(SEQ ID NO: 32 cont'd)
Q2LA92         NFSAFYSYVNLDQGVNTNESADHSTVRLQALYKF          426

(SEQ ID NO: 33 cont'd)
Q2LAA4         NFSAFYSYVNLDEGVNTKESADHSTVRLQALYKF          424

(SEQ ID NO: 34 cont'd)
Q2LA89         NFSAFYSYVNLDEGVNTKESADHSTVRLQALYKF          425

(SEQ ID NO: 35 cont'd)
NB3            NFSAFYSYVNVDT---DPESTHHDAVRLQALYKF          420

(SEQ ID NO: 36 cont'd)
Q2LAA9         NFSAFYSYVNVDT---DPESTHHDAVRLQALYKF          421

(SEQ ID NO: 37 cont'd)
B5QHE5         NFSAFYSYVNVDT---DPESTHHDAVRLQALYKF          431
```

```
                                                     (SEQ ID NO: 38 cont'd)
Q2LA96          NFSAFYSYVNVDT---DPESTHHDAVKLQALYKF              431

(SEQ ID NO: 39 cont'd)
Q2LAB4          NFSAFYSYVNVDT---DPESTHHDAVRLQALYKF              431

(SEQ ID NO: 40 cont'd)
Q2LA97          NFSAFYSYVNVDT---DPESTHHDAVRLQALYKF              431

(SEQ ID NO: 41 cont'd)
Q2LAA7          NFSAFYSYVNVDT---DPESTHHDAVRLQALYKF              431

(SEQ ID NO: 42 cont'd)
Q9F788          NFSAFYSYVNVDT---DPESTHHDAVRLQALYKF              431

(SEQ ID NO: 43 cont'd)
Q2LA87          NFSAFYSYVNVDT---DPESTHHDAVRLQALYKF              431

(SEQ ID NO: 44 cont'd)
Q2LA90          NFSAFYSYVNVDT---DPESTHHDAVRLQALYKF              431

(SEQ ID NO: 45 cont'd)
Q2LAA3          NFSAFYSYVNVDT---DPESTHHDAVRLQALYKF              432

(SEQ ID NO: 46 cont'd)
Q0GF62          NFSAFYSYVNVDR---DPESTHHDAVRLQALYKF              430

**********:*      **:.*  :*:*******
```

Figure 5:
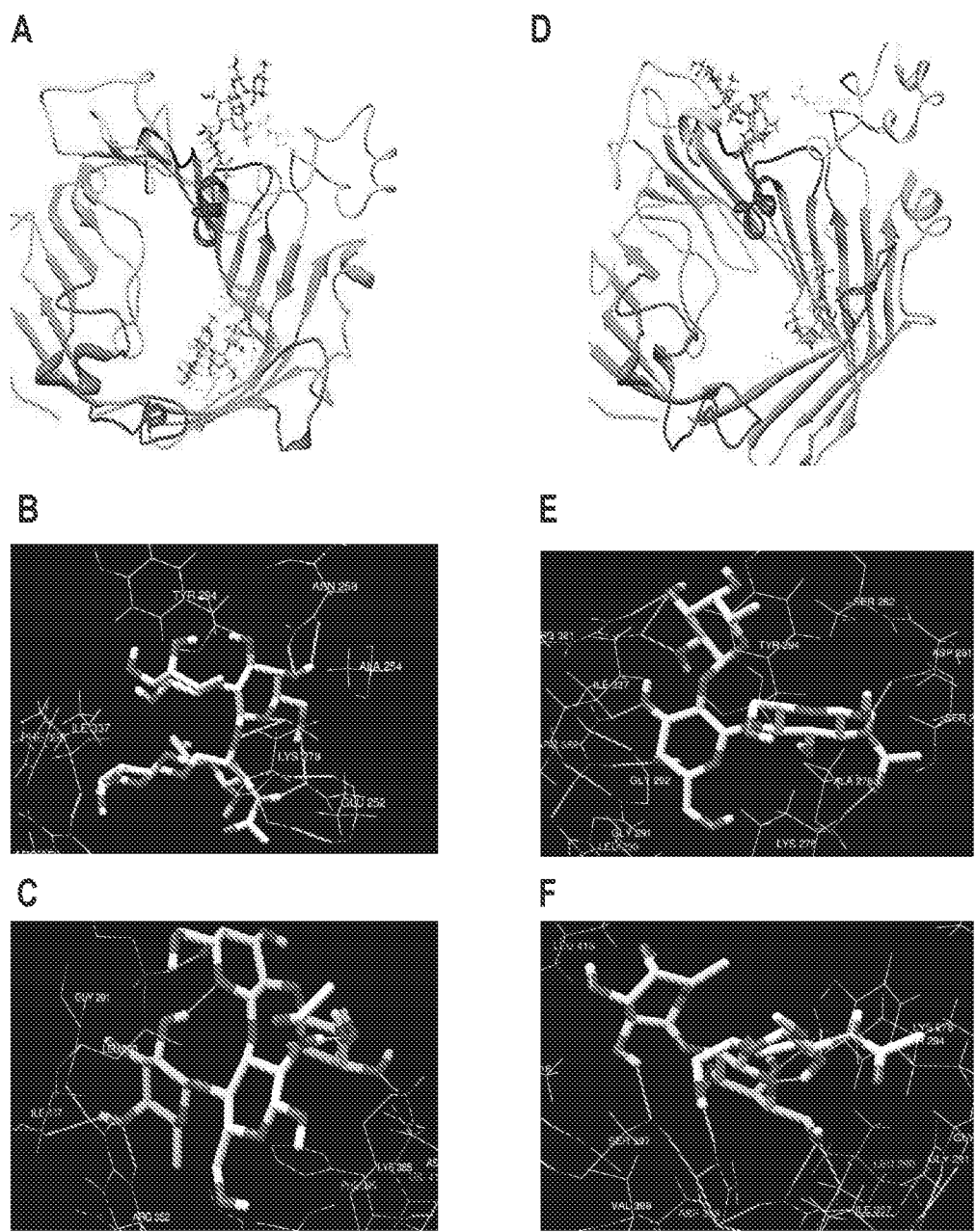

The major contributors in the interaction of glycosylated MOMP with Le$^b$ are residues Arg$^{352,381}$ and Lys$^{278}$, whereas only residues 352 and 278 are involved in the interaction of non-glycosylated MOMP with Le$^b$; FIG. 5 (paper). Residues Arg$^{352,381}$ are conserved in all sequences examined, whilst residue Lys$^{278}$ is semi-conserved and is replaced by Arg in some strains. The molecular properties of this amino acid suggests it would be able to mediate BgAg binding through hydrogen bond formation in a similar fashion to residues Arg$^{352,381}$.

---

The invention claimed is:

1. A method for treating or reducing *Campylobacter* colonization in an animal or meat product comprising administering to the animal or the meat product at least one compound in an effective amount to reduce the number of *Campylobacter* present in the gastrointestinal tract of the animal or in the meat product, wherein the compound is selected from the group consisting of:

a)
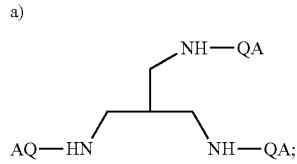

b)
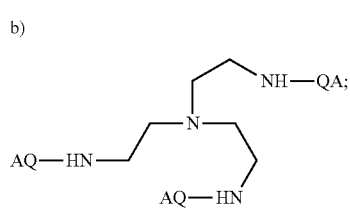

c)
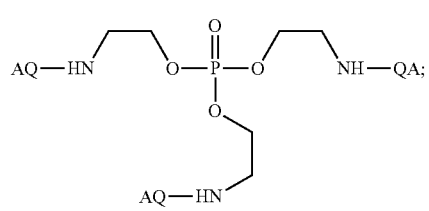

d)
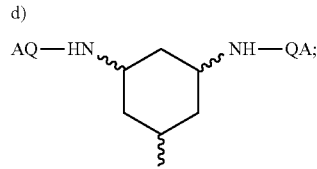

e)
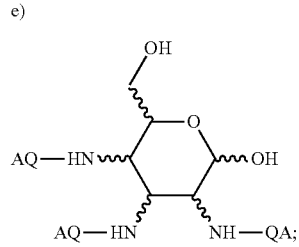

-continued f)
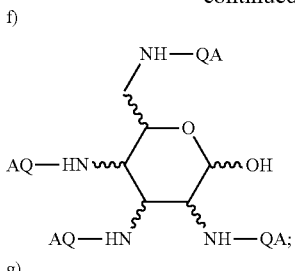

g)
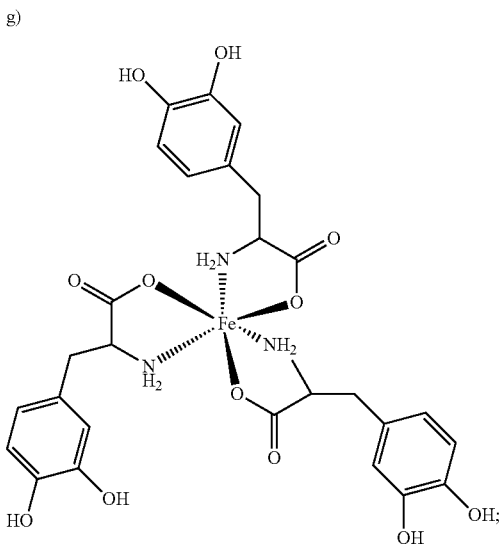

complex of DOPA with Fe III (3,4 dihydroxyphenylalanine)

and h)
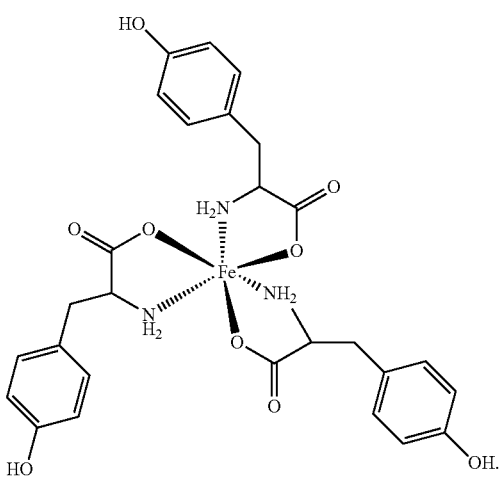

complex of tyrosine with Fe III

2. The method of claim 1, wherein the *Campylobacter* is *Campylobacter jejuni* or *Campylobacter Coli*.

3. The method of claim 1, wherein the compound is administered orally.

4. The method of claim 1, wherein the compound specifically binds to at least one of amino acid residue selected from the group consisting of $Arg^{352}$, $Thr^{268}$, $Lys^{278}$, $Lys^{385}$, $Asn^{258}$, $Leu^{290}$, $Tyr^{294}$, $Phe^{395}$, $Ile^{337}$, $Arg^{381}$, $Asp^{261}$, and $Ser^{397}$ of MOMP (SEQ ID NO:1).

5. The method of claim 1, wherein the compound specifically binds to at least amino acid residue $Thr^{268}$ of MOMP (SEQ ID NO. 1).

6. The method of claim 1, wherein the compound is in the form of an animal feed, animal drinking water, feed ingredient or feed supplement comprising the compound.

7. The method of claim 1, wherein the compound is administered in an animal's feed or drinking water.

8. The method of claim 1, wherein the compound is administered daily between 3 and 5 days before slaughter of a non-human animal.

9. The method of claim 1, wherein the compound is administered in an amount of between 0.3 and 32 mg/day/kilogram body weight of the animal.

10. The method of claim of claim 1 further comprising the steps of preparing a meat product from a non-human animal.

11. The method of claim 10, wherein the animal is poultry.

12. The method of claim 1 comprising administering the compound to a human.

13. The method of claim 1, wherein the compound reduces colonisation of the gastrointestinal tract of the animal with *Campylobacter*.

14. The method of claim 13, wherein the animal is poultry for human consumption.

15. The method of claim 1, wherein the animal is selected from the group consisting of cattle, sheep, pigs, goats and deer.

16. The method of claim 11, wherein the poultry is selected from the group consisting of chickens, geese, turkeys and ducks.

17. A method for treating or reducing *Campylobacter* colonization in an animal or meat product comprising administering to a non-human animal or a non-human meat product ferric quinate in an effective amount to reduce the number of *Campylobacter* present in the gastrointestinal tract of the animal or in the meat product.

18. The method of claim 17, wherein the *Campylobacter* is *Campylobacter jejuni* or *Campylobacter Coli*.

19. The method of claim 17, wherein the compound is administered orally.

20. The method of claim 19, wherein the compound is in the form of an animal feed, animal drinking water, feed ingredient or feed supplement comprising the compound.

21. The method of claim 17, wherein the compound is administered in the animal's feed or drinking water.

22. The method of claim 17, wherein the compound is administered daily between 3 and 5 days before slaughter of the animal.

23. The method of claim 17, wherein the compound is administered in an amount of between 0.3 and 32 mg/day/kilogram body weight of the animal.

24. The method of claim of claim 17 further comprising the step of preparing a meat product from the animal.

25. The method of claim 17, wherein the animal is selected from the group consisting of cattle, sheep, pigs, goats and deer.

26. The method of claim 17, wherein the animal is poultry selected from the group consisting of chickens, geese, turkeys and ducks.

* * * * *

UNITED STATES PATENT AND TRADEMARK OFFICE
CERTIFICATE OF CORRECTION

PATENT NO. : 9,655,912 B2
APPLICATION NO. : 14/379473
DATED : May 23, 2017
INVENTOR(S) : Jafar Mahdavi and Dlawer Ala'Aldeen It is certified that error appears in the above-identified patent and that said Letters Patent is hereby corrected as shown below:

In the Claims

Claim 1, Column 167, Line 11; replace "g)" with --g) complex of 3, 4 dihydroxyphenylalanine with Fe III--.
Claim 1, Column 167, Lines 33-34; delete "complex of DOPA with Fe III (3,4 dihydroxyphenylalanine)".
Claim 1, Column 167, Line 35; replace "h)" with --h) complex of tyrosine with Fe III--.
Claim 1, Column 167, Line 55; delete "complex of tyrosine with Fe III".
Claim 2, Column 167, Line 59; replace "Campylobacter Coli" with --Campylobacter coli--.
Claim 4, Column 167, Line 63; replace "at least one of amino acid residue" with --at least one amino acid residue--.
Claim 10, Column 168, Line 17; replace "of claim of claim" with --of claim--.
Claim 10, Column 168, Line 18; replace "steps" with --step--.
Claim 18, Column 168, Line 41; replace "Campylobacter Coli" with --Campylobacter coli--.
Claim 24, Column 168, Line 55; replace "of claim of claim" with --of claim--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ IDS: 46

<210> SEQ ID NO 1
<211> LENGTH: 424
<212> TYPE: PRT
<213> ORGANISM: Campylobacter jejuni

<400> SEQUENCE: 1

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Val Lys Val Val Asn Asn Ser Ile Asp Gly Leu Thr
145                 150                 155                 160
```

```
Leu Ala Ala Phe Ala Val Asp Ser Phe Met Ala Ala Glu Gln Gly Ala
            165                 170                 175

Asp Leu Leu Glu His Ser Asn Ile Ser Thr Thr Ser Asn Gln Ala Pro
        180                 185                 190

Phe Lys Val Asp Ser Val Gly Asn Leu Tyr Gly Ala Ala Val Gly
    195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 2
<211> LENGTH: 424
<212> TYPE: PRT
<213> ORGANISM: Campylobacter jejuni

<400> SEQUENCE: 2

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110
```

Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
130                 135                 140

Val Gly Thr Gly Val Lys Val Val Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Asp Leu Leu Gly His Ser Thr Thr Ser Thr Thr Gln Lys Ala Ala Pro
            180                 185                 190

Phe Lys Val Asp Ser Val Gly Asn Leu Tyr Gly Ala Ala Val Gly
            195                 200                 205

Ser Tyr Asp Leu Ala Gly Gly Gln Phe Asn Pro Gln Leu Trp Leu Ala
        210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 3
<211> LENGTH: 486
<212> TYPE: PRT
<213> ORGANISM: Campylobacter jejuni

<400> SEQUENCE: 3

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Met Lys Leu Val Lys

```
                50                  55                  60
Leu Ser Leu Val Ala Ala Leu Ala Ala Gly Ala Phe Ser Ala Ala Asn
 65                  70                  75                  80

Ala Thr Pro Leu Glu Glu Ala Ile Lys Asp Val Asp Val Ser Gly Val
                 85                  90                  95

Leu Arg Tyr Arg Tyr Asp Thr Gly Asn Phe Asp Lys Asn Phe Val Asn
                100                 105                 110

Asn Ser Asn Leu Asn Asn Ser Lys Gln Asp His Lys Tyr Arg Ala Gln
                115                 120                 125

Val Asn Phe Ser Ala Ala Ile Ala Asp Asn Phe Lys Ala Phe Val Gln
130                 135                 140

Phe Asp Tyr Asn Ala Ala Asp Gly Gly Tyr Gly Ala Asn Gly Ile Lys
145                 150                 155                 160

Asn Asp Gln Lys Gly Leu Phe Val Arg Gln Leu Tyr Leu Thr Tyr Thr
                165                 170                 175

Asn Glu Asp Val Ala Thr Ser Val Ile Ala Gly Lys Gln Gln Leu Asn
                180                 185                 190

Leu Ile Trp Thr Asp Asn Ala Ile Asp Gly Leu Val Gly Thr Gly Val
                195                 200                 205

Lys Val Val Asn Asn Ser Ile Asp Gly Leu Thr Leu Ala Ala Phe Ala
210                 215                 220

Val Asp Ser Phe Met Ala Ala Glu Gln Gly Ala Asp Leu Leu Gly His
225                 230                 235                 240

Ser Thr Thr Ser Thr Thr His Thr Thr Gln Lys Ala Ala Pro Phe Lys
                245                 250                 255

Val Asp Ser Val Gly Asn Leu Tyr Gly Ala Ala Ala Val Gly Ser Tyr
                260                 265                 270

Asp Leu Ala Gly Gly Gln Phe Asn Pro Gln Leu Trp Leu Ala Tyr Trp
                275                 280                 285

Asp Gln Val Ala Phe Phe Tyr Ala Val Asp Ala Ala Tyr Ser Thr Thr
                290                 295                 300

Ile Phe Asp Gly Ile Asn Trp Thr Leu Glu Gly Ala Tyr Leu Gly Asn
305                 310                 315                 320

Ser Leu Asp Ser Glu Leu Asp Asp Lys Thr His Ala Asn Gly Asn Leu
                325                 330                 335

Phe Ala Leu Lys Gly Ser Ile Glu Val Asn Gly Trp Asp Ala Ser Leu
                340                 345                 350

Gly Gly Leu Tyr Tyr Gly Asp Lys Glu Lys Ala Ser Thr Val Val Ile
                355                 360                 365

Glu Asp Gln Gly Asn Leu Gly Ser Leu Leu Ala Gly Glu Glu Ile Phe
370                 375                 380

Tyr Thr Thr Gly Ser Arg Leu Asn Gly Asp Thr Gly Arg Asn Ile Phe
385                 390                 395                 400

Gly Tyr Val Thr Gly Gly Tyr Thr Phe Asn Glu Thr Val Arg Val Gly
                405                 410                 415

Ala Asp Phe Val Tyr Gly Gly Thr Lys Thr Glu Ala Ala Asn His Leu
                420                 425                 430

Gly Gly Gly Lys Lys Leu Glu Ala Val Ala Arg Val Asp Tyr Lys Tyr
                435                 440                 445

Ser Pro Lys Leu Asn Phe Ser Ala Phe Tyr Ser Tyr Val Asn Leu Asp
                450                 455                 460

Gln Gly Val Asn Thr Asn Glu Ser Ala Asp His Ser Thr Val Arg Leu
465                 470                 475                 480
```

Gln Ala Leu Tyr Lys Phe
            485

<210> SEQ ID NO 4
<211> LENGTH: 424
<212> TYPE: PRT
<213> ORGANISM: Campylobacter jejuni

<400> SEQUENCE: 4

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Val Lys Val Val Asn Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Asp Leu Leu Gly His Ser Thr Thr Ser Thr Thr Gln Lys Ala Ala Pro
            180                 185                 190

Phe Lys Val Asp Ser Val Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Ala Ala Asn

-continued

```
            355                 360                 365
His Leu Gly Gly Gly Lys Lys Leu Glu Ala Val Ala Arg Val Asp Tyr
        370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 5
<211> LENGTH: 424
<212> TYPE: PRT
<213> ORGANISM: Campylobacter jejuni

<400> SEQUENCE: 5

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Val Asp Gly Leu
    130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Thr Gln Asn Ala Ala Pro
            180                 185                 190

Phe Lys Val Asp Ser Val Gly Asn Leu Tyr Gly Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
    290                 295                 300
```

```
Val Ile Glu Asp Gln Gly Asn Leu Gly Ser Leu Leu Ala Gly Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
                420
```

<210> SEQ ID NO 6
<211> LENGTH: 424
<212> TYPE: PRT
<213> ORGANISM: Campylobacter jejuni

<400> SEQUENCE: 6

```
Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Val Asp Gly Leu
    130                 135                 140

Val Gly Thr Gly Ile Lys Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Gln Asn Ala Ala Pro
            180                 185                 190

Phe Lys Val Asp Ser Val Gly Asn Leu Tyr Gly Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255
```

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Lys Ala Ser Thr Val
290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 7
<211> LENGTH: 424
<212> TYPE: PRT
<213> ORGANISM: Campylobacter jejuni

<400> SEQUENCE: 7

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Ser Lys Gln Asp His
50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
            85                  90                  95

Ala Asn Gly Ile Lys Asn Asp Gln Lys Gly Leu Phe Val Arg Gln Leu
        100                 105                 110

Tyr Leu Thr Tyr Thr Asn Glu Asp Val Ala Thr Ser Val Ile Ala Gly
    115                 120                 125

Lys Gln Gln Leu Asn Thr Ile Trp Thr Asp Asn Gly Val Asp Gly Leu
130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Gln Asn Ala Ala Pro
            180                 185                 190

Phe Lys Val Asp Ser Val Gly Asn Leu Tyr Gly Ala Ala Ala Val Gly

```
                195                 200                 205
Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 8
<211> LENGTH: 424
<212> TYPE: PRT
<213> ORGANISM: Campylobacter jejuni
<220> FEATURE:
<221> NAME/KEY: MISC_FEATURE
<222> LOCATION: (414)..(414)
<223> OTHER INFORMATION: Xaa = any amino acid

<400> SEQUENCE: 8

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125
```

-continued

```
Lys Gln Gln Leu Asn Thr Ile Trp Thr Asp Asn Gly Val Asp Gly Leu
            130                 135                 140

Val Gly Thr Gly Ile Lys Val Ala Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly Gln Ser Thr Ile Ser Thr Gln Asn Ala Ala Pro
            180                 185                 190

Phe Lys Val Asp Ser Val Gly Asn Leu Tyr Gly Ala Ala Val Gly
                195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
                275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Ile Val Arg
            340                 345                 350

Val Gly Ala Asp Phe Val Tyr Gly Gly Thr Lys Thr Glu Ala Ala Asn
            355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Xaa Thr Val
                405                 410                 415

Arg Leu Gln Ala Leu Tyr Lys Phe
            420

<210> SEQ ID NO 9
<211> LENGTH: 424
<212> TYPE: PRT
<213> ORGANISM: Campylobacter jejuni

<400> SEQUENCE: 9

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asn His
    50                  55                  60

Lys Tyr Arg Ala Gln Val Asn Phe Ser Ala Ala Ile Ala Asp Asn Phe
```

```
                65                  70                  75                  80
        Lys Ala Phe Ile Gln Phe Asp Tyr Asn Ala Ala Asp Gly Gly Tyr Gly
                        85                  90                  95

Ala Asn Gly Ile Lys Asn Asp Gln Lys Gly Leu Phe Val Arg Gln Leu
                    100                 105                 110

Tyr Leu Thr Tyr Thr Asn Glu Asp Val Ala Thr Ser Val Ile Ala Gly
                    115                 120                 125

Lys Gln Gln Leu Asn Thr Ile Trp Thr Asp Asn Gly Val Asp Gly Leu
                130                 135                 140

Val Gly Thr Gly Ile Lys Val Val Asn Asn Ser Ile Asp Gly Leu Thr
        145                 150                 155                 160

Leu Ala Ala Phe Ala Val Asp Ser Phe Met Ala Glu Glu Gln Gly Ala
                        165                 170                 175

Asp Leu Leu Gly Lys Ser Thr Ile Ser Thr Thr Gln Lys Ala Ala Pro
                    180                 185                 190

Phe Gln Ala Asp Ser Leu Gly Asn Leu Tyr Gly Ala Ala Val Gly
                    195                 200                 205

Ser Tyr Asp Leu Ala Gly Gly Gln Phe Asn Pro Gln Leu Trp Leu Ala
                210                 215                 220

Tyr Trp Asp Gln Val Ala Phe Phe Tyr Ala Val Asp Ala Ala Tyr Ser
        225                 230                 235                 240

Thr Thr Ile Phe Asp Gly Ile Asn Trp Thr Leu Glu Gly Ala Tyr Leu
                        245                 250                 255

Gly Asn Ser Leu Asp Ser Glu Leu Asn Asp Lys Arg His Ala Asn Gly
                    260                 265                 270

Asn Leu Phe Ala Leu Lys Gly Ser Ile Glu Val Asn Gly Trp Asp Ala
                    275                 280                 285

Ser Leu Gly Gly Leu Tyr Tyr Gly Asp Lys Glu Lys Ala Ser Thr Val
                290                 295                 300

Val Ile Glu Asp Gln Gly Asn Leu Gly Ser Leu Leu Ala Gly Glu Glu
        305                 310                 315                 320

Ile Phe Tyr Thr Thr Gly Ser Arg Leu Asn Gly Asp Thr Gly Arg Asn
                        325                 330                 335

Ile Phe Gly Tyr Val Thr Gly Tyr Thr Phe Asn Glu Thr Val Arg
                    340                 345                 350

Val Gly Ala Asp Phe Val Tyr Gly Gly Thr Lys Thr Glu Ala Thr Asn
                    355                 360                 365

His Leu Gly Gly Lys Lys Leu Glu Ala Val Ala Arg Val Asp Tyr
                370                 375                 380

Lys Tyr Ser Pro Lys Leu Asn Phe Ser Ala Phe Tyr Ser Tyr Val Asn
        385                 390                 395                 400

Leu Asp Gln Gly Val Asn Thr Asn Glu Ser Ala Asp His Ser Thr Val
                        405                 410                 415

Arg Leu Gln Ala Leu Tyr Lys Phe
                    420

<210> SEQ ID NO 10
<211> LENGTH: 424
<212> TYPE: PRT
<213> ORGANISM: Campylobacter jejuni

<400> SEQUENCE: 10

Met Lys Leu Val Lys Leu Ser Leu Val Ala Ala Leu Ala Ala Gly Ala
1               5                   10                  15
```

-continued

```
Phe Ser Ala Ala Asn Ala Thr Pro Leu Glu Glu Ala Ile Lys Asp Val
             20                  25                  30
Asp Val Ser Gly Val Leu Arg Tyr Arg Tyr Asp Thr Gly Asn Phe Asp
         35                  40                  45
Lys Asn Phe Val Asn Asn Ser Asn Leu Asn Asn Ser Lys Gln Asp His
 50                  55                  60
Lys Tyr Arg Ala Gln Val Asn Phe Ser Ala Ala Ile Ala Asp Asn Phe
 65                  70                  75                  80
Lys Ala Phe Val Gln Phe Asp Tyr Asn Ala Ala Asp Gly Gly Tyr Gly
                 85                  90                  95
Ala Asn Gly Ile Lys Asn Asp Gln Lys Gly Leu Phe Val Arg Gln Leu
            100                 105                 110
Tyr Leu Thr Tyr Thr Asn Glu Asp Val Ala Thr Ser Val Ile Ala Gly
            115                 120                 125
Lys Gln Gln Leu Asn Thr Ile Trp Thr Asp Asn Gly Val Asp Gly Leu
130                 135                 140
Val Gly Thr Gly Ile Lys Val Val Asn Asn Ser Ile Asp Gly Leu Thr
145                 150                 155                 160
Leu Ala Ala Phe Ala Val Asp Ser Phe Met Ala Glu Glu Gln Gly Ala
                165                 170                 175
Asp Leu Leu Gly Gln Ser Thr Ile Ser Thr Thr Gln Lys Ala Ala Pro
            180                 185                 190
Phe Gln Ala Asp Ser Leu Gly Asn Leu Tyr Gly Ala Ala Ala Val Gly
            195                 200                 205
Ser Tyr Asp Leu Ala Gly Gly Gln Phe Asn Pro Gln Leu Trp Leu Ala
210                 215                 220
Tyr Trp Asp Gln Val Ala Phe Phe Tyr Ala Val Asp Ala Ala Tyr Ser
225                 230                 235                 240
Thr Thr Ile Phe Asp Gly Ile Asn Trp Thr Leu Glu Gly Ala Tyr Leu
                245                 250                 255
Gly Asn Ser Leu Asp Ser Glu Leu Asp Asp Lys Arg His Ala Asn Gly
            260                 265                 270
Asn Leu Phe Ala Leu Lys Gly Ser Ile Glu Val Asn Gly Trp Asp Ala
            275                 280                 285
Ser Leu Gly Gly Leu Tyr Tyr Gly Asp Lys Glu Lys Ala Ser Thr Val
            290                 295                 300
Val Ile Glu Asp Gln Gly Asn Leu Gly Ser Leu Leu Ala Gly Glu Glu
305                 310                 315                 320
Ile Phe Tyr Thr Thr Gly Ser Arg Leu Asn Gly Asp Thr Gly Arg Asn
                325                 330                 335
Ile Phe Gly Tyr Val Thr Gly Tyr Thr Phe Asn Glu Thr Val Arg
            340                 345                 350
Val Gly Ala Asp Phe Val Tyr Gly Gly Thr Lys Thr Glu Ala Thr Asn
            355                 360                 365
His Leu Gly Gly Gly Lys Lys Leu Glu Ala Val Ala Arg Val Asp Tyr
            370                 375                 380
Lys Tyr Ser Pro Lys Leu Asn Phe Ser Ala Phe Tyr Ser Tyr Val Asn
385                 390                 395                 400
Leu Asp Gln Gly Val Asn Thr Asn Glu Ser Ala Asp His Ser Thr Val
                405                 410                 415
Arg Leu Gln Ala Leu Tyr Lys Phe
            420
```

<210> SEQ ID NO 11
<211> LENGTH: 423
<212> TYPE: PRT
<213> ORGANISM: Campylobacter jejuni

<400> SEQUENCE: 11

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Val Asp Gly Leu
130                 135                 140

Val Gly Thr Gly Ile Lys Trp Asn Asn Ser Ile Asp Gly Leu Thr Leu
145                 150                 155                 160

Ala Ala Phe Ala Val Asp Ser Phe Met Ala Glu Glu Gln Gly Ala Asp
                165                 170                 175

Leu Leu Gly Gln Ser Thr Ile Ser Thr Thr Gln Lys Ala Ala Pro Phe
            180                 185                 190

Gln Ala Asp Ser Leu Gly Asn Leu Tyr Gly Ala Ala Val Gly Ser
        195                 200                 205

Tyr Asp Leu Ala Gly Gly Gln Phe Asn Pro Gln Leu Trp Leu Ala Tyr
    210                 215                 220

Trp Asp Gln Val Ala Phe Phe Tyr Ala Val Asp Ala Ala Tyr Ser Thr
225                 230                 235                 240

Thr Ile Phe Asp Gly Ile Asn Trp Thr Leu Glu Gly Ala Tyr Leu Gly
                245                 250                 255

Asn Ser Leu Asp Ser Glu Leu Asp Asp Lys Thr His Ala Asn Gly Asn
            260                 265                 270

Leu Phe Ala Leu Lys Gly Thr Ile Glu Val Asn Gly Trp Asp Ala Ser
        275                 280                 285

Leu Gly Gly Leu Tyr Tyr Gly Asp Lys Glu Lys Ala Ser Thr Val Val
    290                 295                 300

Ile Glu Asp Gln Gly Asn Leu Gly Ser Leu Leu Ala Gly Glu Glu Ile
305                 310                 315                 320

Phe Tyr Thr Thr Gly Ser Arg Leu Asn Gly Asp Thr Gly Arg Asn Ile
                325                 330                 335

Phe Gly Tyr Val Thr Gly Gly Tyr Thr Phe Asn Glu Thr Val Arg Val
            340                 345                 350

Gly Ala Asp Phe Val Tyr Gly Gly Thr Lys Thr Glu Ala Thr Asn His
        355                 360                 365

Leu Gly Gly Gly Lys Lys Leu Glu Ala Val Ala Arg Val Asp Tyr Lys
    370                 375                 380

Tyr Ser Pro Lys Leu Asn Phe Ser Ala Phe Ser Tyr Val Asn Leu
385                 390                 395                 400

Asp Gln Gly Val Asn Thr Asn Glu Ser Ala Asp His Ser Thr Val Arg
            405                 410                 415

Leu Gln Ala Leu Tyr Lys Phe
            420

<210> SEQ ID NO 12
<211> LENGTH: 424
<212> TYPE: PRT
<213> ORGANISM: Campylobacter jejuni

<400> SEQUENCE: 12

Met Lys Leu Val Lys Leu Ser Leu Val Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Val Asp Gly Leu
130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Thr
                165                 170                 175

Asp Leu Leu Gly Gln Ser Thr Ile Ser Thr Thr Gln Asn Thr Ala Pro
            180                 185                 190

Phe Gln Ala Asp Ser Leu Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Arg His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Lys Ala Ser Thr Val
290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

```
Ile Phe Gly Tyr Val Thr Gly Tyr Thr Phe Asn Glu Thr Val Arg
                340             345                 350

Val Gly Ala Asp Phe Val Tyr Gly Gly Thr Lys Thr Glu Ala Thr Asn
            355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
                420

<210> SEQ ID NO 13
<211> LENGTH: 424
<212> TYPE: PRT
<213> ORGANISM: Campylobacter jejuni

<400> SEQUENCE: 13

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
50                  55                  60

Lys Tyr Arg Ala Gln Val Asn Phe Ser Ala Ile Ala Asp Asn Phe
65              70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Val Asp Gly Leu
130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Glu Glu Gln Gly Thr
                165                 170                 175

Asp Leu Leu Gly Gln Ser Thr Ile Ser Thr Gln Asn Thr Ala Leu
            180                 185                 190

Phe Gln Ala Asp Ser Leu Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Arg His Ala Asn Gly
            260                 265                 270

Asn Leu Phe Ala Leu Lys Gly Ser Ile Glu Val Asn Gly Trp Asp Ala
```

|   |   |   | 275 |   |   |   | 280 |   |   |   | 285 |   |   |
|---|---|---|---|---|---|---|---|---|---|---|---|---|---|

Ser Leu Gly Gly Leu Tyr Tyr Gly Asp Lys Glu Lys Ala Ser Thr Val
290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
                340                 345                 350

Val Gly Ala Asp Phe Val Tyr Gly Gly Thr Lys Thr Glu Ala Thr Asn
                355                 360                 365

His Leu Gly Gly Gly Lys Lys Leu Glu Ala Val Ala Arg Val Asp Tyr
370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
                420

<210> SEQ ID NO 14
<211> LENGTH: 425
<212> TYPE: PRT
<213> ORGANISM: Campylobacter jejuni

<400> SEQUENCE: 14

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
                100                 105                 110

Tyr Leu Thr Tyr Thr Asn Glu Asp Val Ala Thr Ser Val Ile Ala Gly
            115                 120                 125

Lys Gln Gln Leu Asn Thr Ile Trp Thr Asp Asn Gly Val Asp Gly Leu
    130                 135                 140

Val Gly Thr Gly Ile Lys Val Val Asn Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Asp Leu Leu Gly His Ser Asn Thr Ser Thr Ala Thr Pro Asn Gln Val
                180                 185                 190

Pro Phe Lys Val Asp Ser Val Gly Asn Leu Tyr Gly Ala Ala Ala Val
            195                 200                 205

Gly Ser Tyr Asp Leu Ala Gly Gly Gln Phe Asn Pro Gln Leu Trp Leu
    210                 215                 220

```
Ala Tyr Trp Asp Gln Val Ala Phe Phe Tyr Ala Val Asp Ala Ala Tyr
225                 230                 235                 240

Ser Thr Thr Ile Phe Asp Gly Ile Asn Trp Thr Leu Glu Gly Ala Tyr
            245                 250                 255

Leu Gly Asn Ser Leu Asp Ser Glu Leu Asp Asp Thr Thr His Ala Asn
        260                 265                 270

Gly Asn Leu Phe Ala Leu Lys Gly Ser Ile Glu Val Asn Gly Trp Asp
    275                 280                 285

Ala Ser Leu Gly Gly Leu Tyr Gly Asp Lys Glu Lys Ala Ser Thr
290                 295                 300

Val Val Ile Glu Asp Gln Gly Asn Leu Gly Ser Leu Ala Gly Glu
305                 310                 315                 320

Glu Ile Phe Tyr Thr Thr Gly Ser Arg Leu Asn Gly Asp Thr Gly Arg
                325                 330                 335

Asn Ile Phe Gly Tyr Val Thr Gly Gly Tyr Thr Phe Asn Glu Thr Val
            340                 345                 350

Arg Val Gly Ala Asp Phe Val Tyr Gly Gly Thr Lys Thr Glu Ala Ala
        355                 360                 365

Asn His Leu Gly Gly Lys Lys Leu Glu Ala Val Ala Arg Val Asp
370                 375                 380

Tyr Lys Tyr Ser Pro Lys Leu Asn Phe Ser Ala Phe Tyr Ser Tyr Val
385                 390                 395                 400

Asn Leu Asp Gln Gly Val Asn Thr Asn Glu Ser Ala Asp His Ser Thr
                405                 410                 415

Val Arg Leu Gln Ala Leu Tyr Lys Phe
                420                 425

<210> SEQ ID NO 15
<211> LENGTH: 425
<212> TYPE: PRT
<213> ORGANISM: Campylobacter

<400> SEQUENCE: 15

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Lys Gln Asp His
    50                  55                  60

Lys Tyr Arg Ala Gln Val Asn Phe Ser Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asn Asn Val Lys Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Val Lys Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175
```

```
Asp Leu Leu Gly His Ser Asn Ile Ser Thr Thr Ser Lys Gln Ala Pro
            180                 185                 190

Phe Lys Val Asp Ser Val Gly Asn Leu Tyr Gly Ala Ala Ala Val Gly
            195                 200                 205

Ser Tyr Asp Leu Ala Gly Gly Gln Phe Asn Pro Gln Leu Trp Leu Ala
210                 215                 220

Tyr Trp Asp Gln Val Thr Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Thr Ile Glu Val Asn Gly Trp Asp Ala
            275                 280                 285

Ser Leu Gly Gly Leu Tyr Tyr Gly Asp Lys Glu Lys Ala Ser Thr Val
290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Ala
            355                 360                 365

Asn His Leu Gly Gly Lys Lys Leu Glu Ala Val Ala Arg Val Asp
370                 375                 380

Tyr Lys Tyr Ser Pro Lys Leu Asn Phe Ser Ala Phe Tyr Ser Tyr Val
385                 390                 395                 400

Asn Leu Asp Gln Gly Val Asn Thr Asn Glu Ser Ala Asp His Ser Thr
                405                 410                 415

Val Arg Leu Gln Ala Leu Tyr Lys Phe
            420                 425

<210> SEQ ID NO 16
<211> LENGTH: 424
<212> TYPE: PRT
<213> ORGANISM: Campylobacter jejuni

<400> SEQUENCE: 16

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Lys Gln Asp His
    50                  55                  60

Lys Tyr Arg Ala Gln Val Asn Phe Ser Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
```

```
            115                 120                 125
Lys Gln Gln Leu Asn Leu Ile Trp Thr Asp Asn Ala Ile Asp Gly Leu
        130                 135                 140

Val Gly Thr Gly Val Lys Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Ser Thr Thr Ser Thr Thr Gln Ala Thr Ala Pro
                180                 185                 190

Phe Lys Val Asp Ser Val Gly Asn Leu Tyr Gly Ala Ala Val Gly
                195                 200                 205

Ser Tyr Asp Leu Ala Gly Gly Gln Phe Asn Pro Gln Leu Trp Leu Ala
        210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
        260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
        290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
                340                 345                 350

Val Gly Ala Asp Phe Val Tyr Gly Gly Thr Lys Thr Glu Ala Ala Asn
                355                 360                 365

His Leu Gly Gly Gly Lys Lys Leu Glu Ala Val Ala Arg Val Asp Tyr
        370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
                420

<210> SEQ ID NO 17
<211> LENGTH: 424
<212> TYPE: PRT
<213> ORGANISM: Campylobacter jejuni

<400> SEQUENCE: 17

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Asn Lys Gln Asp His
        50                  55                  60
```

```
Lys Tyr Arg Ala Gln Val Asn Phe Ser Ala Ala Ile Ala Asp Asp Phe
 65                  70                  75                  80

Lys Ala Phe Ile Gln Phe Asp Tyr Asn Ala Val Asp Gly Gly Thr Gly
                 85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Val Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Ser Thr Thr Ser Thr Thr Gln Ala Thr Ala Pro
            180                 185                 190

Phe Lys Val Asp Ser Val Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 18
<211> LENGTH: 424
<212> TYPE: PRT
<213> ORGANISM: Campylobacter jejuni

<400> SEQUENCE: 18

Met Lys Leu Val Lys Leu Ser Leu Val Ala Ala Leu Ala Ala Gly Ala
1               5                   10                  15
```

```
Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Ser Lys Gln Asp His
 50                  55                  60

Lys Tyr Arg Ala Gln Val Asn Phe Ser Ala Ala Ile Ala Asp Asn Phe
 65              70                  75                      80

Lys Ala Phe Ile Gln Phe Asp Tyr Asn Ala Val Asp Gly Gly Thr Gly
                85                  90                  95

Val Asp Asn Val Thr Asn Thr Glu Lys Gly Leu Phe Val Arg Gln Leu
            100                 105                 110

Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
130                 135                 140

Val Gly Thr Gly Val Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Glu His Ser Thr Ile Ser Thr Thr Gln Asn Ala Ala Pro
            180                 185                 190

Phe Lys Val Asp Ser Val Gly Asn Leu Tyr Gly Ala Ala Val Gly
            195                 200                 205

Ser Tyr Asp Leu Ala Gly Gly Gln Phe Asn Pro Gln Leu Trp Leu Ala
        210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
            275                 280                 285

Ser Leu Gly Gly Leu Tyr Tyr Gly Asp Lys Glu Lys Ala Ser Thr Val
        290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Thr Lys Thr Glu Ala Ala Asn
        355                 360                 365

His Leu Gly Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
                420
```

<210> SEQ ID NO 19
<211> LENGTH: 425
<212> TYPE: PRT
<213> ORGANISM: Campylobacter jejuni

<400> SEQUENCE: 19

```
Met Lys Leu Val Lys Leu Ser Leu Val Ala Leu Ala Ala Gly Ala
 1               5                  10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
                35                  40                  45

Lys Asn Phe Val Asn Asn Ser Asn Leu Asn Asn Asn Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                    85                  90                  95

Val Asp Asn Val Thr Asn Ala Glu Lys Gly Leu Phe Val Arg Gln Leu
                100                 105                 110

Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
        130                 135                 140

Val Gly Thr Gly Val Lys Val Val Asn Asn Ser Ile Asp Gly Leu Thr
145                 150                 155                 160

Leu Ala Ala Phe Ala Val Asp Ser Phe Met Ala Ala Glu Gln Gly Ala
                    165                 170                 175

Asp Leu Leu Gly His Ser Asn Ile Ser Thr Thr Asn Ala Asn Gln Ala
                180                 185                 190

Pro Phe Lys Val Asp Ser Val Gly Asn Leu Tyr Gly Ala Ala Ala Val
            195                 200                 205

Gly Ser Tyr Asp Leu Ala Gly Gly Gln Phe Asn Pro Gln Leu Trp Leu
        210                 215                 220

Ala Tyr Trp Asp Gln Val Ala Phe Phe Tyr Ala Val Asp Ala Ala Tyr
225                 230                 235                 240

Ser Thr Thr Ile Phe Asp Gly Ile Asn Trp Thr Leu Glu Gly Ala Tyr
                    245                 250                 255

Leu Gly Asn Ser Leu Asp Ser Glu Leu Asp Asp Lys Thr His Ala Asn
                260                 265                 270

Gly Asn Leu Phe Ala Leu Lys Gly Ser Ile Glu Val Asn Gly Trp Asp
            275                 280                 285

Ala Ser Leu Gly Gly Leu Tyr Tyr Gly Asp Lys Glu Lys Ala Ser Thr
        290                 295                 300

Val Val Ile Glu Asp Gln Gly Asn Leu Gly Ser Leu Leu Ala Gly Glu
305                 310                 315                 320

Glu Ile Phe Tyr Thr Thr Gly Ser Arg Leu Asn Gly Asp Thr Gly Arg
                    325                 330                 335

Asn Ile Phe Gly Tyr Val Thr Gly Gly Tyr Thr Phe Asn Glu Thr Val
                340                 345                 350

Arg Val Gly Ala Asp Phe Val Tyr Gly Thr Lys Thr Glu Ala Ala
            355                 360                 365

Asn His Leu Gly Gly Gly Lys Lys Leu Glu Ala Val Ala Arg Val Asp
        370                 375                 380
```

```
Tyr Lys Tyr Ser Pro Lys Leu Asn Phe Ser Ala Phe Ser Tyr Val
385                 390                 395                 400

Asn Leu Asp Gln Gly Ala Asn Thr Asn Glu Ser Ala Asp His Ser Thr
            405                 410                 415

Val Arg Leu Gln Ala Leu Tyr Lys Phe
            420                 425

<210> SEQ ID NO 20
<211> LENGTH: 424
<212> TYPE: PRT
<213> ORGANISM: Campylobacter jejuni

<400> SEQUENCE: 20

Met Lys Leu Val Lys Leu Ser Leu Val Ala Ala Leu Ala Ala Gly Ala
1               5                   10                  15

Phe Ser Ala Ala Asn Ala Thr Pro Leu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Lys Gln Asp His
50                  55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
130                 135                 140

Val Gly Thr Gly Ile Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Ser Asn Ile Ser Thr Thr Pro Asn Gln Ala Pro
            180                 185                 190

Phe Lys Val Asp Ser Val Gly Asn Leu Tyr Gly Ala Ala Val Gly
        195                 200                 205

Ser Tyr Asp Leu Ala Gly Gly Gln Phe Asn Pro Gln Leu Trp Leu Ala
210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285

Ser Leu Gly Gly Leu Tyr Tyr Gly Asp Lys Glu Lys Ala Ser Thr Val
            290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
```

```
            325                 330                 335
Ile Phe Gly Tyr Val Thr Gly Gly Tyr Thr Phe Asn Glu Thr Val Arg
                340                 345                 350

Val Gly Ala Asp Phe Val Tyr Gly Gly Thr Lys Thr Glu Asp Thr Ala
            355                 360                 365

His Val Gly Gly Gly Lys Lys Leu Glu Ala Val Ala Arg Val Asn Tyr
        370                 375                 380

Lys Tyr Ser Pro Lys Leu Asn Phe Ser Ala Phe Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 21
<211> LENGTH: 425
<212> TYPE: PRT
<213> ORGANISM: Campylobacter jejuni

<400> SEQUENCE: 21

Met Lys Leu Val Lys Leu Ile Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Lys Gln Asp His
50                  55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Ile Lys Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Arg Asn Ile Ser Thr Ile Thr Pro Asn Gln Ala
            180                 185                 190

Pro Phe Lys Val Asp Ser Val Gly Asn Leu Tyr Gly Ala Ala Val
        195                 200                 205

Gly Ser Tyr Asp Leu Ala Gly Gly Gln Phe Asn Pro Gln Leu Trp Leu
    210                 215                 220

Ala Tyr Trp Asp Gln Val Ala Phe Phe Tyr Ala Val Asp Ala Ala Tyr
225                 230                 235                 240

Ser Thr Thr Ile Phe Asp Gly Ile Asn Trp Thr Leu Glu Gly Ala Tyr
                245                 250                 255

Leu Gly Asn Ser Leu Asp Ser Glu Leu Asp Asp Lys Thr His Ala Asn
            260                 265                 270
```

```
Gly Asn Leu Phe Ala Leu Lys Gly Ser Ile Glu Val Asn Gly Trp Asp
            275                 280                 285

Ala Ser Leu Gly Gly Leu Tyr Tyr Gly Asp Lys Glu Lys Ala Ser Thr
290                 295                 300

Val Val Ile Glu Asp Gln Gly Asn Leu Gly Ser Leu Leu Ala Gly Glu
305                 310                 315                 320

Glu Ile Phe Tyr Thr Thr Gly Ser Arg Leu Asn Gly Asp Thr Gly Arg
                325                 330                 335

Asn Ile Phe Gly Tyr Val Thr Gly Gly Tyr Thr Phe Asn Glu Thr Val
                340                 345                 350

Arg Val Gly Ala Asp Phe Val Tyr Gly Gly Thr Lys Thr Glu Asp Thr
            355                 360                 365

Ala His Val Gly Gly Gly Lys Lys Leu Glu Ala Val Ala Arg Val Asp
            370                 375                 380

Tyr Lys Tyr Ser Pro Lys Leu Asn Phe Ser Ala Phe Ser Tyr Val
385                 390                 395                 400

Asn Leu Asp Gln Gly Val Asn Thr Asn Glu Ser Ala Asp His Ser Thr
                405                 410                 415

Val Lys Leu Gln Ala Leu Tyr Lys Phe
            420                 425

<210> SEQ ID NO 22
<211> LENGTH: 424
<212> TYPE: PRT
<213> ORGANISM: Campylobacter jejuni

<400> SEQUENCE: 22

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Lys Gln Asp His
50                  55                  60

Lys Tyr Arg Ala Gln Val Asn Phe Gly Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
130                 135                 140

Val Gly Thr Gly Val Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Ser Asn Ile Ser Thr Thr Ser Asn Gln Val Pro
            180                 185                 190

Phe Lys Val Asp Ser Val Gly Asn Leu Tyr Gly Ala Ala Val Gly
            195                 200                 205

Ser Tyr Asp Leu Ala Gly Gly Gln Phe Asn Pro Gln Leu Trp Leu Ala
210                 215                 220
```

-continued

```
Tyr Trp Asp Gln Val Ala Phe Phe Tyr Ala Val Asp Ala Tyr Ser
225                 230                 235                 240

Thr Thr Ile Phe Asp Gly Ile Asn Trp Thr Leu Glu Gly Ala Tyr Leu
            245                 250                 255

Gly Asn Ser Leu Asp Ser Glu Leu Asp Asp Lys Thr His Ala Asn Gly
                260                 265                 270

Asn Leu Phe Ala Leu Lys Gly Ser Ile Glu Val Asn Gly Trp Asp Ala
            275                 280                 285

Ser Leu Gly Gly Leu Tyr Tyr Gly Asp Lys Glu Lys Ala Ser Thr Val
    290                 295                 300

Val Ile Glu Asp Gln Gly Asn Leu Gly Ser Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
            340                 345                 350

Val Gly Ala Asp Phe Val Tyr Gly Gly Thr Lys Thr Glu Ala Ala Asn
        355                 360                 365

His Leu Gly Gly Lys Lys Leu Glu Ala Val Ala Arg Val Asp Tyr
    370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Asp His Ser Thr Val
                405                 410                 415

Arg Leu Gln Ala Leu Tyr Lys Phe
            420

<210> SEQ ID NO 23
<211> LENGTH: 424
<212> TYPE: PRT
<213> ORGANISM: Campylobacter jejuni

<400> SEQUENCE: 23

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Lys Gln Asp His
50                  55                  60

Lys Tyr Arg Ala Gln Val Asn Phe Gly Ala Ala Ile Ala Asp Asn Phe
65                  70                  75                  80

Lys Ala Phe Ile Gln Phe Asp Tyr Asn Ala Val Asp Gly Gly Thr Gly
            85                  90                  95

Val Asp Asn Val Thr Asn Ala Glu Lys Gly Leu Phe Val Arg Gln Leu
        100                 105                 110

Tyr Leu Thr Tyr Thr Asn Glu Asp Val Ala Thr Ser Val Ile Ala Gly
    115                 120                 125

Lys Gln Gln Leu Asn Leu Ile Trp Thr Asp Asn Ala Ile Asp Gly Leu
    130                 135                 140

Val Gly Thr Gly Val Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
```

```
              165                 170                 175
Asp Leu Leu Gly His Ser Asn Ile Ser Thr Thr Ser Asn Gln Ala Pro
            180                 185                 190

Phe Lys Val Asp Ser Val Gly Asn Leu Tyr Gly Ala Ala Ala Val Gly
            195                 200                 205

Ser Tyr Asp Leu Ala Gly Gly Gln Phe Asn Pro Gln Leu Trp Leu Ala
            210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
            245                 250                 255

Gly Asn Ser Leu Asp Ser Glu Leu Asp Asp Gln Ala His Ala Asn Gly
            260                 265                 270

Asn Leu Phe Ala Leu Lys Gly Ser Ile Glu Val Asn Gly Trp Asp Ala
            275                 280                 285

Ser Leu Gly Gly Leu Tyr Tyr Gly Asp Lys Glu Lys Ala Ser Thr Val
            290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
            325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Ala Ala Asn
            355                 360                 365

His Leu Gly Gly Gly Lys Lys Leu Glu Ala Val Ala Arg Val Asp Tyr
            370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
            405                 410                 415

Arg Leu Gln Ala Leu Tyr Lys Phe
            420

<210> SEQ ID NO 24
<211> LENGTH: 425
<212> TYPE: PRT
<213> ORGANISM: Campylobacter jejuni

<400> SEQUENCE: 24

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Lys Gln Asp His
            50                  55                  60

Lys Tyr Arg Ala Gln Val Asn Phe Gly Ala Ala Ile Ala Asp Asn Phe
65                  70                  75                  80

Lys Ala Phe Ile Gln Phe Asp Tyr Asn Ala Val Asp Gly Gly Thr Gly
            85                  90                  95

Val Gly Asn Val Lys Asn Ala Glu Lys Gly Leu Phe Val Arg Gln Leu
            100                 105                 110
```

```
Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
130                 135                 140

Val Gly Thr Gly Val Lys Val Val Asn Asn Ser Ile Asp Gly Leu Thr
145                 150                 155                 160

Leu Ala Ala Phe Ala Ala Asp Ser Phe Met Ala Ala Glu Gln Gly Ala
                165                 170                 175

Asp Leu Leu Gly His Ser Asn Thr Ser Thr Ala Thr Pro Asn Gln Ala
                180                 185                 190

Pro Phe Lys Val Asp Ser Val Gly Asn Leu Tyr Gly Ala Ala Ala Val
                195                 200                 205

Gly Ser Tyr Asp Leu Ala Gly Gly Gln Phe Asn Pro Gln Leu Trp Leu
210                 215                 220

Ala Tyr Trp Asp Gln Val Ala Phe Phe Tyr Ala Val Asp Ala Ala Tyr
225                 230                 235                 240

Ser Thr Thr Ile Phe Asp Gly Ile Asn Trp Thr Leu Glu Gly Ala Tyr
                245                 250                 255

Leu Gly Asn Ser Leu Asp Ser Glu Leu Asp Asp Thr Thr His Ala Asn
                260                 265                 270

Gly Asn Leu Phe Ala Leu Lys Gly Ser Ile Glu Val Asn Gly Trp Asp
                275                 280                 285

Ala Ser Leu Gly Gly Leu Tyr Tyr Gly Asp Lys Glu Lys Ala Ser Thr
                290                 295                 300

Val Val Ile Glu Asp Gln Gly Asn Leu Gly Ser Leu Leu Ala Gly Glu
305                 310                 315                 320

Glu Ile Phe Tyr Thr Thr Gly Ser Arg Leu Asn Gly Asp Thr Gly Arg
                325                 330                 335

Asn Ile Phe Gly Tyr Val Thr Gly Gly Tyr Thr Phe Asn Glu Thr Val
                340                 345                 350

Arg Val Gly Ala Asp Phe Val Tyr Gly Gly Thr Lys Thr Glu Ala Ala
                355                 360                 365

Ser His Leu Gly Gly Lys Lys Leu Glu Ala Val Ala Arg Val Asp
370                 375                 380

Tyr Lys Tyr Ser Pro Lys Leu Asn Phe Ser Ala Phe Tyr Ser Tyr Val
385                 390                 395                 400

Asn Leu Asp Gln Gly Val Asn Thr Asn Glu Ser Ala Asp His Ser Thr
                405                 410                 415

Val Arg Leu Gln Ala Leu Tyr Lys Phe
                420                 425

<210> SEQ ID NO 25
<211> LENGTH: 424
<212> TYPE: PRT
<213> ORGANISM: Campylobacter jejuni

<400> SEQUENCE: 25

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Asn Lys Gln Asp His
        50                  55                  60
```

```
Lys Tyr Arg Ala Gln Val Asn Phe Ser Ala Ala Ile Ala Asp Asn Phe
 65                  70                  75                  80

Lys Ala Phe Ile Gln Phe Asp Tyr Asn Ala Val Asp Gly Gly Thr Gly
                 85                  90                  95

Val Asp Asn Val Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Phe Ile Trp Thr Asp Asn Ala Ile Asp Gly Leu
130                 135                 140

Val Gly Thr Gly Val Lys Val Val Asn Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Glu Leu Leu Gly His Ser Asn Ile Ser Thr Thr Ser Asn Gln Ala Pro
            180                 185                 190

Phe Lys Val Asp Ser Val Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Ile Glu Gly Ala Tyr Leu
                245                 250                 255

Gly Asn Ser Ile Asp Ser Glu Leu Asp Asp Thr Thr His Thr Asn Gly
            260                 265                 270

Asn Phe Phe Ala Leu Lys Gly Gly Ile Glu Val Asn Gly Trp Asp Ala
        275                 280                 285

Ser Leu Gly Gly Leu Tyr Tyr Gly Asp Lys Glu Lys Ala Ser Thr Val
290                 295                 300

Val Ile Glu Asp Gln Gly Asn Leu Ser Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
            340                 345                 350

Val Gly Ala Asp Phe Val Tyr Gly Gly Thr Lys Thr Glu Ala Ala Ser
        355                 360                 365

His Leu Gly Gly Gly Lys Lys Leu Glu Ala Val Ala Arg Val Asp Tyr
370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 26
<211> LENGTH: 417
<212> TYPE: PRT
<213> ORGANISM: Campylobacter jejuni

<400> SEQUENCE: 26

Met Lys Leu Val Lys Leu Ser Leu Val Ala Ala Leu Ala Ala Gly Ala
```

-continued

```
1               5                   10                  15
Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Asn Lys Gln Asp His
50                      55                  60

Lys Tyr Arg Ala Gln Val Asn Phe Ser Ala Ala Ile Ala Asp Asn Phe
65                  70                  75                  80

Lys Ala Phe Ile Gln Phe Asp Tyr Asn Ala Val Asp Gly Gly Thr Gly
                85                  90                  95

Val Asp Asn Ala Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
            115                 120                 125

Lys Gln Gln Leu Asn Leu Ile Trp Thr Asp Asn Ala Ile Asp Gly Leu
            130                 135                 140

Val Gly Thr Gly Val Lys Val Val Asn Asn Ser Ile Asp Gly Leu Thr
145                 150                 155                 160

Leu Ala Ala Phe Ala Val Asp Ser Phe Met Thr Ala Glu Gln Gly Ala
                165                 170                 175

Asp Leu Leu Gly His Asn Gly Ser Gln Phe Asn Pro Asp Ser Ile Gly
            180                 185                 190

Asn Leu Tyr Gly Ala Ala Ala Val Gly Ser Tyr Asp Leu Ala Gly Gly
            195                 200                 205

Gln Phe Asn Pro Gln Leu Trp Leu Ala Tyr Trp Asp Gln Val Ala Phe
            210                 215                 220

Phe Tyr Ala Leu Asp Ala Ser Tyr Ser Thr Thr Ile Phe Asp Gly Ile
225                 230                 235                 240

Asn Trp Thr Leu Glu Gly Ala Tyr Leu Gly Asn Ser Val Asp Ser Asp
                245                 250                 255

Leu Asp Ser Thr Arg Tyr Ala Asn Gly Asn Phe Phe Ala Leu Lys Gly
            260                 265                 270

Gly Ile Glu Val Asn Gly Trp Asp Ala Ser Leu Gly Gly Leu Tyr Tyr
            275                 280                 285

Gly Asp Lys Glu Lys Ala Ser Thr Val Ile Ile Asp Asp Gln Gly Asn
            290                 295                 300

Leu Ser Ser Leu Leu Ala Gly Glu Glu Ile Phe Tyr Thr Thr Gly Ser
305                 310                 315                 320

Arg Leu Asn Gly Asp Thr Gly Arg Asn Ile Phe Gly Tyr Val Thr Gly
                325                 330                 335

Gly Tyr Thr Phe Asn Glu Thr Val Arg Val Gly Ala Asp Phe Val Tyr
            340                 345                 350

Gly Gly Thr Lys Thr Glu Ala Ala Asn His Leu Gly Gly Gly Lys Lys
            355                 360                 365

Leu Glu Ala Val Ala Arg Val Asp Tyr Lys Tyr Ser Pro Lys Leu Asn
            370                 375                 380

Phe Ser Ala Phe Tyr Ser Tyr Val Asn Leu Asp Gln Gly Val Asn Thr
385                 390                 395                 400

Asn Glu Ser Ala Asp His Ser Thr Val Arg Leu Gln Ala Leu Tyr Lys
                405                 410                 415

Phe
```

```
<210> SEQ ID NO 27
<211> LENGTH: 417
<212> TYPE: PRT
<213> ORGANISM: Campylobacter jejuni

<400> SEQUENCE: 27

Met Lys Leu Val Lys Leu Ser Leu Val Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Thr Phe Asp
        35                  40                  45

Lys Asn Trp Gly Thr Pro Asn Ser Asn Leu Asn Asp Ser Lys Gln Asp
    50                  55                  60

His Lys Tyr Arg Ala Gln Val Asn Phe Ser Ala Ile Ala Asp Asn
65                  70                  75                  80

Phe Lys Ala Phe Ile Gln Phe Asp Tyr Asn Ala Val Asp Gly Gly Thr
                85                  90                  95

Gly Val Asp Asn Lys Thr Asn Ala Glu Lys Gly Leu Phe Val Arg Gln
            100                 105                 110

Leu Tyr Leu Thr Tyr Thr Asn Glu Asp Val Ala Thr Ser Val Ile Ala
        115                 120                 125

Gly Lys Gln Gln Leu Asn Ile Ile Trp Thr Asp Asn Gly Val Asp Gly
    130                 135                 140

Leu Val Gly Thr Gly Ile Lys Val Val Asn Asn Ser Ile Asp Gly Leu
145                 150                 155                 160

Thr Leu Ala Ala Phe Ala Val Asp Ser Phe Met Ala Ala Glu Gln Gly
                165                 170                 175

Ser Asp Leu Val Gly Ala Asn Asn Thr Phe Lys Val Asp Ser Ile Gly
            180                 185                 190

Asn Leu Tyr Gly Ala Ala Val Gly Ser Tyr Asp Leu Ala Gly Gly
        195                 200                 205

Gln Phe Asn Pro Gln Leu Trp Leu Ala Tyr Trp Asp Gln Val Ala Phe
    210                 215                 220

Phe Tyr Ala Val Asp Ala Ala Tyr Ser Thr Thr Ile Phe Asp Gly Ile
225                 230                 235                 240

Asn Trp Thr Leu Glu Gly Ala Tyr Leu Gly Asn Ser Val Asp Ser Asp
                245                 250                 255

Leu Asn Ser Ala Glu His Ala Asn Gly Asn Leu Phe Ala Leu Lys Gly
            260                 265                 270

Ser Ile Glu Val Asn Gly Trp Asp Ala Ser Leu Gly Gly Leu Tyr Tyr
        275                 280                 285

Gly Asp Lys Glu Lys Ala Ser Thr Val Val Ile Glu Asp Gln Gly Asn
    290                 295                 300

Leu Gly Ser Leu Leu Ala Gly Glu Glu Ile Phe Tyr Thr Thr Gly Ser
305                 310                 315                 320

Arg Leu Asn Gly Asp Thr Gly Arg Asn Ile Phe Gly Tyr Val Thr Gly
                325                 330                 335

Gly Tyr Thr Phe Asn Glu Thr Val Arg Val Gly Ala Asp Phe Val Tyr
            340                 345                 350

Gly Gly Thr Lys Thr Glu Ala Ala Ser His Leu Gly Gly Lys Lys
        355                 360                 365

Leu Glu Ala Val Ala Arg Val Asp Tyr Lys Tyr Ser Pro Lys Leu Asn
    370                 375                 380
```

```
Phe Ser Ala Phe Tyr Ser Tyr Val Asn Leu Asp Gln Gly Val Asn Thr
385                 390                 395                 400

Asn Glu Ser Ala Asp His Ser Thr Val Arg Leu Gln Ala Leu Tyr Lys
            405                 410                 415

Phe

<210> SEQ ID NO 28
<211> LENGTH: 418
<212> TYPE: PRT
<213> ORGANISM: Campylobacter jejuni

<400> SEQUENCE: 28

Met Lys Leu Val Lys Leu Ser Leu Val Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Thr Phe Asp
            35                  40                  45

Lys Asn Trp Gly Thr Pro Asn Ser Asn Leu Asn Asp Ser Lys Gln Asp
    50                  55                  60

His Lys Tyr Arg Ala Gln Val Asn Phe Ser Ala Ala Ile Ala Asp Asn
65                  70                  75                  80

Phe Lys Ala Phe Ile Gln Phe Asp Tyr Asn Ala Val Asp Gly Gly Thr
                85                  90                  95

Gly Val Asp Asn Lys Thr Asn Ala Glu Lys Gly Leu Phe Val Arg Gln
            100                 105                 110

Leu Tyr Leu Thr Tyr Thr Asn Glu Asp Val Ala Thr Ser Val Ile Ala
        115                 120                 125

Gly Lys Gln Gln Leu Asn Ile Ile Trp Thr Asp Asn Gly Val Asp Gly
    130                 135                 140

Leu Val Gly Thr Gly Ile Lys Val Val Asn Asn Ser Ile Asp Gly Leu
145                 150                 155                 160

Thr Leu Ala Ala Phe Ala Val Asp Ser Phe Met Ala Ala Glu Gln Gly
                165                 170                 175

Ser Asp Leu Val Gly Ala Asn Asn Ser Thr Phe Lys Val Asp Ser Ile
            180                 185                 190

Gly Asn Leu Tyr Gly Ala Ala Val Gly Ser Tyr Asp Leu Ala Gly
        195                 200                 205

Gly Gln Phe Asn Pro Gln Leu Trp Leu Ala Tyr Trp Asp Gln Val Ala
    210                 215                 220

Phe Phe Tyr Ala Leu Asp Val Ser Tyr Ser Thr Thr Ile Phe Asp Gly
225                 230                 235                 240

Ile Asn Trp Thr Leu Glu Gly Ala Tyr Leu Gly Asn Ser Leu Asp Ser
                245                 250                 255

Glu Leu Asn Asp Lys Thr Tyr Ala Asn Gly Asn Leu Phe Ala Leu Lys
            260                 265                 270

Gly Ser Ile Glu Val Asn Gly Trp Asp Ala Ser Leu Gly Gly Leu Tyr
        275                 280                 285

Tyr Gly Asp Lys Glu Lys Ala Ser Thr Val Ala Ile Glu Asp Gln Gly
    290                 295                 300

Asn Leu Gly Ser Leu Leu Ala Gly Glu Glu Ile Phe Tyr Thr Thr Gly
305                 310                 315                 320

Ser Arg Leu Asn Gly Asp Thr Gly Arg Asn Ile Phe Gly Tyr Val Thr
                325                 330                 335
```

```
Gly Gly Tyr Thr Phe Asn Glu Thr Val Arg Val Gly Ala Asp Phe Val
            340                 345                 350

Tyr Gly Gly Thr Lys Thr Glu Ala Ala Gly His Leu Gly Gly Gly Lys
        355                 360                 365

Lys Leu Glu Ala Val Ala Arg Val Asp Tyr Lys Tyr Ser Pro Lys Leu
    370                 375                 380

Asn Phe Ser Ala Phe Tyr Ser Tyr Val Asn Leu Asp Gln Gly Val Asn
385                 390                 395                 400

Thr Asn Glu Ser Ala Asp His Ser Thr Val Arg Leu Gln Ala Leu Tyr
                405                 410                 415

Lys Phe

<210> SEQ ID NO 29
<211> LENGTH: 418
<212> TYPE: PRT
<213> ORGANISM: Campylobacter jejuni

<400> SEQUENCE: 29

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Thr Phe Asp
            35                  40                  45

Lys Asn Trp Gly Thr Pro Asn Ser Asn Leu Asn Asp Ser Lys Gln Asp
    50                  55                  60

His Lys Tyr Arg Ala Gln Val Asn Phe Ser Ala Ala Ile Ala Asp Asn
65                  70                  75                  80

Phe Lys Ala Phe Val Gln Phe Asp Tyr Asn Ala Val Asp Gly Gly Thr
                85                  90                  95

Gly Val Asp Asn Ala Thr Asn Ala Gln Lys Gly Phe Phe Val Arg Gln
            100                 105                 110

Leu Tyr Leu Thr Tyr Thr Asn Glu Asp Val Ala Thr Ser Val Ile Ala
    115                 120                 125

Gly Lys Gln Gln Leu Asn Ile Ile Trp Thr Asp Asn Gly Ile Asp Gly
    130                 135                 140

Leu Val Gly Thr Gly Val Lys Val Val Asn Asn Ser Ile Asp Gly Leu
145                 150                 155                 160

Thr Leu Ala Ala Phe Ala Val Asp Ser Phe Met Ala Thr Glu Gln Gly
                165                 170                 175

Ser Asp Leu Val Gly His Asn Gly Ser Gln Phe Asn Pro Asp Ser Ile
            180                 185                 190

Gly Asn Leu Tyr Gly Ala Ala Val Gly Ser Tyr Asp Leu Ala Gly
    195                 200                 205

Gly Gln Phe Asn Pro Gln Leu Trp Leu Ala Tyr Trp Asp Gln Val Ala
    210                 215                 220

Phe Phe Tyr Ala Leu Asp Ala Ser Tyr Ser Thr Thr Ile Phe Asp Gly
225                 230                 235                 240

Ile Asn Trp Thr Leu Glu Gly Ala Tyr Leu Gly Asn Ser Val Asp Ser
                245                 250                 255

Asp Leu Asp Ser Ala Lys Tyr Ala Asn Gly Asn Leu Phe Ala Leu Lys
            260                 265                 270

Gly Ser Ile Glu Val Asn Gly Trp Asp Ala Ser Leu Gly Gly Leu Tyr
    275                 280                 285
```

```
Tyr Gly Asp Lys Glu Lys Ala Ser Thr Val Val Ile Glu Asp Gln Gly
            290                 295                 300

Asn Leu Gly Ser Leu Leu Ala Gly Glu Glu Ile Phe Tyr Thr Thr Gly
305                 310                 315                 320

Ser Arg Leu Asn Gly Asp Thr Gly Arg Asn Ile Phe Gly Tyr Val Thr
                325                 330                 335

Gly Gly Tyr Thr Phe Asn Glu Thr Val Arg Val Gly Ala Asp Phe Val
            340                 345                 350

Tyr Gly Gly Thr Lys Thr Glu Ala Ala Asn His Leu Gly Gly Gly Lys
            355                 360                 365

Lys Leu Glu Ala Val Ala Arg Val Asp Tyr Lys Tyr Ser Pro Lys Leu
370                 375                 380

Asn Phe Ser Ala Phe Tyr Ser Tyr Val Asn Leu Asp Gln Gly Val Asn
385                 390                 395                 400

Thr Asn Glu Ser Ala Asp His Ser Thr Val Arg Leu Gln Ala Leu Tyr
                405                 410                 415

Lys Phe

<210> SEQ ID NO 30
<211> LENGTH: 418
<212> TYPE: PRT
<213> ORGANISM: Campylobacter jejuni

<400> SEQUENCE: 30

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Thr Phe Asp
            35                  40                  45

Lys Asn Trp Gly Thr Pro Asn Ser Asn Leu Asn Asp Ser Lys Gln Asp
        50                  55                  60

His Lys Tyr Arg Ala Gln Val Asn Phe Ser Ala Ile Ala Asp Asn
65                  70                  75                  80

Phe Lys Ala Phe Val Gln Phe Asp Tyr Asn Ala Val Asp Gly Gly Thr
                85                  90                  95

Gly Val Asp Asn Ala Thr Asn Ala Gln Lys Gly Phe Phe Val Arg Gln
            100                 105                 110

Leu Tyr Leu Thr Tyr Thr Asn Glu Asp Val Ala Thr Ser Val Ile Ala
            115                 120                 125

Gly Lys Gln Gln Leu Asn Ile Ile Trp Thr Asp Asn Gly Ile Asp Gly
        130                 135                 140

Leu Val Gly Thr Gly Val Lys Val Val Asn Asn Ser Ile Asp Gly Leu
145                 150                 155                 160

Thr Leu Ala Ala Phe Ala Val Asp Ser Phe Met Ala Thr Glu Gln Gly
                165                 170                 175

Ser Asp Leu Val Gly His Asn Gly Ser Gln Phe Asn Pro Asp Ser Ile
            180                 185                 190

Gly Asn Leu Tyr Gly Ala Ala Val Gly Ser Tyr Asp Leu Ala Gly
        195                 200                 205

Gly Gln Phe Asn Pro Gly Leu Trp Leu Ala Tyr Trp Asp Gln Val Ala
    210                 215                 220

Phe Phe Tyr Ala Leu Asp Ala Ser Tyr Ser Thr Thr Ile Phe Asp Gly
225                 230                 235                 240
```

```
Ile Asn Trp Thr Leu Glu Gly Ala Tyr Leu Gly Asn Ser Val Asp Ser
                245                 250                 255

Asp Leu Asp Ser Ala Arg Tyr Ala Asn Gly Asn Leu Phe Ala Leu Lys
            260                 265                 270

Gly Ser Ile Glu Val Asn Gly Trp Asp Ala Ser Leu Gly Gly Leu Tyr
        275                 280                 285

Tyr Gly Asp Lys Glu Lys Ala Ser Thr Val Val Ile Glu Asp Gln Gly
    290                 295                 300

Asn Leu Gly Ser Leu Leu Ala Gly Glu Glu Ile Phe Tyr Thr Thr Gly
305                 310                 315                 320

Ser Arg Leu Asn Gly Asp Thr Gly Arg Asn Ile Phe Gly Tyr Val Thr
                325                 330                 335

Gly Gly Tyr Thr Phe Asn Glu Thr Val Arg Val Gly Ala Asp Phe Val
            340                 345                 350

Tyr Gly Gly Thr Lys Thr Glu Ala Ala Asn His Leu Gly Gly Gly Lys
        355                 360                 365

Lys Leu Glu Ala Val Ala Arg Val Asp Tyr Lys Tyr Ser Pro Lys Leu
    370                 375                 380

Asn Phe Ser Ala Phe Tyr Ser Tyr Val Asn Leu Asp Gln Gly Val Asn
385                 390                 395                 400

Thr Asn Glu Ser Ala Asp His Ser Thr Val Arg Leu Gln Ala Leu Tyr
                405                 410                 415

Lys Phe

<210> SEQ ID NO 31
<211> LENGTH: 418
<212> TYPE: PRT
<213> ORGANISM: Campylobacter jejuni

<400> SEQUENCE: 31

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Thr Phe Asp
            35                  40                  45

Lys Asn Trp Gly Thr Pro Asn Ser Asn Leu Asn Asp Ser Lys Gln Asp
        50                  55                  60

His Lys Tyr Arg Ala Gln Val Asn Phe Ser Ala Ala Ile Ala Asp Asn
65                  70                  75                  80

Phe Lys Ala Phe Ile Gln Phe Asp Tyr Asn Ala Val Asp Gly Gly Thr
                85                  90                  95

Gly Val Asp Asn Ala Thr Asn Ala Glu Lys Gly Leu Phe Val Arg Gln
            100                 105                 110

Leu Tyr Leu Thr Tyr Thr Asn Glu Asp Val Ala Thr Ser Val Ile Ala
        115                 120                 125

Gly Lys Gln Gln Leu Asn Thr Ile Trp Thr Asn Gly Ile Asp Gly
    130                 135                 140

Leu Val Gly Thr Gly Val Lys Val Val Asn Asn Ser Ile Asp Gly Leu
145                 150                 155                 160

Thr Leu Ala Ala Phe Ala Val Asp Ser Phe Met Ala Thr Glu Gln Gly
                165                 170                 175

Ser Asp Leu Val Gly His Asn Gly Ser Lys Phe Ser Pro Asp Ser Ile
            180                 185                 190
```

-continued

```
Gly Asn Leu Tyr Gly Ala Ala Val Gly Ser Tyr Asp Leu Ala Gly
            195                 200                 205

Gly Gln Phe Asn Pro Gln Leu Trp Leu Ala Tyr Trp Asp Gln Val Ala
        210                 215                 220

Phe Phe Tyr Ala Leu Asp Ala Ser Tyr Ser Thr Thr Ile Phe Asp Gly
225                 230                 235                 240

Ile Asn Trp Thr Leu Glu Gly Ala Tyr Leu Gly Asn Ser Val Asp Ser
                245                 250                 255

Asp Leu Asn Ser Ala Glu Tyr Ala Asn Gly Asn Leu Phe Ala Leu Lys
            260                 265                 270

Gly Ser Ile Glu Val Asn Gly Trp Asp Ala Ser Leu Gly Gly Leu Tyr
        275                 280                 285

Tyr Gly Asp Lys Glu Lys Ala Ser Thr Val Val Ile Glu Asp Gln Gly
    290                 295                 300

Asn Leu Gly Ser Leu Leu Ala Gly Glu Glu Ile Phe Tyr Thr Thr Gly
305                 310                 315                 320

Ser Arg Leu Asn Gly Asp Thr Gly Arg Asn Ile Phe Gly Tyr Val Thr
                325                 330                 335

Gly Gly Tyr Thr Phe Asn Glu Thr Val Arg Val Gly Ala Asp Phe Val
            340                 345                 350

Tyr Gly Gly Thr Lys Thr Glu Ala Thr Thr His Leu Gly Gly Gly Lys
        355                 360                 365

Lys Leu Glu Ala Val Ala Arg Val Asp Tyr Lys Tyr Ser Pro Lys Leu
    370                 375                 380

Asn Phe Ser Ala Phe Tyr Ser Tyr Val Asn Leu Asp Gln Gly Val Asn
385                 390                 395                 400

Thr Asn Glu Ser Ala Asp His Ser Thr Val Arg Leu Gln Ala Leu Tyr
                405                 410                 415

Lys Phe

<210> SEQ ID NO 32
<211> LENGTH: 425
<212> TYPE: PRT
<213> ORGANISM: Campylobacter jejuni

<400> SEQUENCE: 32

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Leu Asn Asn Ser Asn Leu Asn Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Val Asp Gly Gly Thr Gly
                85                  90                  95

Val Asp Asn Ala Thr Asn Ala Glu Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Ile Ile Trp Thr Asp Asn Gly Val Asp Gly Leu
    130                 135                 140
```

Val Gly Thr Gly Val Lys Trp Asn Asn Ser Ile Asp Gly Leu Thr Leu
145                 150                 155                 160

Ala Ala Phe Ala Val Asp Ser Phe Met Ala Thr Glu Gln Gly Ser Asp
            165                 170                 175

Leu Leu Gly Gln Ser Thr Tyr Val Ser Asn Asp Lys Asn Asn Asn Asp
            180                 185                 190

Ser Phe Lys Leu Asp Ser Ile Gly Asn Leu Tyr Gly Ala Ala Ala Val
            195                 200                 205

Gly Ser Tyr Asp Leu Ala Gly Gly Gln Phe Asn Pro Gln Leu Trp Leu
            210                 215                 220

Ala Tyr Trp Asp Gln Val Ala Phe Phe Tyr Ala Val Ala Ala Tyr
225                 230                 235                 240

Ser Thr Thr Ile Phe Asp Gly Ile Asn Trp Thr Leu Glu Gly Ala Tyr
            245                 250                 255

Leu Gly Asn Ser Leu Asp Ser Glu Leu Asp Asp Arg Thr Tyr Ala Asn
            260                 265                 270

Gly Asn Leu Phe Ala Leu Lys Gly Ser Ile Glu Val Asn Gly Trp Asp
            275                 280                 285

Ala Ser Leu Gly Gly Leu Tyr Tyr Gly Asp Lys Glu Lys Ala Ser Thr
290                 295                 300

Val Val Ile Glu Asp Gln Gly Asn Leu Gly Ser Leu Leu Ala Gly Glu
305                 310                 315                 320

Glu Ile Phe Tyr Thr Thr Gly Ser Arg Leu Asn Gly Asp Thr Gly Arg
            325                 330                 335

Asn Ile Phe Gly Tyr Val Thr Gly Gly Tyr Thr Phe Asn Glu Thr Val
            340                 345                 350

Arg Val Gly Ala Asp Phe Val Tyr Gly Gly Thr Lys Thr Glu Ala Val
            355                 360                 365

Gly His Leu Gly Gly Gly Lys Lys Leu Glu Ala Val Ala Arg Val Asp
            370                 375                 380

Tyr Lys Tyr Ser Pro Lys Leu Asn Phe Ser Ala Phe Tyr Ser Tyr Val
385                 390                 395                 400

Asn Leu Asp Gln Gly Val Asn Thr Asn Glu Ser Ala Asp His Ser Thr
            405                 410                 415

Val Arg Leu Gln Ala Leu Tyr Lys Phe
            420                 425

<210> SEQ ID NO 33
<211> LENGTH: 424
<212> TYPE: PRT
<213> ORGANISM: Campylobacter jejuni

<400> SEQUENCE: 33

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
            35                  40                  45

Lys Asn Phe Ile Asn Asn Ser Asn Leu Asn Asn Ser Lys Gln Asp His
            50                  55                  60

Lys Tyr Arg Ala Gln Val Asn Phe Ser Ala Ile Ala Asp Asn Phe
65                  70                  75                  80

Lys Ala Phe Val Gln Phe Asp Tyr Asn Ala Ala Asp Gly Gly Thr Gly

```
                        85                  90                  95
Val Asp Asn Ala Thr Asn Ala Gln Lys Gly Leu Phe Val Arg Gln Leu
                100                 105                 110

Tyr Leu Thr Tyr Thr Asn Glu Asp Val Ala Thr Ser Val Ile Ala Gly
                115                 120                 125

Lys Gln Gln Leu Asn Thr Ile Trp Thr Asp Asn Gly Ile Asp Gly Leu
                130                 135                 140

Val Gly Thr Gly Val Lys Val Asn Asn Ser Ile Asp Gly Leu Thr
145                 150                 155                 160

Leu Ala Ala Phe Ala Val Asp Ser Phe Met Ala Glu Glu Gln Gly Ala
                165                 170                 175

Asp Leu Leu Gly His Ser Asn Ile Ser Ser Ala Asn Asn Ser Ala Pro
                180                 185                 190

Phe Lys Leu Asp Ser Ile Gly Asn Leu Tyr Gly Gly Ala Ala Val Gly
                195                 200                 205

Ser Tyr Glu Phe Leu Gly Gly Gln Phe Asn Pro Gln Leu Trp Leu Ala
                210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Ile Asp Ser Glu Leu Asp Lys Thr Thr His Thr Asn Gly
                260                 265                 270

Asn Leu Phe Ala Leu Arg Gly Ser Val Glu Leu Asn Gly Trp Asp Ala
                275                 280                 285

Ser Leu Gly Gly Leu Tyr Tyr Gly Asp Lys Glu Lys Ala Ser Thr Val
290                 295                 300

Val Ile Glu Asp Gln Gly Asn Ile Gly Ser Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Tyr Thr Phe Asn Glu Thr Val Arg
                340                 345                 350

Val Gly Ala Asp Phe Val Tyr Gly Gly Thr Lys Thr Glu Thr Ala Gly
                355                 360                 365

His Leu Gly Gly Lys Lys Leu Glu Ala Val Ala Arg Val Asp Tyr
                370                 375                 380

Lys Tyr Ser Pro Lys Leu Asn Phe Ser Ala Phe Tyr Ser Tyr Val Asn
385                 390                 395                 400

Leu Asp Glu Gly Val Asn Thr Lys Glu Ser Ala Asp His Ser Thr Val
                405                 410                 415

Arg Leu Gln Ala Leu Tyr Lys Phe
                420

<210> SEQ ID NO 34
<211> LENGTH: 425
<212> TYPE: PRT
<213> ORGANISM: Campylobacter jejuni

<400> SEQUENCE: 34

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30
```

```
Asp Val Ser Gly Val Leu Arg Arg Tyr Asp Thr Gly Asn Phe Asp
         35                  40                  45

Lys Asn Phe Ile Asn Asn Ser Asn Leu Asn Asn Ser Lys Gln Asp His
 50                  55                  60

Lys Tyr Arg Ala Gln Val Asn Phe Ser Ala Ala Ile Ala Asp Asn Phe
 65                  70                  75                  80

Lys Ala Phe Val Gln Phe Asp Tyr Asn Ala Ala Asp Gly Gly Tyr Gly
                 85                  90                  95

Ala Asn Glu Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Thr Ile Trp Thr Asp Asn Gly Ile Asp Gly Leu
130                 135                 140

Val Gly Thr Gly Val Lys Val Ile Asn Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Asp Leu Leu Gly His Ser Asn Ile Ser Ser Ala Lys Pro Asn Ile Ala
            180                 185                 190

Pro Phe Lys Leu Asp Ser Ile Gly Asn Leu Tyr Gly Gly Ala Ala Val
        195                 200                 205

Gly Ser Tyr Glu Phe Leu Gly Gln Phe Asn Pro Gln Leu Trp Leu
    210                 215                 220

Ala Tyr Trp Asp Gln Val Ala Phe Phe Tyr Ala Val Asp Ala Ala Tyr
225                 230                 235                 240

Ser Thr Thr Ile Phe Asp Gly Ile Asn Trp Thr Leu Glu Gly Ala Tyr
                245                 250                 255

Leu Gly Asn Ser Ile Asp Ser Glu Leu Asp Asp Lys Thr His Thr Asn
            260                 265                 270

Gly Asn Leu Phe Ala Leu Arg Gly Ser Val Glu Leu Asn Gly Trp Asp
        275                 280                 285

Ala Ser Leu Gly Gly Leu Tyr Tyr Gly Asp Lys Glu Lys Ala Ser Thr
290                 295                 300

Val Val Ile Glu Asp Gln Gly Asn Ile Gly Ser Leu Leu Ala Gly Glu
305                 310                 315                 320

Glu Ile Phe Tyr Thr Thr Gly Ser Arg Leu Asn Gly Asp Thr Gly Arg
                325                 330                 335

Asn Ile Phe Gly Tyr Val Thr Gly Gly Tyr Thr Phe Asn Glu Thr Val
            340                 345                 350

Arg Val Gly Ala Asp Phe Val Tyr Gly Gly Thr Lys Thr Glu Ala Ala
        355                 360                 365

Asn His Leu Gly Gly Gly Lys Lys Leu Glu Ala Val Ala Arg Val Asp
370                 375                 380

Tyr Lys Tyr Ser Pro Lys Leu Asn Phe Ser Ala Phe Tyr Ser Tyr Val
385                 390                 395                 400

Asn Leu Asp Glu Gly Val Asn Thr Lys Glu Ser Ala Asp His Ser Thr
                405                 410                 415

Val Arg Leu Gln Ala Leu Tyr Lys Phe
            420                 425

<210> SEQ ID NO 35
<211> LENGTH: 420
<212> TYPE: PRT
```

<213> ORGANISM: Campylobacter jejuni

<400> SEQUENCE: 35

```
Met Lys Leu Val Lys Leu Ser Leu Val Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Glu Thr Ser Asn Asp Trp
        35                  40                  45

Ser Asn Ala Asn Phe Gly Ser Gly Ile Ser Gly Lys Gln Asp His Lys
    50                  55                  60

Tyr Arg Ala Gln Val Asn Phe Gly Ala Ala Ser Ala Asp Asn Phe Lys
65                  70                  75                  80

Ala Phe Val Gln Phe Asp Tyr Ser Gln Ala Asp Gly Gly Tyr Gly Ala
                85                  90                  95

Asp Ser Ile Ser Asn Thr Ser Asp Thr Leu Ser Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Gly Ile Asp Gly Leu Val
130                 135                 140

Gly Thr Gly Ile Lys Val Val Asn Asn Ser Ile Asp Gly Leu Thr Leu
145                 150                 155                 160

Ala Ala Phe Ala Met Asp Ser Phe Asn Glu Glu Val Pro Ala Thr Thr
                165                 170                 175

Thr Asn Gly Phe Asn Lys Gly Asn Val Asn Gly Asp Gly Asp Val Ser
            180                 185                 190

Ser Ala Leu Asp Trp Ser Lys Asn Ile Tyr Gly Ala Ala Ile Gly
            195                 200                 205

Ser Tyr Asp Leu Ile Gly Gly Gln Phe Asn Pro Gln Leu Trp Leu Ala
    210                 215                 220

Tyr Met Ser Asp Asn Ala Phe Leu Tyr Ala Leu Asp Ala Ala Tyr Ser
225                 230                 235                 240

Thr Thr Ile Phe Asp Gly Ile Asn Trp Ser Ile Glu Gly Ala Tyr Leu
                245                 250                 255

Gly Asn Ser Val Asp Asn Lys Leu Lys Asp Arg Leu Asp Ala Ala Asn
            260                 265                 270

Gly Asn Phe Phe Ala Leu Arg Gly Thr Val Glu Val Asn Gly Trp Asp
        275                 280                 285

Ala Ser Leu Gly Gly Leu Tyr Gly Lys Lys Asp Lys Ala Thr Val
    290                 295                 300

Thr Thr Ile Glu Asp Gln Gly Asn Ile Gly Ser Leu Leu Ala Gly Glu
305                 310                 315                 320

Glu Ile Phe Tyr Thr Arg Gly Ser Asn Leu Asn Gly Asp Ile Gly Arg
                325                 330                 335

Asn Ile Phe Gly Tyr Val Thr Gly Tyr Thr Phe Asn Glu Thr Val
            340                 345                 350

Arg Val Gly Ala Asp Phe Val Tyr Gly Thr Lys Thr Asn Ile Ile
        355                 360                 365

Gly Gly Gly Gly Lys Lys Leu Glu Ala Val Ala Arg Val Asp Tyr Lys
    370                 375                 380

Tyr Ser Pro Lys Leu Asn Phe Ser Ala Phe Tyr Ser Tyr Val Asn Val
385                 390                 395                 400
```

Asp Thr Asp Pro Glu Ser Thr His His Asp Ala Val Arg Leu Gln Ala
                405                 410                 415

Leu Tyr Lys Phe
            420

<210> SEQ ID NO 36
<211> LENGTH: 421
<212> TYPE: PRT
<213> ORGANISM: Campylobacter jejuni

<400> SEQUENCE: 36

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Thr Ser Asn Asp Trp
            35                  40                  45

Ser Asn Ala Asn Phe Gly Ser Gly Ile Ser Lys Gln Asp His Lys
        50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Tyr Gly Ala
                85                  90                  95

Asp Ser Ile Ser Asn Thr Ser Asp Thr Leu Ser Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Gly Ile Asp Gly Leu Val
    130                 135                 140

Gly Thr Gly Ile Lys Val Val Asn Asn Ser Ile Asp Gly Leu Thr Leu
145                 150                 155                 160

Ala Ala Phe Ala Met Asp Ser Phe Asn Glu Glu Val Pro Ala Thr Thr
                165                 170                 175

Thr Asn Gly Asn Phe Asn Lys Gly Asn Val Asn Gly Asp Gly Asp Val
            180                 185                 190

Ser Ser Ala Leu Asp Trp Ser Lys Asn Ile Tyr Gly Ala Ala Ala Ile
        195                 200                 205

Gly Ser Tyr Asp Ile Ala Gly Gly Gln Phe Asn Pro Gln Leu Trp Leu
    210                 215                 220

Ala Tyr Met Ser Asp Asn Ala Phe Leu Tyr Ala Leu Asp Ala Ala Tyr
225                 230                 235                 240

Ser Thr Thr Ile Phe Asp Gly Ile Asn Trp Ser Ile Glu Gly Ala Tyr
                245                 250                 255

Leu Gly Asn Ser Val Asp Asn Lys Leu Lys Asp Arg Leu Asp Ala Ala
            260                 265                 270

Asn Gly Asn Phe Phe Ala Leu Arg Gly Thr Val Glu Val Asn Gly Trp
        275                 280                 285

Asp Ala Ser Leu Gly Gly Leu Tyr Tyr Gly Lys Lys Asp Lys Ala Thr
    290                 295                 300

Val Thr Thr Ile Glu Asp Gln Gly Asn Ile Gly Ser Leu Leu Ala Gly
305                 310                 315                 320

Glu Glu Ile Phe Tyr Thr Arg Gly Ser Asn Leu Asn Gly Asp Ile Gly
                325                 330                 335

Arg Asn Ile Phe Gly Tyr Val Thr Gly Gly Tyr Thr Phe Asn Glu Thr
            340                 345                 350

```
Val Arg Val Gly Ala Asp Phe Val Tyr Gly Gly Thr Lys Thr Asn Ile
        355                 360                 365

Ile Gly Gln Gly Gly Lys Lys Leu Glu Ala Val Ala Arg Val Asp Tyr
370                 375                 380

Lys Tyr Ser Pro Lys Leu Asn Phe Ser Ala Phe Tyr Ser Tyr Val Asn
385                 390                 395                 400

Val Asp Thr Asp Pro Glu Ser Thr His His Asp Ala Val Arg Leu Gln
                405                 410                 415

Ala Leu Tyr Lys Phe
            420

<210> SEQ ID NO 37
<211> LENGTH: 431
<212> TYPE: PRT
<213> ORGANISM: Campylobacter jejuni

<400> SEQUENCE: 37

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Ser Ser Asn Pro Trp
            35                  40                  45

Ser Asn Ala Asn Phe Gly Ser Gly Ile Ser Gly Lys Gln Asp His Lys
        50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Gly Tyr Gly Ala
                85                  90                  95

Asp Ser Ile Ser Asn Thr Ser Asp Thr Leu Ser Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Ala Ile Asp Gly Leu Val
130                 135                 140

Gly Thr Gly Ile Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asp Asn Ser Gln Lys Ile Thr Gly Val Gln Phe Asn
            180                 185                 190

Arg Gly Asn Pro Lys Gly Asp Ser Asp Val Ser Gly Ala Leu Asp Trp
        195                 200                 205

Ser Lys Asn Ile Tyr Gly Ala Ala Ile Gly Ser Tyr Asp Ile Ala
210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Thr Tyr Ser Thr Ile Phe Asp
                245                 250                 255

Gly Ile Asn Trp Thr Ile Glu Gly Ala Tyr Leu Gly Asn Ser Val Asp
            260                 265                 270

Asn Lys Leu Lys Asp Arg Leu Asp Ala Ala Asn Gly Asn Phe Phe Ala
        275                 280                 285

Leu Arg Gly Thr Val Glu Val Asn Gly Trp Asp Ala Ser Leu Gly Gly
```

```
            290                 295                 300
Leu Tyr Tyr Gly Lys Lys Asp Lys Ile Thr Val Thr Thr Ile Glu Asp
305                 310                 315                 320

Gln Gly Asn Leu Gly Ser Leu Leu Ala Gly Glu Ile Phe Tyr Thr
                325                 330                 335

Arg Gly Ser Asn Leu Asn Gly Asp Leu Gly Arg Asn Ile Phe Gly Tyr
                340                 345                 350

Val Thr Gly Gly Tyr Thr Phe Asn Glu Ala Val Arg Val Gly Ala Asp
                355                 360                 365

Phe Val Tyr Gly Gly Thr Lys Thr Asn Ile Ile Gly Gln Gly Lys
370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
                420                 425                 430
```

<210> SEQ ID NO 38
<211> LENGTH: 430
<212> TYPE: PRT
<213> ORGANISM: Campylobacter jejuni

<400> SEQUENCE: 38

```
Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Ser Ser Asn Pro Trp
                35                  40                  45

Ser Asn Ala Asn Phe Gly Ser Gly Ile Ser Gly Lys Gln Asp His Lys
50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Tyr Gly Ala
                85                  90                  95

Asp Ser Ile Ser Asn Thr Ser Asp Thr Leu Ser Val Arg Gln Leu Tyr
                100                 105                 110

Leu Thr Tyr Thr Asn Glu Asp Val Ala Thr Ser Val Ile Ala Gly Lys
                115                 120                 125

Gln Gln Leu Asn Thr Ile Trp Thr Asp Asn Ala Ile Asp Gly Leu Val
                130                 135                 140

Gly Thr Gly Ile Lys Trp Asn Asn Ser Ile Asp Gly Leu Thr Leu Ala
145                 150                 155                 160

Ala Phe Ala Met Asp Ser Phe Asn Glu Ala Ser Asp Thr Thr Val Thr
                165                 170                 175

Ile Thr Gln Asp Asn Ser Gln Lys Ile Thr Gly Val Gln Phe Asn Arg
                180                 185                 190

Gly Asn Pro Lys Gly Asp Ser Asp Val Ser Gly Ala Leu Asp Trp Ser
                195                 200                 205

Lys Asn Ile Tyr Gly Ala Thr Ala Ile Gly Ser Tyr Asp Ile Ala Gly
                210                 215                 220

Gly Gln Phe Asn Pro Gln Leu Trp Leu Ala Tyr Met Ser Asp Asn Ala
225                 230                 235                 240
```

```
Phe Leu Tyr Ala Leu Asp Ala Thr Tyr Ser Thr Thr Ile Phe Asp Gly
                245                 250                 255

Ile Asn Trp Thr Ile Glu Gly Ala Tyr Leu Gly Asn Ser Val Asp Asn
            260                 265                 270

Lys Leu Lys Asp Arg Leu Asp Ala Ala Asn Gly Asn Phe Phe Ala Leu
        275                 280                 285

Arg Gly Thr Val Glu Val Asn Gly Trp Asp Ala Ser Leu Gly Gly Leu
    290                 295                 300

Tyr Tyr Gly Lys Lys Asp Lys Ile Thr Val Thr Ile Glu Asp Gln
305                 310                 315                 320

Gly Asn Leu Gly Ser Leu Leu Ala Gly Glu Glu Ile Phe Tyr Thr Arg
                325                 330                 335

Gly Ser Asn Leu Asn Gly Asp Leu Gly Arg Asn Ile Phe Gly Tyr Val
            340                 345                 350

Thr Gly Gly Tyr Thr Phe Asn Glu Ala Val Arg Val Gly Ala Asp Phe
        355                 360                 365

Val Tyr Gly Gly Thr Lys Thr Asn Ile Ile Gly Gln Gly Gly Lys Lys
    370                 375                 380

Leu Glu Ala Val Ala Arg Val Asp Tyr Lys Tyr Ser Pro Lys Leu Asn
385                 390                 395                 400

Phe Ser Ala Phe Tyr Ser Tyr Val Asn Val Asp Thr Asp Pro Glu Ser
                405                 410                 415

Thr His His Asp Ala Val Lys Leu Gln Ala Leu Tyr Lys Phe
            420                 425                 430

<210> SEQ ID NO 39
<211> LENGTH: 431
<212> TYPE: PRT
<213> ORGANISM: Campylobacter jejuni

<400> SEQUENCE: 39

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Ile
            20                  25                  30

Asp Val Ser Gly Val Leu Arg Tyr Arg Tyr Glu Ser Ser Asn Pro Trp
        35                  40                  45

Ser Asn Ala Asn Phe Gly Ser Gly Ile Ser Gly Lys Gln Asp His Lys
    50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Tyr Gly Thr
                85                  90                  95

Asp Ser Ile Ser Asn Thr Ser Asp Thr Leu Thr Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Gly Ile Asp Gly Leu Val
    130                 135                 140

Gly Thr Gly Val Lys Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asp Ser Asn Gln Lys Ile Thr Gly Val Gln Phe Asn
            180                 185                 190
```

```
Arg Gly Asn Pro Lys Gly Asp Ser Asp Val Ser Gly Ala Leu Asp Trp
        195                 200                 205

Ser Lys Asn Ile Tyr Gly Ala Ala Ile Gly Ser Tyr Asp Ile Ala
    210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asp
                245                 250                 255

Gly Ile Asn Trp Thr Ile Glu Gly Ala Tyr Leu Gly Asn Ser Val Asp
                260                 265                 270

Asn Lys Leu Lys Asp Arg Leu Asp Ala Ala Asn Gly Asn Phe Phe Ala
                275                 280                 285

Leu Arg Gly Thr Val Glu Val Asn Gly Trp Asp Ala Ser Leu Gly Gly
    290                 295                 300

Leu Tyr Tyr Gly Lys Lys Asp Lys Ile Thr Val Thr Thr Ile Glu Asp
305                 310                 315                 320

Gln Gly Asn Leu Gly Ser Leu Ala Gly Glu Ile Phe Tyr Thr
                325                 330                 335

Arg Gly Ser Asn Leu Asn Gly Asp Leu Gly Arg Asn Ile Phe Gly Tyr
                340                 345                 350

Val Thr Gly Gly Tyr Thr Phe Asn Glu Ala Val Arg Val Gly Ala Asp
        355                 360                 365

Phe Val Tyr Gly Gly Thr Lys Thr Asn Ile Ile Gly Gln Gly Gly Lys
        370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
                420                 425                 430

<210> SEQ ID NO 40
<211> LENGTH: 431
<212> TYPE: PRT
<213> ORGANISM: Campylobacter jejuni

<400> SEQUENCE: 40

Met Lys Leu Val Lys Leu Ser Leu Val Ala Ala Leu Ala Ala Ser Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Ser Ser Asn Pro Trp
            35                  40                  45

Ser Asn Ala Asn Phe Gly Ser Gly Ile Ser Gly Lys Gln Asp His Lys
    50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Tyr Gly Thr
                85                  90                  95

Asp Ser Ile Ser Asn Thr Ser Asp Thr Leu Thr Val Arg Gln Leu Tyr
                100                 105                 110

Leu Thr Tyr Thr Asn Glu Asp Val Ala Thr Ser Val Ile Ala Gly Lys
            115                 120                 125

Gln Gln Leu Asn Thr Ile Trp Thr Asp Asn Gly Val Asp Gly Leu Val
```

```
            130                 135                 140
Gly Thr Gly Ile Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asn Ser Ser Gln Lys Ile Thr Gly Val Gln Phe Asn
                180                 185                 190

Arg Gly Asn Pro Lys Gly Asp Gly Asp Val Ser Gly Ala Leu Asp Trp
                195                 200                 205

Ser Lys Asn Ile Tyr Gly Ala Ala Ile Gly Ser Tyr Asp Ile Thr
        210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asp
                245                 250                 255

Gly Ile Asn Trp Ser Ile Glu Gly Ala Tyr Leu Gly Asn Ser Val Asp
                260                 265                 270

Asn Lys Leu Lys Asp Arg Leu Gly Val Ala Asn Gly Asn Phe Phe Ala
                275                 280                 285

Leu Arg Gly Thr Val Glu Val Asn Gly Trp Asp Ala Ser Leu Gly Gly
        290                 295                 300

Leu Tyr Tyr Gly Lys Lys Asp Lys Val Thr Val Thr Thr Ile Glu Asp
305                 310                 315                 320

Gln Gly Asn Leu Gly Ser Leu Leu Ala Gly Glu Glu Ile Phe Tyr Thr
                325                 330                 335

Arg Gly Ser Asn Leu Asn Gly Asp Leu Gly Arg Asn Ile Phe Gly Tyr
                340                 345                 350

Val Thr Gly Gly Tyr Thr Phe Asn Glu Ala Val Arg Val Gly Ala Asp
                355                 360                 365

Phe Val Tyr Gly Gly Thr Lys Thr Asn Ile Ile Gly Gln Gly Gly Lys
                370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
                420                 425                 430

<210> SEQ ID NO 41
<211> LENGTH: 431
<212> TYPE: PRT
<213> ORGANISM: Campylobacter jejuni

<400> SEQUENCE: 41

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Ser Ser Asn Pro Trp
            35                  40                  45

Ser Asn Ala Asn Phe Gly Ser Gly Ile Ser Gly Lys Gln Asp His Lys
        50                  55                  60

Tyr Arg Ala Gln Val Asn Phe Ser Gly Ala Ile Ser Asp Asn Phe Lys
65                  70                  75                  80
```

```
Ala Phe Val Gln Phe Asp Tyr Asn Ser Gln Asp Gly Gly Tyr Gly Thr
                85                  90                  95

Asp Ser Ile Ser Asn Thr Ser Asp Thr Leu Thr Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Gly Ile Asp Gly Leu Val
    130                 135                 140

Gly Thr Gly Val Lys Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asp Asn Asn Gln Lys Ile Thr Gly Val Gln Phe Asn
            180                 185                 190

Arg Gly Asn Pro Lys Gly Asp Ser Asp Val Ser Gly Ala Leu Asp Trp
        195                 200                 205

Ser Lys Asn Ile Tyr Gly Ala Ala Ala Ile Gly Ser Tyr Asp Ile Ala
    210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asp
                245                 250                 255

Gly Ile Asn Trp Thr Ile Glu Gly Ala Tyr Leu Gly Asn Ser Val Asp
            260                 265                 270

Asn Lys Leu Lys Asp Arg Leu Asp Ala Ala Asn Gly Asn Phe Phe Ala
        275                 280                 285

Leu Arg Gly Thr Val Glu Val Asn Gly Trp Asp Ala Ser Leu Gly Gly
    290                 295                 300

Leu Tyr Tyr Gly Lys Lys Asp Lys Val Thr Leu Thr Thr Ile Glu Asp
305                 310                 315                 320

Gln Gly Asn Leu Gly Ser Leu Leu Ala Gly Glu Glu Ile Phe Tyr Thr
                325                 330                 335

Asn Gly Ser Asn Leu Asn Gly Asp Ile Gly Arg Asn Ile Phe Gly Tyr
            340                 345                 350

Val Thr Ala Gly Tyr Thr Phe Asn Glu Thr Val Arg Val Gly Ala Asp
        355                 360                 365

Phe Val Tyr Gly Gly Thr Lys Thr Asn Ile Ile Gly Gln Gly Gly Lys
    370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
            420                 425                 430

<210> SEQ ID NO 42
<211> LENGTH: 431
<212> TYPE: PRT
<213> ORGANISM: Campylobacter jejuni

<400> SEQUENCE: 42

Met Lys Leu Val Lys Ile Ser Leu Val Ala Ala Leu Ala Ala Gly Ala
1               5                   10                  15

Phe Ser Ala Ala Asn Ala Thr Pro Leu Glu Glu Ala Ile Lys Asp Ile
            20                  25                  30
```

-continued

Asp Val Ser Gly Val Leu Arg Tyr Arg Tyr Glu Ser Ser Asn Pro Trp
        35                  40                  45

Ser Asn Ala Asn Phe Gly Ser Gly Ile Ser Gly Lys Gln Asp His Lys
 50                  55                  60

Tyr Arg Ala Gln Val Asn Phe Ser Gly Ala Ile Ser Asp Asn Phe Lys
 65                  70                  75                  80

Ala Phe Val Gln Phe Asp Tyr Asn Ser Gln Asp Gly Tyr Gly Thr
            85                  90                  95

Asp Ser Ile Ser Asn Thr Ser Asp Thr Leu Thr Val Arg Gln Leu Tyr
            100                 105                 110

Leu Thr Tyr Thr Asn Glu Asp Val Ala Thr Ser Val Ile Ala Gly Lys
            115                 120                 125

Gln Gln Leu Asn Thr Ile Trp Thr Asp Asn Gly Ile Asp Gly Leu Val
        130                 135                 140

Gly Thr Gly Val Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asp Asn Asn Gln Lys Ile Thr Gly Val Gln Phe Asn
            180                 185                 190

Arg Gly Asn Pro Lys Gly Asp Ser Asp Val Ser Gly Ala Leu Asp Trp
        195                 200                 205

Ser Lys Asn Ile Tyr Gly Ala Ala Ile Gly Ser Tyr Asp Ile Ala
    210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asp
                245                 250                 255

Gly Ile Asn Trp Thr Ile Glu Gly Ala Tyr Leu Gly Asn Ser Val Asp
            260                 265                 270

Asn Lys Leu Lys Asp Arg Leu Asp Ala Ala Asn Gly Asn Phe Phe Ala
        275                 280                 285

Leu Arg Gly Thr Val Glu Val Asn Gly Trp Asp Ala Ser Leu Gly Gly
    290                 295                 300

Leu Tyr Tyr Gly Lys Lys Asp Lys Val Thr Leu Thr Thr Ile Glu Asp
305                 310                 315                 320

Gln Gly Asn Leu Gly Ser Leu Leu Ala Gly Glu Glu Ile Phe Tyr Thr
                325                 330                 335

Asn Gly Ser Asn Leu Asn Gly Asp Ile Gly Arg Asn Ile Phe Gly Tyr
            340                 345                 350

Val Thr Ala Gly Tyr Thr Phe Asn Glu Thr Val Arg Val Gly Ala Asp
        355                 360                 365

Phe Val Tyr Gly Gly Thr Lys Thr Asn Ile Ile Gly Gln Gly Gly Lys
    370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
            420                 425                 430

<210> SEQ ID NO 43
<211> LENGTH: 431

<212> TYPE: PRT
<213> ORGANISM: Campylobacter jejuni

<400> SEQUENCE: 43

```
Met Lys Leu Val Lys Leu Ser Leu Val Ala Leu Ala Ala Gly Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Glu Ser Ser Asn Pro Trp
            35                  40                  45

Ser Asn Ala Asn Phe Gly Ser Gly Ile Ser Gly Lys Gln Asp His Lys
        50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Gly Tyr Gly Thr
                85                  90                  95

Asp Ser Ile Ser Asn Thr Ser Asp Thr Leu Thr Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Ala Ile Asp Gly Leu Val
    130                 135                 140

Gly Thr Gly Val Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Thr Ile Thr Gln Asp Asn Asn Gln Lys Ile Thr Gly Val Gln Phe Asn
            180                 185                 190

Arg Gly Asn Pro Lys Gly Asp Ser Asp Val Ser Gly Ala Leu Asp Trp
        195                 200                 205

Ser Lys Asn Ile Tyr Gly Ala Ala Ala Ile Gly Ser Tyr Asp Ile Ala
    210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asn
                245                 250                 255

Gly Ile Asn Trp Thr Ile Glu Gly Ala Tyr Leu Gly Asn Ser Val Asp
            260                 265                 270

Asn Lys Leu Lys Asp Arg Leu Asp Ala Ala Asn Gly Asn Phe Phe Ala
        275                 280                 285

Leu Arg Gly Thr Val Glu Val Asn Gly Trp Asp Ala Ser Leu Gly Gly
    290                 295                 300

Leu Tyr Tyr Gly Lys Lys Asp Lys Val Thr Leu Thr Thr Ile Glu Asp
305                 310                 315                 320

Gln Gly Asn Leu Gly Ser Leu Leu Ala Gly Glu Glu Ile Phe Tyr Thr
                325                 330                 335

Asn Gly Ser Asn Leu Asn Gly Asp Ile Gly Arg Asn Ile Phe Gly Tyr
            340                 345                 350

Val Thr Ala Gly Tyr Thr Phe Asn Glu Thr Val Arg Val Gly Ala Asp
        355                 360                 365

Phe Val Tyr Gly Gly Thr Lys Thr Asn Ile Ile Gly Gln Gly Gly Lys
    370                 375                 380

Lys Leu Glu Ala Val Ala Arg Val Asp Tyr Lys Tyr Ser Pro Lys Leu
385                 390                 395                 400
```

```
Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
            420                 425                 430

<210> SEQ ID NO 44
<211> LENGTH: 431
<212> TYPE: PRT
<213> ORGANISM: Campylobacter jejuni

<400> SEQUENCE: 44

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Ile
            20                  25                  30

Asp Val Ser Gly Val Leu Arg Tyr Arg Tyr Glu Ser Ser Asn Pro Trp
        35                  40                  45

Ser Asn Ala Asn Phe Gly Ser Gly Ile Ser Gly Lys Gln Asp His Lys
    50                  55                  60

Tyr Arg Ala Gln Val Asn Phe Ser Gly Ala Ile Ser Asp Asn Phe Lys
65                  70                  75                  80

Ala Phe Val Gln Phe Asp Tyr Asn Ser Gln Asp Gly Tyr Gly Ala
            85                  90                  95

Asp Ser Ile Ser Asn Thr Ser Asp Thr Leu Thr Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Phe Ile Trp Thr Asp Asn Ala Ile Asp Gly Leu Val
    130                 135                 140

Gly Thr Gly Ile Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
            165                 170                 175

Thr Ile Thr Gln Asn Gly Ser Gln Lys Ile Thr Gly Val Gln Phe Asn
        180                 185                 190

Arg Gly Asn Pro Lys Gly Asp Gly Asp Ala Ser Gly Ala Leu Asp Trp
    195                 200                 205

Ser Lys Asn Ile Tyr Gly Ala Ala Ile Gly Ser Tyr Asp Leu Ala
210                 215                 220

Gly Gly Gln Phe Asn Pro Gln Leu Trp Leu Ala Tyr Met Ser Asp Asn
225                 230                 235                 240

Ala Phe Leu Tyr Ala Leu Asp Ala Ala Tyr Ser Thr Thr Ile Phe Asp
            245                 250                 255

Gly Ile Asn Trp Thr Ile Glu Gly Ala Tyr Leu Gly Asn Ser Val Asp
        260                 265                 270

Asn Lys Leu Lys Asp Arg Leu Asn Val Ala Asn Gly Asn Phe Phe Ala
    275                 280                 285

Leu Arg Gly Thr Val Glu Val Asn Gly Trp Asp Ala Thr Leu Gly Gly
    290                 295                 300

Leu Tyr Tyr Gly Asp Lys Asp Asn Leu Thr Val Thr Ile Glu Asp
305                 310                 315                 320

Gln Gly Asn Leu Gly Ser Leu Leu Ala Gly Glu Glu Ile Phe Tyr Thr
            325                 330                 335

Arg Gly Ser Asn Leu Asn Gly Asp Leu Gly Arg Asn Ile Phe Gly Tyr
```

```
                   340                 345                 350
Val Thr Gly Gly Tyr Thr Phe Asn Glu Ala Val Arg Val Gly Ala Asp
                355                 360                 365

Phe Val Tyr Gly Gly Thr Lys Thr Asn Ile Ile Gly Gln Gly Gly Lys
            370                 375                 380

Lys Leu Glu Ala Val Ala Arg Val Asp Tyr Lys Tyr Ser Pro Lys Leu
385                 390                 395                 400

Asn Phe Ser Ala Phe Tyr Ser Tyr Val Asn Val Asp Thr Asp Pro Glu
                405                 410                 415

Ser Thr His His Asp Ala Val Arg Leu Gln Ala Leu Tyr Lys Phe
                420                 425                 430

<210> SEQ ID NO 45
<211> LENGTH: 432
<212> TYPE: PRT
<213> ORGANISM: Campylobacter jejuni

<400> SEQUENCE: 45

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Ile
            20                  25                  30

Asp Val Ser Gly Val Leu Arg Tyr Arg Tyr Glu Ser Ser Asn Pro Trp
        35                  40                  45

Ser Asn Gly Asn Tyr Gly Ser Gly Ile Ser Gly Lys Gln Asp His Lys
    50                  55                  60

Tyr Arg Ala Gln Val Asn Phe Asn Thr Ala Ile Ala Asp Asn Phe Lys
65                  70                  75                  80

Ala Phe Val Gln Phe Asp Tyr Asn Ser Lys Asp Gly Tyr Gly Glu
                85                  90                  95

Asn Ser Ile Ser Asn Thr Ser Asp Thr Leu Ser Val Arg Gln Leu Tyr
            100                 105                 110

Leu Thr Tyr Thr Asn Glu Asp Val Ala Thr Ser Val Ile Ala Gly Lys
        115                 120                 125

Gln Gln Leu Asn Thr Ile Trp Thr Asp Asn Gly Val Asp Gly Leu Val
    130                 135                 140

Gly Thr Gly Ile Lys Val Val Asn Asn Ser Ile Asp Gly Leu Thr Leu
145                 150                 155                 160

Ala Ala Phe Ala Met Asp Ser Phe Asn Glu Ala Ser Asp Thr Thr Val
                165                 170                 175

Ile Ile Thr Gln Asp Pro Ser Ser Asn Lys Ile Thr Gly Val Gln Phe
            180                 185                 190

Asn Arg Gly Asn Pro Lys Gly Asp Gly Asp Val Ser Gly Ala Leu Asp
        195                 200                 205

Trp Ser Lys Asn Ile Tyr Gly Ala Ala Ile Gly Ser Tyr Asp Ile
    210                 215                 220

Ala Gly Gly Gln Phe Asn Pro Gln Leu Trp Leu Ala Tyr Met Ser Asp
225                 230                 235                 240

Asn Ala Phe Leu Tyr Ala Leu Asp Ala Ala Tyr Asn Thr Thr Ile Phe
                245                 250                 255

Asp Gly Ile Asn Trp Thr Ile Glu Gly Ala Tyr Leu Gly Asn Ser Val
            260                 265                 270

Asp Asn Lys Leu Lys Asp Arg Leu Asp Ala Ala Asn Gly Asn Phe Phe
        275                 280                 285
```

```
Ala Leu Arg Gly Thr Val Glu Val Asn Gly Trp Asp Ala Ser Leu Gly
        290                 295                 300

Gly Leu Tyr Tyr Gly Lys Lys Asp Lys Ala Thr Val Thr Thr Ile Glu
305                 310                 315                 320

Asp Gln Gly Asn Leu Gly Ser Leu Leu Ala Gly Gln Glu Ile Phe Tyr
                325                 330                 335

Thr Arg Gly Ser Asn Leu Asn Gly Asp Leu Gly Arg Asn Ile Phe Gly
            340                 345                 350

Tyr Val Thr Ala Gly Tyr Thr Phe Asn Glu Ala Val Arg Val Gly Ala
        355                 360                 365

Asp Phe Val Tyr Gly Gly Thr Lys Thr Gly Glu Ile Gly Asn Gly Gly
    370                 375                 380

Lys Lys Leu Glu Ala Val Ala Arg Val Asp Tyr Lys Tyr Ser Pro Lys
385                 390                 395                 400

Leu Asn Phe Ser Ala Phe Tyr Ser Tyr Val Asn Val Asp Thr Asp Pro
                405                 410                 415

Glu Ser Thr His His Asp Ala Val Arg Leu Gln Ala Leu Tyr Lys Phe
            420                 425                 430

<210> SEQ ID NO 46
<211> LENGTH: 429
<212> TYPE: PRT
<213> ORGANISM: Campylobacter jejuni

<400> SEQUENCE: 46

Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Ile
                20                  25                  30

Asp Val Ser Gly Val Leu Arg Tyr Arg Tyr Asp Thr Ser Asn Asp Trp
            35                  40                  45

Asn Asn Ala Gly Phe Gly Ser Gly Ile Ser Gly Lys Gln Thr His Asn
        50                  55                  60

Tyr Arg Ala Gln Ile Asn Phe Ser Gly Ala Ile Ala Asp Asn Phe Lys
65                  70                  75                  80

Ala Phe Val Gln Phe Asp Tyr Ala Ala Val Asp Gly Gly Tyr Asn Val
                85                  90                  95

Thr Asn Gly Thr Gly Asn Gln Arg Asn Asp Gln Asn Ser Leu Thr Val
            100                 105                 110

Arg Gln Leu Tyr Leu Thr Tyr Thr Asn Glu Asp Val Ala Thr Ser Val
        115                 120                 125

Ile Ala Gly Lys Gln Gln Leu Asn Thr Ile Trp Thr Asp Asn Asp Ile
    130                 135                 140

Asp Gly Leu Val Gly Thr Gly Ile Lys Trp Asn Asn Ser Ile Asp Gly
145                 150                 155                 160

Leu Thr Leu Ala Ala Phe Ala Val Asp Ser Tyr Asn Thr Asp Glu Gln
                165                 170                 175

Gly Tyr Lys Asp Asn Asn Gly Arg Pro Asp Leu Thr Tyr Thr Gly Asp
            180                 185                 190

Ala Ser Gln Tyr Leu Thr Trp Gly Asn Ile Tyr Gly Ala Ala Ala Val
        195                 200                 205
```

```
Gly Ser Tyr Asp Leu Ala Gly Gly Gln Phe Asn Pro Gln Leu Trp Leu
    210             215                 220
Ala Tyr Met Ser Asp Asn Ala Phe Leu Tyr Ala Leu Asp Leu Ala Tyr
225             230                 235                 240
Asn Thr Thr Ile Phe Asp Gly Ile Asn Trp Ser Ile Glu Gly Ala Tyr
                245                 250                 255
Leu Gly Asn Ser Val Asp Asn Lys Leu Lys Asp Arg Phe His Ala Ala
            260                 265                 270
Gly Asp Pro Glu Ser Ser Ala Ala Asn Gly Asn Phe Phe Ala Leu Arg
        275                 280                 285
Gly Thr Val Glu Val Asn Gly Trp Asp Ala Ser Leu Gly Gly Leu Tyr
    290                 295                 300
Tyr Gly Lys Lys Asp Lys Phe Thr Val Thr Thr Ile Glu Asp Gln Gly
305             310                 315                 320
Asn Leu Gly Ser Leu Leu Ala Gly Glu Glu Ile Phe Tyr Thr His Gly
            325                 330                 335
Ser Arg Leu Asn Gly Asp Ala Gly Arg Asn Ile Phe Gly Tyr Val Thr
            340                 345                 350
Gly Gly Tyr Thr Phe Asn Glu Thr Val Arg Val Gly Ala Asp Phe Val
        355                 360                 365
Tyr Gly Gly Thr Lys Thr Glu Asn Val Gly Glu Gly Gly Lys Lys Leu
    370                 375                 380
Glu Ala Val Ala Arg Val Asp Tyr Lys Tyr Ser Pro Lys Leu Asn Phe
385             390                 395                 400
Ser Ala Phe Tyr Ser Tyr Val Asn Val Asp Arg Asp Pro Glu Ser Thr
            405                 410                 415
His His Asp Ala Val Arg Leu Gln Ala Leu Tyr Lys Phe
            420                 425
```